US012194062B2

(12) United States Patent
Gumrukcu

(10) Patent No.: US 12,194,062 B2
(45) Date of Patent: Jan. 14, 2025

(54) METHODS FOR NON-MYELOABLATIVE BONE MARROW RECONSTITUTION

(71) Applicant: WEIRD SCIENCE LLC, West Hollywood, CA (US)

(72) Inventor: Serhat Gumrukcu, West Hollywood, CA (US)

(73) Assignee: WEIRD SCIENCE LLC, West Hollywood, CA (US)

( * ) Notice: Subject to any disclaimer, the term of this patent is extended or adjusted under 35 U.S.C. 154(b) by 151 days.

(21) Appl. No.: 16/191,816

(22) Filed: Nov. 15, 2018

(65) Prior Publication Data
US 2019/0269734 A1 Sep. 5, 2019

Related U.S. Application Data

(60) Provisional application No. 62/586,813, filed on Nov. 15, 2017.

(51) Int. Cl.
*A61K 35/28* (2015.01)
*A61K 31/664* (2006.01)
*A61K 31/675* (2006.01)
*A61K 35/12* (2015.01)
*A61K 39/00* (2006.01)
*A61K 45/06* (2006.01)
*A61P 31/18* (2006.01)
*C07K 14/435* (2006.01)
*C12N 9/02* (2006.01)
*C12N 15/113* (2010.01)
*C12N 15/86* (2006.01)

(52) U.S. Cl.
CPC .......... *A61K 35/28* (2013.01); *A61K 31/664* (2013.01); *A61K 31/675* (2013.01); *A61K 35/12* (2013.01); *A61K 39/461* (2023.05); *A61K 39/464838* (2023.05); *A61K 45/06* (2013.01); *A61P 31/18* (2018.01); *C07K 14/435* (2013.01); *C12N 9/0008* (2013.01); *C12N 15/1138* (2013.01); *C12N 15/86* (2013.01); *A61K 2035/124* (2013.01); *A61K 2239/31* (2023.05); *A61K 2239/38* (2023.05); *C12N 2310/14* (2013.01); *C12N 2310/531* (2013.01); *C12N 2330/50* (2013.01)

(58) Field of Classification Search
None
See application file for complete search history.

(56) References Cited

U.S. PATENT DOCUMENTS 6,268,138 B1 * 7/2001 Dalla-Favera .......... A61P 43/00
435/6.14
2003/0099621 A1 * 5/2003 Chow ...................... A61P 37/04
424/93.21
2008/0003682 A1 * 1/2008 Lois-Caballe .......... C12N 15/86
435/456
2010/0129329 A1 * 5/2010 Haley ..................... A61K 35/51
424/93.7
2012/0020179 A1 1/2012 Xiao et al.
2012/0148577 A1 * 6/2012 Fuchs ....................... A61P 7/06
424/133.1
2012/0201794 A1 8/2012 Chen et al.
2017/0107519 A1 * 4/2017 Lois-Caballe ...... C12N 15/1138

FOREIGN PATENT DOCUMENTS

| JP | H8-501221 A | 2/1996 | |
| JP | 2010-520757 A | 6/2010 | |
| JP | 2012-533299 A | 12/2012 | |
| WO | 1994023015 A1 | 10/1994 | |
| WO | 2003006691 A1 | 1/2003 | |
| WO | WO-03006691 A1 * | 1/2003 | ............. A61K 48/00 |
| WO | 2011008348 A2 | 1/2011 | |
| WO | WO-2013093920 A2 * | 6/2013 | ........... A61K 31/198 |
| WO | 2013155572 A1 | 10/2013 | |
| WO | 2016057821 A2 | 4/2016 | |

OTHER PUBLICATIONS

Monach et al Arthritis & Rheumatism, 62, ( 1), 9-21 (Year: 2010).*
McKinley et al (Clin J Am Sec Nephrol 4: 1754-1760 (Year: 2009).*
McKinley et al., Clin J Am Soc Nephrol. 4:1754-1760 (Year: 2009).*
Bacigalupo et al., "Defining the Intensity of Conditioning Regimens", Biol. Blood Marrow transplant, (2009) 15(12): 1628-1633.
International Search Report received in Application No. PCT/US2018/061211, mailed Feb. 1, 2019.
Jaeger et al., "Improved predictions of secondary structures for RNA", Proc. Natl. Acad. Sci. USA, (1989) 86: 7706-7710.
McKinley et al., "Oral Cyclophosphamide for Lupus Glomerulonephritis: An Underused Therapeutic Option", Clin. J. Am. Soc. Nephrol, (2009) 4: 1754-1760.
Needleman et al., "A General Method Applicable to the Search for Similarities in the Amino Acid Sequence of Two Proteins", J. Mol. Biol., (1970) 48: 443-453.
Pearson et al., "Improved tools for biological sequence comparison.", Pro. Natl. Acad. Sci. U.S.A., (1988) 85: 2444-2448.
Smith et al., "Comparison of Biosequences" Adv. Appl. Math. (1981), 2: 482-489.
Zangi et al., "Modified mRNA directs the fate of heart progenitor cells and induces vascular regeneration after myocardial infarction", Nature Biotech., (2013) 31: 898-907.

(Continued)

*Primary Examiner* — Anoop K Singh
(74) *Attorney, Agent, or Firm* — Leason Ellis LLP

(57) ABSTRACT

The disclosure relates generally to methods and compositions for performing bone marrow transplants using a non-myeloablative chemotherapeutic agent and chemotherapeutic-resistant cells. Using the methods and compositions described herein, a patient's bone marrow may be reconstituted and the patient avoids adverse side effects, including myeloablation and/or an impaired immune system.

8 Claims, 13 Drawing Sheets
Specification includes a Sequence Listing.

(56) References Cited

OTHER PUBLICATIONS

Zuker, "On Finding All Suboptimal Foldings of an RNA Molecule", M., Science, (1989) 244: 48-52.

Halder et al., "Poster #431 Gene modified CD34 + cells with increased ALDH1 expression confers in vitro protection against cyclophosphamide", (2020) XP055780397.

Magni et al., "Induction of cyclophosphamide-resistance by aldehyde-dehydrogenase gene transfer", Blood, American Society of Hematology, US, vol. 87, No. 3, (1996), pp. 1097-1103, XP002589606, ISSN: 0006-4971.

Budak-Alpdogan et al., "Hematopoietic stem cell gene therapy with drug resistance genes: an update", Cancer Gene Therapy, vol. 12, No. 11, (2005), pp. 849-863, XP055781416, New York ISSN: 0929-1903, DOI: 10.1038/sj.cgt.7700866.

Myburgh Renier et al, "Abstract", Journal of Virology, US, vol. 89, No. 13, p. 6761-6772. DOI: http://dx.doi.org/10.1128/JVI.00277-15.

Michele Magni et al., Induction of cyclophosphamide-resistance by aldehyde-dehydrogenase gene transfer, 1996, Blood 87(3):1097-1103.

Sugita et al., HLA—haploidentical stem cell transplantation using posttransplant cyclophosphamide—current trends and issues—, Journal of Hematopoietic Cell Transplantation, 2015, vol. 4 No. 1, p. 9-22.

Sugita, "HLA-haploidentical stem cell transplantation using post-transplant cyclophosphamide—current trends and issues—", Journal of Hematopoietic Cell Transplantation, 2015, vol. 4 No. 1, p. 9-22, an English translation is attached hereto.

Japanese Office Action in JP Application No. 2020-545238, mailed Jan. 19, 2024, an English translation is attached hereto (4 pages).

NCBI Reference Sequence: NM_000689.1, "*Homo sapiens* aldehyde dehydrogenase 1, soluble (ALDH1) mRNA, and translated products", GI:4502030, GeneBank, Mar. 19, 1999.

* cited by examiner

Collection of donor mouse stem and progenitor cells

Pretreatment of recipient mice with Fludarabine

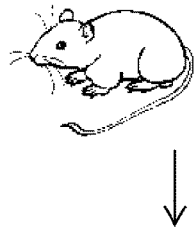

Lentiviral transduction of donor mouse stem and progenitor cells ⟶

Transplantation of recipient mice with modified door stem and progenitor cells

Daily CTX treatment

Weekly blood collection for FACS analysis and CBC analysis

Termination of study: bone marrow collection to demonstrate full engraftment

Fig. 7

SEQUENCE LISTING

```
<160> NUMBER OF SEQ ID NOS: 19

<210> SEQ ID NO 1
<211> LENGTH: 1503
<212> TYPE: DNA
<213> ORGANISM: Artificial Sequence
<220> FEATURE:
<223> OTHER INFORMATION: hALDH1-cDNA

<400> SEQUENCE: 1
atgtcatcct caggcacgcc agacttacct gtcctactca ccgatttgaa gattcaatat      60
actaagatct tcataaacaa tgaatggcat gattcagtga gtggcaagaa atttcctgtc     120
tttaatcctg caactgagga ggagctctgc caggtagaag aaggagataa ggaggatgtt     180
```

```
gacaaggcag tgaaggccgc aagacaggct tttcagattg atccccgtg gcgtactatg      240 gatgcttccg agagggggcg actattatac aagttggctg atttaatcga aagagatcgt      300
ctgctgctgg cgacaatgga gtcaatgaat ggtggaaaac tctattccaa tgcatatctg      360
aatgatttag caggctgcat caaaacattg cgctactgtg caggttgggc tgacaagatc      420
cagggccgta caataccaat tgatggaaat tttttttacat atacaagaca tgaacctatt      480
ggtgtatgtg ccaaatcat tccttggaat ttcccgttgg ttatgctcat ttggaagata      540
gggcctgcac tgagctgtgg aaacacagtg gttgtcaaac cagcagagca aactcctctc      600
actgctctcc acgtgcatc tttaataaaa gaggcagggt ttcctcctgg agtagtgaat      660
attgttcctg gttatgggcc tacagcaggg gcagccattt cttctcacat ggatatagac      720
aaagtagcct tcacaggatc aacagagctt ggcaagttga tcaaagaagc tgccgggaaa      780
agcaatctga gagggtgac cctggagctt ggaggaaaga gcccttgcat tgtgttagct      840
gatgccgact tggacaatgc tgttgaattt gcacaccatg gggtattcta ccaccagggc      900
cagtgttgta tagccgcatc caggattttt gtggaagaat caatttatga tgagtttgtt      960
cgaaggagtg ttgagcgggc taagaagtat atccttggaa atcctctgac cccaggagtc     1020
actcaaggcc ctcagattga caaggaacaa tatgataaaa tacttgacct cattgagagt     1080
gggaagaaag aaggggccaa actggaatgt ggaggaggcc cgtgggggaa taaaggctac     1140
tttgtccagc ccacagtgtt ctctaatgtt acagatgaga tgcgcattgc caaagaggag     1200
atttttggac cagtgcagca aatcatgaag tttaaatctt tagatgacgt gatcaaaaga     1260
gcaaacaata ctttctatgg cttatcagca ggagtgttta ccaaagacat tgataaagcc     1320
ataacaatct cctctgctct gcaggcagga acagtgtggg tgaattgcta tggcgtggta     1380
agtgcccagt gccccttttgg tggattcaag atgtctggaa atggaagaga actgggagag     1440 tacggttttcc atgaatatac agaggtcaaa acagtcacag tgaaaatctc tcagaagaac     1500
tca                                                                 1503
```

<210> SEQ ID NO 2
<211> LENGTH: 10781
<212> TYPE: DNA
<213> ORGANISM: Artificial Sequence
<220> FEATURE:
<223> OTHER INFORMATION: pLV-Puro-EF1A-hALDH1A1:T2A:EGFP

<400> SEQUENCE: 2

```
aatgtagtct tatgcaatac tcttgtagtc ttgcaacatg gtaacgatga gttagcaaca       60
tgccttacaa ggagagaaaa agcaccgtgc atgccgattg gtggaagtaa ggtggtacga      120
tcgtgcctta ttaggaaggc aacagacggg tctgacatgg attggacgaa ccactgaatt      180
gccgcattgc agagatattg tatttaagtg cctagctcga tacataaacg ggtctctctg      240
gttagaccag atctgagcct gggagctctc tggctaacta gggaacccac tgcttaagcc      300
tcaataaagc ttgccttgag tgcttcaagt agtgtgtgcc cgtctgttgt gtgactctgg      360
taactagaga tccctcagac ccttttagtc agtgtggaaa atctctagca gtggcgcccg      420
aacagggact tgaaagcgaa agggaaacca ggagagctct ctcgacgcag gactcggctt      480
gctgaagcgc gcacggcaag aggcgagggg cggcgactgg tgagtacgcc aaaaattttg      540
actagcggag gctagaagga gagagatggg tgcgagagcg tcagtattaa gcggggggaga      600 attagatcgc gatgggaaaa aattcggtta aggccagggg gaagaaaaaa atataaatta      660
aaacatatag tatgggcaag cagggagcta gaacgattcg cagttaatcc tggcctgtta      720
```

```
gaaacatcag aaggctgtag acaaatactg ggacagctac aaccatccct tcagacagga    780
tcagaagaac ttagatcatt atataataca gtagcaaccc tctattgtgt gcatcaaagg    840
atagagataa aagacaccaa ggaagcttta gacaagatag aggaagagca aaacaaaagt    900
aagaccaccg cacagcaagc ggccgctgat cttcagacct ggaggaggag atatgaggga    960
caattggaga agtgaattat ataaatataa gtagtaaaaa attgaaccat taggagtagc   1020
acccaccaag gcaaagagaa gagtggtgca gagagaaaaa agagcagtgg gaataggagc   1080
tttgttcctt gggttcttgg gagcagcagg aagcactatg ggcgcagcgt caatgacgct   1140
gacggtacag gccagacaat tattgtctgg tatagtgcag cagcagaaca atttgctgag   1200
ggctattgag gcgcaacagc atctgttgca actcacagtc tggggcatca agcagctcca   1260
ggcaagaatc ctggctgtgg aaagatacct aaaggatcaa cagctcctgg ggatttgggg   1320
ttgctctgga aaactcattt gcaccactgc tgtgccttgg aatgctagtt ggagtaataa   1380
atctctggaa cagatttgga atcacacgac ctggatggag tgggacagag aaattaacaa   1440
ttacacaagc ttaatacact ccttaattga agaatcgcaa aaccagcaag aaaagaatga   1500
acaagaatta ttggaattag ataaatgggc aagtttgtgg aattggttta acataacaaa   1560
ttggctgtgg tatataaaat tattcataat gatagtagga ggcttggtag gtttaagaat   1620 agttttgct gtactttcta tagtgaatag agttaggcag ggatattcac cattatcgtt   1680
tcagacccac ctcccaaccc cgaggggacc cgacaggccc gaaggaatag aagaagaagg   1740
tggagagaga gacagagaca gatccattcg attagtgaac ggatctcgac ggtatcgcta   1800
gcttttaaaa gaaaaggggg gattggggg tacagtgcag gggaagaat agtagacata   1860 atagcaacag acatcaaaac taagaatta caaaacaaa ttacaaaaat tcaaaatttt   1920
actagtgatt atcggatcaa cttttgtatag aaaagttggg ctccggtgcc cgtcagtggg   1980
cagagcgcac atcgcccaca gtccccgaga agttggggg aggggtcggc aattgaaccg   2040
gtgcctagag aaggtggcgc ggggtaaact gggaaagtga tgtcgtgtac tggctccgcc   2100
tttttcccga gggtgggggga gaaccgtata taagtgcagt agtcgccgtg aacgttcttt   2160
ttcgcaacgg gtttgccgcc agaacacagg taagtgccgt gtgtggttcc cgcgggcctg   2220
gcctctttac gggttatggc ccttgcgtgc cttgaattac ttccacctgg ctgcagtacg   2280
tgattcttga tcccgagctt cgggttggaa gtgggtggga gagttcgagg ccttgcgctt   2340
aaggagcccc ttcgcctcgt gcttgagttg aggcctggcc tgggcgctgg ggccgccgcg   2400
tgcgaatctg gtggcacctt cgcgcctgtc tcgctgcttt cgataagtct ctagccattt   2460 aaaattttg atgacctgct gcgacgcttt ttttctggca agatagtctt gtaaatgcgg   2520
gccaagatct gcacactggt atttcggttt tggggccgc gggcggcgac ggggcccgtg   2580
cgtcccagcg cacatgttcg gcgaggcggg gcctgcgagc gcggccaccg agaatcggac   2640
gggggtagtc tcaagctggc cggcctgctc tggtgcctgg tctcgcgccg ccgtgtatcg   2700
ccccgccctg gcggcaagg ctggcccggt cggcaccagt tgcgtgagcg aaagatggc   2760 cgcttcccgg ccctgctgca gggagctcaa aatggaggac gcggcgctcg ggagagcggg   2820
cgggtgagtc acccacacaa aggaaaaggg ccttccgtc ctcagccgtc gcttcatgtg   2880
actccacgga gtaccgggcg ccgtccaggc acctcgatta ttctcgagc ttttggagta   2940 cgtcgtcttt aggttggggg gaggggtttt atgcgatgga gtttcccac actgagtggg   3000 tggagactga agttaggcca gcttggcact tgatgtaatt ctccttggaa tttgcccttt   3060
```

```
ttgagtttgg atcttggttc attctcaagc ctcagacagt ggttcaaagt ttttttcttc    3120
catttcaggt gtcgtgacaa gtttgtacaa aaaagcaggc tgccaccatg tcatcctcag    3180
gcacgccaga cttacctgtc ctactcaccg atttgaagat tcaatatact aagatcttca    3240
taaacaatga atggcatgat tcagtgagtg caagaaatt tcctgtcttt aatcctgcaa     3300
ctgaggagga gctctgccag gtagaagaag gagataagga ggatgttgac aaggcagtga    3360
aggccgcaag acaggctttt cagattggat ccccgtggcg tactatggat gcttccgaga    3420
gggggcgact attatacaag ttggctgatt aatcgaaag agatcgtctg ctgctggcga     3480
caatggagtc aatgaatggt ggaaaactct attccaatgc atatctgaat gatttagcag    3540
gctgcatcaa acattgcgc tactgtgcag gttgggctga caagatccag ggccgtacaa     3600
taccaattga tggaaatttt tttacatata caagacatga acctattggt gtatgtggcc    3660
aaatcattcc ttggaatttc ccgttggtta tgctcatttg aagatagggg cctgcactga   3720
gctgtggaaa cacagtggtt gtcaaaccag cagagcaaac tcctctcact gctctccacg    3780
tggcatcttt aataaaagag gcagggtttc ctcctggagt agtgaatatt gttcctggtt    3840
atgggcctac agcaggggca gccatttctt ctcacatgga tatagacaaa gtagccttca    3900
caggatcaac agaggttggc aagttgatca agaagctgc cgggaaaagc aatctgaaga    3960
gggtgaccct ggagcttgga ggaaagagcc cttgcattgt gttagctgat gccgacttgg    4020
acaatgctgt tgaatttgca caccatgggg tattctacca ccaggccag tgttgtatag     4080
ccgcatccag gattttgtg aagaatcaa tttatgatga gtttgttcga aggagtgttg      4140
agcgggctaa gaagtatatc cttggaaatc tctgaccccc aggagtcact caaggccctc    4200
agattgacaa ggaacaatat gataaaatac ttgacctcat tgagagtggg aagaaagaag    4260
gggccaaact ggaatgtgga ggaggcccgt gggggaataa aggctacttt gtccagccca    4320
cagtgttctc taatgttaca gatgagatgc gcattgccaa agaggagatt tttggaccag    4380
tgcagcaaat catgaagttt aaatctttag atgacgtgat caaaagagca acaatactt    4440
tctatggctt atcagcagga gtgtttacca aagacattga taaagccata acaatctcct    4500
ctgctctgca ggcaggaaca gtgtgggtga attgctatgg cgtggtaagt gcccagtgcc    4560
cctttggtgg attcaagatg tctggaaatg gaagagaact gggagagtac ggtttccatg    4620
aatatacaga ggtcaaaaca gtcacagtga aatctctca gaagaactca ggaagcggag     4680
agggcagggg aagtcttcta acatgcgggg acgtggagga aaatcccggc ccatggtga    4740
gcaagggcga ggagctgttc accgggtgg tgcccatcct ggtcgagctg gacggcgacg    4800
taaacggcca agttcagc gtgtccggcg agggcgaggg cgatgccacc tacggcaagc     4860
tgaccctgaa gttcatctgc accaccggca agctgcccgt gccctggccc accctcgtga    4920
ccaccctgac ctacggcgtg cagtgcttca gccgctaccc cgaccacatg aagcagcacg    4980
acttcttcaa gtccgccatg cccgaaggct acgtccagga gcgcaccatc ttcttcaagg    5040
acggcgcaa ctacaagacc cgcgccgagg tgaagttcga gggcgacacc ctggtgaacc     5100
gcatcgagct gaagggcatc gacttcaagg aggacggcaa catcctgggg cacaagctgg    5160
agtacaacta caacagccac aacgtctata tcatggccga caagcagaag aacggcatca    5220
aggtgaactt caagatccgc cacaacatcg aggacggcag cgtgcagctc gccgaccact    5280
accagcagaa cacccccatc ggcgacggcc ccgtgctgct gcccgacaac cactacctga    5340
gcacccagtc cgccctgagc aaagacccca acgagaagcg cgatcacatg gtcctgctgg    5400
agttcgtgac cgccgccggg atcactctcg gcatggacga gctgtacaag taaacccagc    5460
```

```
tttcttgtac aaagtggtga taatcgaatt ccgataatca acctctggat tacaaaattt   5520
gtgaaagatt gactggtatt cttaactatg ttgctccttt tacgctatgt ggatacgctg   5580
ctttaatgcc tttgtatcat gctattgctt cccgtatggc tttcattttc tcctccttgt   5640
ataaatcctg gttgctgtct ctttatgagg agttgtggcc cgttgtcagg caacgtggcg   5700
tggtgtgcac tgtgtttgct gacgcaaccc ccactggttg gggcattgcc accacctgtc   5760
agctcctttc cgggactttc gctttccccc tccctattgc cacggcggaa ctcatcgccg   5820
cctgccttgc ccgctgctgg acaggggctc ggctgttggg cactgacaat tccgtggtgt   5880
tgtcggggaa gctgacgtcc tttccatggc tgctcgcctg tgttgccacc tggattctgc   5940
gcgggacgtc cttctgctac gtcccttcgg ccctcaatcc agcggacctt ccttcccgcg   6000
gcctgctgcc ggctctgcgg cctcttccgc gtcttcgcct tcgccctcag acgagtcgga   6060 tctcccttttg ggccgcctcc ccgcatcggg aattcccgcg gttcgaattc taccgggtag   6120
gggaggcgct tttcccaagg cagtctggag catgcgcttt agcagcccg ctgggcactt   6180 ggcgctacac aagtggcctc tggcctcgca cacattccac atccaccggt aggcgccaac   6240
cggctccgtt ctttggtggc cccttcgcgc caccttctac tcctccccta gtcaggaagt   6300 tccccccgc cccgcagctc gcgtcgtgca ggacgtgaca aatggaagta gcacgtctca   6360
ctagtctcgt gcagatggac agcaccgctg agcaatggaa gcgggtaggc ctttggggca   6420
gcggccaata gcagctttgc tccttcgctt tctgggctca gaggctggga aggggtgggt   6480 ccggggggcgg gctcagggc gggctcaggg gcggggcggg cgcccgaagg tcctccggag   6540
gcccggcatt ctgcacgctt caaaagcgca cgtctgccgc gctgttctcc tcttcctcat   6600
ctccgggcct ttcgacctca cgtggccacc atgaccgagt acaagcccac ggtgcgcctc   6660
gccacccgcg acgacgtccc cagggccgta cgcaccctcg ccgccgcgtt cgccgactac   6720
cccgccacgc gccacaccgt cgatccggac cgccacatcg agcgggtcac cgagctgcaa   6780
gaactcttcc tcacgcgcgt cgggctcgac atcggcaagg tgtgggtcgc ggacgacggc   6840
gccgcggtgg cggtctggac cacgccgag agcgtcgaag cggggcggt gttcgccgag   6900 atcggcccgc gcatggccga gttgagcggt tcccggctgg ccgcgcagca acagatggaa   6960
ggcctcctgg cgccgcaccg gcccaaggag cccgcgtggt tcctggccac cgtcggcgtc   7020
tcgcccgacc accagggcaa gggtctggc agcgccgtcg tgctccccgg agtggaggcg   7080
gccgagcgcg ccggggtgcc cgccttcctg gagacctccg cgccccgcaa cctcccttc   7140 tacgagcggc tcggcttcac cgtcaccgcc gacgtcgagg tgcccgaagg accgcgcacc   7200
tggtgcatga cccgcaagcc cggtgcctga ggtaccttta agaccaatga cttacaaggc   7260
agctgtagat cttagccact ttttaaaga aagggggga ctggaagggc taattcactc   7320
ccaacgaaga caagatctgc ttttttgcttg tactgggtct ctctggttag accagatctg   7380
agcctgggag ctctctggct aactagggaa cccactgctt aagcctcaat aaagcttgcc   7440
ttgagtgctt caagtagtgt gtgcccgtct gttgtgtgac tctggtaact agagatccct   7500
cagacccttt tagtcagtgt ggaaaatctc tagcagtagt agttcatgtc atcttattat   7560
tcagtattta aacttgcaa agaaatgaat atcagagagt gagaggaact tgtttattgc   7620
agcttataat ggttacaaat aaagcaatag catcacaaat ttcacaaata aagcatttt   7680 ttcactgcat tctagttgtg gtttgtccaa actcatcaat gtatcttatc atgtctggct   7740
ctagctatcc cgcccctaac tccgcccatc ccgccctaa ctccgccag ttccgcccat   7800
```

```
tctccgcccc atggctgact aattttttt atttatgcag aggccgaggc cgcctcggcc     7860
tctgagctat tccagaagta gtgaggaggc ttttttggag gcctaggac gtacccaatt     7920 cgccctatag tgagtcgtat tacgcgcgct cactggccgt cgttttacaa cgtcgtgact    7980
gggaaaaccc tggcgttacc caacttaatc gccttgcagc acatcccct ttcgccagct     8040 ggcgtaatag cgaagaggcc cgcaccgatc gcccttccca acagttgcgc agcctgaatg    8100
gcgaatggga cgcgccctgt agcggcgcat taagcgcggc gggtgtggtg gttacgcgca    8160
gcgtgaccgc tacacttgcc agcgccctag cgcccgctcc tttcgctttc ttcccttcct    8220
ttctcgccac gttcgccggc tttccccgtc aagctctaaa tcgggggctc cctttagggt    8280
tccgatttag tgctttacgg cacctcgacc ccaaaaaact tgattagggt gatggttcac    8340
gtagtgggcc atcgccctga tagacggttt ttcgcccttt gacgttggag tccacgttct    8400
ttaatagtgg actcttgttc caaactggaa caacactcaa ccctatctcg gtctattctt    8460
ttgatttata agggattttg ccgatttcgg cctattggtt aaaaaatgag ctgatttaac    8520
aaaaatttaa cgcgaatttt aacaaaatat taacgcttac aatttaggtg cacttttcg     8580 gggaaatgtg cgcggaaccc ctatttgttt attttctaa atacattcaa atatgtatcc     8640
gctcatgaga caataaccct gataaatgct tcaataatat tgaaaagga agagtatgag     8700 tattcaacat ttccgtgtcg cccttattcc cttttttgcg gcattttgcc ttcctgtttt    8760
tgctcaccca gaaacgctgg tgaaagtaaa agatgctgaa gatcagttgg gtgcacgagt    8820
gggttacatc gaactggatc tcaacagcgg taagatcctt gagagttttc gccccgaaga    8880
acgttttcca atgatgagca cttttaaagt tctgctatgt ggcgcggtat tatcccgtat    8940
tgacgccggg caagagcaac tcggtcgccg catacactat tctcagaatg acttggttga    9000
gtactcacca gtcacagaaa agcatcttac ggatggcatg acagtaagag aattatgcag    9060
tgctgccata accatgagtg ataacactgc ggccaactta cttctgacaa cgatcggagg    9120
accgaaggag ctaaccgctt ttttgcacaa catgggggat catgtaactc gccttgatcg    9180
ttgggaaccg gagctgaatg aagccatacc aaacgacgag cgtgacacca cgatgcctgt    9240
agcaatggca acaacgttgc gcaaactatt aactggcgaa ctacttactc tagcttcccg    9300
gcaacaatta atagactgga tggaggcgga taaagttgca ggaccacttc tgcgctcggc    9360
ccttccggct ggctggttta ttgctgataa atctggagcc ggtgagcgtg gtctcgcgg     9420 tatcattgca gcactggggc cagatggtaa gccctcccgt atcgtagtta tctacacgac    9480
ggggagtcag gcaactatgg atgaacgaaa tagacagatc gctgagatag gtgcctcact    9540
gattaagcat tggtaactgt cagaccaagt ttactcatat atactttaga ttgatttaaa    9600
acttcatttt taatttaaaa ggatctaggt gaagatcctt tttgataatc tcatgaccaa    9660
aatcccttaa cgtgagtttt cgttccactg agcgtcagac cccgtagaaa agatcaaagg    9720
atcttcttga tccttttt tctgcgcgt aatctgctgc ttgcaaacaa aaaaaccacc       9780
gctaccagcg gtggtttgtt tgccggatca agagctacca actctttttc cgaaggtaac    9840
tggcttcagc agagcgcaga taccaaatac tgttcttcta gtgtagccgt agttaggcca    9900
ccacttcaag aactctgtag caccgcctac atacctcgct ctgctaatcc tgttaccagt    9960
ggctgctgcc agtggcgata agtcgtgtct taccggggttg gactcaagac gatagttacc   10020
ggataaggcg cagcggtcgg gctgaacggg gggttcgtgc acacagccca gcttggagcg    10080
aacgacctac accgaactga gatacctaca gcgtgagcta tgagaaagcg ccacgcttcc    10140
cgaagagaga aaggcggaca ggtatccggt aagcggcagg gtcggaacag gagagcgcac    10200
```

```
gagggagctt ccaggggggaa acgcctggta tctttatagt cctgtcgggt ttcgccacct    10260
ctgacttgag cgtcgatttt tgtgatgctc gtcaggggg cggagcctat ggaaaaacgc     10320
cagcaacgcg gccttttac ggttcctggc cttttgctgg cctttgctc acatgttctt      10380 tcctgcgtta tccctgatt ctgtggataa ccgtattacc gcctttgagt gagctgatac     10440
cgctcgccgc agccgaacga ccgagcgcag cgagtcagtg agcgaggaag cggaagagcg    10500
cccaatacgc aaaccgcctc tccccgcgcg ttggccgatt cattaatgca gctggcacga   10560
caggtttccc gactggaaag cgggcagtga gcgcaacgca attaatgtga gttagctcac    10620
tcattaggca ccccaggctt tacactttat gcttccggct cgtatgttgt gtggaattgt    10680
gagcggataa caatttcaca caggaaacag ctatgaccat gattacgcca agcgcgcaat    10740
taaccctcac taaagggaac aaaagctgga gctgcaagct t                        10781

<210> SEQ ID NO 3
<211> LENGTH: 408
<212> TYPE: DNA
<213> ORGANISM: Artificial Sequence
<220> FEATURE:
<223> OTHER INFORMATION: Membrane Anchored C46 Fusion Inhibitor

<400> SEQUENCE: 3
atgggcgccg cgccaccgg cagagccatg gacggcccca gactgctgct gctgctgctg        60
ctgggcgtga gcctgggcgg cgccagaagc tggatggagt gggacagaga gatcaacaac       120
tacaccagcc tgatccacag cctgatcgag gagagccaga accagcagga gaagaacgag       180
caggagctgc tggagctgga caagtgggcc agcctgtgga actggttcag aagcgagaga       240
aagtgctgcg tggagtgccc cccctgcccc gccccccccg tggccggccc cctgatcgcc       300
ctggtgacca gcggcgccct gctggccgtg ctgggcatca ccggctactt cctgatgaac       360
agaagaagct ggagccccac cggcgagaga ctggagctgg agccctaa                    408

<210> SEQ ID NO 4
<211> LENGTH: 9623
<212> TYPE: DNA
<213> ORGANISM: Artificial Sequence
<220> FEATURE:
<223> OTHER INFORMATION: pLV: hALDH1A1:T2A:maC46:shCCR5

<400> SEQUENCE: 4
aatgtagtct tatgcaatac tcttgtagtc ttgcaacatg gtaacgatga gttagcaaca         60
tgccttacaa ggagagaaaa agcaccgtgc atgccgattg gtggaagtaa ggtggtacga       120
tcgtgcctta ttaggaaggc aacagacggg tctgacatgg attggacgaa ccactgaatt       180
gccgcattgc agagatattg tatttaagtg cctagctcga tacataaacg ggtctctctg       240
gttagaccag atctgagcct gggagctctc tggctaacta gggaacccac tgcttaagcc       300
tcaataaagc ttgccttgag tgcttcaagt agtgtgtgcc cgtctgttgt gtgactctgg       360
taactagaga tccctcagac ccttttagtc agtgtggaaa atctctagca gtggcgcccg       420
aacagggact tgaaagcgaa agggaaacca gaggagctct ctcgacgcag gactcggctt       480
gctgaagcgc gcacggcaag aggcgagggg cggcgactgg tgagtacgcc aaaaattttg       540
actagcggag gctagaagga gagagatggg tgcgagagcg tcagtattaa gcggggggaga     600 attagatcgc gatgggaaaa aattcggtta aggccagggg gaagaaaaaa atataaatta      660
aaacatatag tatgggcaag cagggagcta gaacgattcg cagttaatcc tggcctgtta     720
```

```
gaaacatcag aaggctgtag acaaatactg ggacagctac aaccatccct tcagacagga      780
tcagaagaac ttagatcatt atataataca gtagcaaccc tctattgtgt gcatcaaagg      840
atagagataa aagacaccaa ggaagcttta gacaagatag aggaagagca aaacaaaagt      900
aagaccaccg cacagcaagc ggccgctgat cttcagacct ggaggaggag atatgaggga      960
caattggaga agtgaattat ataaatataa agtagtaaaa attgaaccat taggagtagc     1020
acccaccaag gcaaagagaa gagtggtgca gagagaaaaa agagcagtgg gaataggagc     1080
tttgttcctt gggttcttgg agcagcagg  aagcactatg ggcgcagcgt caatgacgct     1140
gacggtacag gccagacaat tattgtctgg tatagtgcag cagcagaaca atttgctgag     1200
ggctattgag gcgcaacagc atctgttgca actcacagtc tggggcatca agcagctcca     1260
ggcaagaatc ctggctgtgg aaagatacct aaaggatcaa cagctcctgg ggatttgggg     1320
ttgctctgga aaactcattt gcaccactgc tgtgccttgg aatgctagtt ggagtaataa     1380
atctctggaa cagatttgga atcacacgac ctggatggag tgggacagag aaattaacaa     1440
ttacacaagc ttaatacact ccttaattga agaatcgcaa aaccagcaag aaaagaatga     1500
acaagaatta ttggaattag ataaatgggc aagtttgtgg aattggttta acataacaaa     1560
ttggctgtgg tatataaaat tattcataat gatagtagga ggcttggtag gtttaagaat     1620 agttttgct  gtactttcta tagtgaatag agttaggcag ggatattcac cattatcgtt     1680
tcagacccac ctcccaaccc cgaggggacc cgacaggccc gaaggaatag aagaagaagg     1740
tggagagaga gacagagaca gatccattcg attagtgaac ggatctcgac ggtatcgcta     1800
gcttttaaaa gaaaaggggg gattgggggg tacagtgcag gggaagaat agtagacata     1860 atagcaacag acatacaaac taaagaatta caaaaacaaa ttacaaaaat tcaaaatttt     1920
actagtgatt atcggatcaa ctttgtatag aaaagttgga attcgaacgc tgacgtcatc     1980
aacccgctcc aaggaatcgc gggcccagtg tcactaggcg ggaacaccca gcgcgcgtgc     2040
gccctggcag aagatggct  gtgagggaca ggggagtggc gccctgcaat atttgcatgt     2100
cgctatgtgt tctgggaaat caccataaac gtgaaatgtc tttggatttg ggaatcttat     2160
aagttctgta tgagaccacc gggtccatac agtcagtatc aattctcgag aattgatact     2220
gactgtatgg attttggat  cccaagtttg tacaaaaaag caggctggct ccggtgcccg     2280
tcagtgggca gagcgcacat cgcccacagt ccccgagaag ttgggggag  gggtcggcaa     2340 ttgaaccggt gcctagagaa ggtggcgcgg ggtaaactgg gaaagtgatg tcgtgtactg     2400
gctccgcctt tttcccgagg gtgggggaga accgtatata agtgcagtag tcgccgtgaa     2460
cgttcttttt cgcaacgggt ttgccgccag aacacaggta agtgccgtgt gtggttcccg     2520
cgggcctggc ctctttacgg gttatggccc ttgcgtgcct tgaattactt ccacctggct     2580
gcagtacgtg attcttgatc ccgagcttcg ggttggaagt gggtgggaga gttcgaggcc     2640
ttgcgcttaa ggagcccctt cgcctcgtgc ttgagttgag gcctggcctg ggcgctgggg     2700
ccgccgcgtg cgaatctggt ggcaccttcg cgcctgtctc gctgctttcg ataagtctct     2760
agccatttaa aatttttgat gacctgctgc gacgcttttt ttctggcaag atagtcttgt     2820
aaatgcgggc caagatctgc acactggtat ttcggttttt ggggccgcgg gcggcgacgg     2880
ggcccgtgcg tcccagcgca catgttcggc gaggcggggc ctgcgagcgc ggccaccgag     2940
aatcggacgg gggtagtctc aagctggccg gcctgctctg gtgcctggtc tcgcgccgcc     3000
gtgtatcgcc ccgccctggg cggcaaggct ggcccggtcg gcaccagttg cgtgagcgga     3060
aagatggccg cttcccggcc ctgctgcagg gagctcaaaa tggaggacgc ggcgctcggg     3120
```

| | |
|---|---|
| agagcgggcg ggtgagtcac ccacacaaag gaaaagggcc tttccgtcct cagccgtcgc | 3180 |
| ttcatgtgac tccacggagt accgggcgcc gtccaggcac ctcgattagt tctcgagctt | 3240 |
| ttggagtacg tcgtctttag gttgggggga ggggttttat gcgatggagt ttccccacac | 3300 |
| tgagtgggtg gagactgaag ttaggccagc ttggcacttg atgtaattct ccttggaatt | 3360 |
| tgccctttt gagtttggat cttggttcat tctcaagcct cagacagtgg ttcaaagttt | 3420 |
| ttttcttcca tttcaggtgt cgtgagccac catgtcatcc tcaggcacgc cagacttacc | 3480 |
| tgtcctactc accgatttga agattcaata tactaagatc ttcataaaca atgaatggca | 3540 |
| tgattcagtg agtggcaaga aatttcctgt ctttaatcct gcaactgagg aggagctctg | 3600 |
| ccaggtagaa gaaggagata aggaggatgt tgacaaggca gtgaaggccg caagacaggc | 3660 |
| ttttcagatt ggatccccgt ggcgtactat ggatgcttcc gagaggggc gactattata | 3720 |
| caagttggct gatttaatcg aaagagatcg tctgctgctg gcgacaatgg agtcaatgaa | 3780 |
| tggtggaaaa ctctattcca atgcatatct gaatgattta gcaggctgca tcaaaacatt | 3840 |
| gcgctactgt gcaggttggg ctgacaagat ccagggccgt acaataccaa ttgatggaaa | 3900 |
| tttttttaca tatacaagac atgaacctat tggtgtatgt ggccaaatca ttccttggaa | 3960 |
| tttcccgttg gttatgctca tttggaagat agggcctgca ctgagctgtg gaaacacagt | 4020 |
| ggttgtcaaa ccagcagagc aaactcctct cactgctctc cacgtggcat ctttaataaa | 4080 |
| agaggcaggg tttcctcctg gagtagtgaa tattgttcct ggttatgggc ctacagcagg | 4140 |
| ggcagccatt tcttctcaca tggatataga caaagtagcc ttcacaggat caacagaggt | 4200 |
| tggcaagttg atcaaagaag ctgccgggaa aagcaatctg aagagggtga ccctggagct | 4260 |
| tggaggaaag agcccttgca ttgtgttagc tgatgccgac ttggacaatg ctgttgaatt | 4320 |
| tgcacaccat ggggtattct accaccaggg ccagtgttgt atagccgcat ccaggatttt | 4380 |
| tgtggaagaa tcaatttatg atgagtttgt tcgaaggagt gttgagcggg ctaagaagta | 4440 |
| tatccttgga aatcctctga ccccaggagt cactcaaggc cctcagattg acaaggaaca | 4500 |
| atatgataaa atacttgacc tcattgagag tgggaagaaa gaaggggcca aactggaatg | 4560 |
| tggaggaggc ccgtggggga ataaaggcta ctttgtccag cccacagtgt tctctaatgt | 4620 |
| tacagatgag atgcgcattg ccaaagagga gatttttgga ccagtgcagc aaatcatgaa | 4680 |
| gtttaaatct ttagatgacg tgatcaaaag agcaaacaat actttctatg gcttatcagc | 4740 |
| aggagtgttt accaaagaca ttgataaagc cataacaatc tcctctgctc tgcaggcagg | 4800 |
| aacagtgtgt gtgaattgct atggcgtggt aagtgcccag tgccccttg gtggattcaa | 4860 |
| gatgtctgga aatggaagag aactgggaga gtacggttc catgaatata cagaggtcaa | 4920 |
| aacagtcaca gtgaaaatct ctcagaagaa ctcaggaagc ggagagggca ggggaagtct | 4980 |
| tctaacatgc ggggacgtgg aggaaaatcc cggccccatg ggcgccggcg ccaccggcag | 5040 |
| agccatggac ggcccagac tgctgctgct gctgctgctg ggcgtgagcc tgggcggcgc | 5100 |
| cagaagctgg atggagtggg acagagagat caacaactac accagcctga tccacagcct | 5160 |
| gatcgaggag agccagaacc agcaggagaa gaacagcag gagctgctgg agctggacaa | 5220 |
| gtgggccagc ctgtggaact ggttcagaag cgagagaaag tgctgcgtgg agtgcccccc | 5280 |
| ctgccccgcc cccccgtgg ccggcccct gatcgccctg gtgaccagcg gcgccctgct | 5340 |
| ggccgtgctg ggcatcaccg gctacttcct gatgaacaga agaagctgga gccccaccgg | 5400 |
| cgagagactg gagctggagc cctaaaccca gctttcttgt acaaagtggt gataatcgaa | 5460 |

| | |
|---|---|
| ttccgataat caacctctgg attacaaaat ttgtgaaaga ttgactggta ttcttaacta | 5520 |
| tgttgctcct tttacgctat gtggatacgc tgctttaatg cctttgtatc atgctattgc | 5580 |
| ttcccgtatg gctttcattt tctcctcctt gtataaatcc tggttgctgt ctctttatga | 5640 |
| ggagttgtgg cccgttgtca ggcaacgtgg cgtggtgtgc actgtgtttg ctgacgcaac | 5700 |
| ccccactggt tggggcattg ccaccacctg tcagctcctt tccgggactt tcgctttccc | 5760 |
| cctccctatt gccacggcgg aactcatcgc cgcctgcctt gcccgctgct ggacagggct | 5820 |
| tcggctgttg ggcactgaca attccgtggt gttgtcgggg aagctgacgt cctttccatg | 5880 |
| gctgctcgcc tgtgttgcca cctggattct gcgcgggacg tccttctgct acgtcccttc | 5940 |
| ggccctcaat ccagcggacc ttccttcccg cggcctgctg ccggctctgc ggcctcttcc | 6000 |
| gcgtcttcgc cttcgccctc agacgagtcg gatctccctt gggccgcct ccccgcatcg | 6060 |
| ggaattcccg cggttcgctt taagaccaat gacttacaag gcagctgtag atcttagcca | 6120 |
| cttttaaaa gaaagggggg gactggaagg gctaattcac tcccaacgaa gacaagatct | 6180 |
| gcttttgct tgtactgggt ctctctggtt agaccagatc tgagcctggg agctctctgg | 6240 |
| ctaactaggg aacccactgc ttaagcctca ataaagcttg ccttgagtgc ttcaagtagt | 6300 |
| gtgtgcccgt ctgttgtgtg actctggtaa ctagagatcc ctcagaccct tttagtcagt | 6360 |
| gtggaaaatc tctagcagta gtagttcatg tcatcttatt attcagtatt tataacttgc | 6420 |
| aaagaaatga atatcagaga gtgagaggaa cttgtttatt gcagcttata atggttacaa | 6480 |
| ataaagcaat agcatcacaa atttcacaaa taaagcattt ttttcactgc attctagttg | 6540 |
| tggtttgtcc aaactcatca atgtatctta tcatgtctgg ctctagctat cccgccccta | 6600 |
| actccgccca tcccgcccct aactccgccc agttccgccc attctccgcc ccatggctga | 6660 |
| ctaattttt ttatttatgc agaggccgag gccgcctcgg cctctgagct attccagaag | 6720 |
| tagtgaggag gcttttttgg aggcctaggg acgtacccaa ttcgccctat agtgagtcgt | 6780 |
| attacgcgcg ctcactggcc gtcgttttac aacgtcgtga ctgggaaaac cctggcgtta | 6840 |
| cccaacttaa tcgccttgca gcacatcccc ctttcgccag ctggcgtaat agcgaagagg | 6900 |
| cccgcaccga tcgcccttcc caacagttgc gcagcctgaa tggcgaatgg gacgcgccct | 6960 |
| gtagcggcgc attaagcgcg gcgggtgtgg tggttacgcg cagcgtgacc gctacacttg | 7020 |
| ccagcgccct agcgcccgct cctttcgctt tcttcccttc ctttctcgcc acgttcgccg | 7080 |
| gctttccccg tcaagctcta aatcgggggc tccctttagg gttccgattt agtgctttac | 7140 |
| ggcacctcga ccccaaaaaa cttgattagg gtgatggttc acgtagtggg ccatcgccct | 7200 |
| gatagacggt ttttcgccct ttgacgttgg agtccacgtt ctttaatagt ggactcttgt | 7260 |
| tccaaactgg aacaacactc aaccctatct cggtctattc ttttgattta agggattt | 7320 |
| tgccgatttc ggcctattgg ttaaaaaatg agctgattta acaaaaattt aacgcgaatt | 7380 |
| ttaacaaaat attaacgctt acaatttagg tggcactttt cggggaaatg tgcgcggaac | 7440 |
| ccctatttgt ttatttttct aaatacattc aaatatgtat ccgctcatga gacaataacc | 7500 |
| ctgataaatg cttcaataat attgaaaaag gaagagtatg agtattcaac atttccgtgt | 7560 |
| cgcccttatt ccctttttg cggcattttg ccttcctgtt tttgctcacc cagaaacgct | 7620 |
| ggtgaaagta aaagatgctg aagatcagtt gggtgcacga gtgggttaca tcgaactgga | 7680 |
| tctcaacagc ggtaagatcc ttgagagttt tcgccccgaa gaacgttttc caatgatgag | 7740 |
| cacttttaaa gttctgctat gtggcgcggt attatcccgt attgacgccg ggcaagagca | 7800 |
| actcggtcgc cgcatacact attctcagaa tgacttggtt gagtactcac cagtcacaga | 7860 |

```
aaagcatctt acggatggca tgacagtaag agaattatgc agtgctgcca taaccatgag   7920
tgataacact gcggccaact tacttctgac aacgatcgga ggaccgaagg agctaaccgc   7980
ttttttgcac aacatggggg atcatgtaac tcgccttgat cgttgggaac cggagctgaa   8040
tgaagccata ccaaacgacg agcgtgacac cacgatgcct gtagcaatgg caacaacgtt   8100
gcgcaaacta ttaactggcg aactacttac tctagcttcc cggcaacaat taatagactg   8160
gatggaggcg gataaagttg caggaccact tctgcgctcg gcccttccgg ctggctggtt   8220
tattgctgat aaatctggag ccggtgagcg tgggtctcgc ggtatcattg cagcactggg   8280
gccagatggt aagccctccc gtatcgtagt tatctacacg acggggagtc aggcaactat   8340
ggatgaacga atagacaga tcgctgagat aggtgcctca ctgattaagc attggtaact   8400
gtcagaccaa gtttactcat atactttta gattgattta aaacttcatt tttaatttaa   8460
aaggatctag gtgaagatcc ttttgataa tctcatgacc aaaatccctt aacgtgagtt   8520
ttcgttccac tgagcgtcag acccgtaga aagatcaaa ggatcttctt gagatccttt   8580
ttttctgcgc gtaatctgct gcttgcaaac aaaaaaacca ccgctaccag cggtggtttg   8640
tttgccggat caagagctac caactctttt tccgaaggta actggcttca gcagagcgca   8700
gataccaaat actgttcttc tagtgtagcc gtagttaggc caccacttca gaactctgt   8760 agcaccgcct acatacctcg ctctgctaat cctgttacca gtggctgctg ccagtggcga   8820
taagtcgtgt cttaccgggt tggactcaag acgatagtta ccggataagg cgcagcggtc   8880
gggctgaacg gggggttcgt gcacacagcc cagcttggag cgaacgacct acaccgaact   8940
gagataccta cagcgtgagc tatgagaaag cgccacgctt cccgaagaga aaaggcgga   9000 caggtatccg gtaagcggca gggtcggaac aggagagcgc acgagggagc ttccaggggg   9060
aaacgcctgg tatctttata gtcctgtcgg gtttcgccac ctctgacttg agcgtcgatt   9120
tttgtgatgc tcgtcagggg ggcggagcct atggaaaaac gccagcaacg cggccttttt   9180
acggttcctg gccttttgct ggccttttgc tcacatgttc tttcctgcgt tatcccctga   9240
ttctgtggat aaccgtatta ccgcctttga gtgagctgat accgctcgcc gcagccgaac   9300
gaccgagcgc agcgagtcag tgagcgagga agcggaagag cgcccaatac gcaaaccgcc   9360
tctccccgcg cgttggccga ttcattaatg cagctggcac gacaggtttc ccgactggaa   9420
agcgggcagt gagcgcaacg caattaatgt gagttagctc actcattagg caccccaggc   9480
tttacacttt atgcttccgg ctcgtatgtt gtgtggaatt gtgagcggat aacaatttca   9540
cacaggaaac agctatgacc atgattacgc caagcgcgca attaaccctc actaaggga   9600 acaaaagctg gagctgcaag ctt                                          9623
```

<210> SEQ ID NO 5
<211> LENGTH: 8059
<212> TYPE: DNA
<213> ORGANISM: Artificial Sequence
<220> FEATURE:
<223> OTHER INFORMATION: pLV: maC46:shCCR5

<400> SEQUENCE: 5

```
aatgtagtct tatgcaatac tcttgtagtc ttgcaacatg gtaacgatga gttagcaaca     60
tgccttacaa ggagagaaaa agcaccgtgc atgccgattg gtggaagtaa ggtggtacga    120
tcgtgcctta ttaggaaggc aacagacggg tctgacatgg attggacgaa ccactgaatt    180
gccgcattgc agagatattg tatttaagtg cctagctcga tacataaacg ggtctctctg    240
```

```
                                              -continued gttagaccag atctgagcct gggagctctc tggctaacta gggaacccac tgcttaagcc     300
tcaataaagc ttgccttgag tgcttcaagt agtgtgtgcc cgtctgttgt gtgactctgg     360
taactagaga tccctcagac cctttagtc agtgtggaaa atctctagca gtggcgcccg      420 aacaggggact tgaaagcgaa agggaaacca gaggagctct ctcgacgcag gactcggctt    480
gctgaagcgc gcacggcaag aggcgagggg cggcgactgg tgagtacgcc aaaaattttg     540
actagcggag gctagaagga gagagatggg tgcgagagcg tcagtattaa gcgggggaga    600
attagatcgc gatgggaaaa aattcggtta aggccagggg gaaagaaaaa atataaatta    660
aaacatatag tatgggcaag cagggagcta gaacgattcg cagttaatcc tggcctgtta    720
gaaacatcag aaggctgtag acaaatactg ggacagctac aaccatccct tcagacagga    780
tcagaagaac ttagatcatt atataataca gtagcaaccc tctattgtgt gcatcaaagg    840
atagagataa aagacaccaa ggaagcttta gacaagatag aggaagagca aaacaaaagt    900
aagaccaccg cacagcaagc ggccgctgat cttcagacct ggaggaggag atatgaggga    960
caattggaga agtgaattat ataaatataa agtagtaaaa attgaaccat taggagtagc    1020
acccaccaag gcaaagagaa gagtggtgca gagagaaaaa agagcagtgg gaataggagc    1080
tttgttcctt gggttcttgg gagcagcagg aagcactatg ggcgcagcgt caatgacgct    1140
gacggtacag gccagacaat tattgtctgg tatagtgcag cagcagaaca atttgctgag    1200
ggctattgag gcgcaacagc atctgttgca actcacagtc tggggcatca agcagctcca    1260
ggcaagaatc ctggctgtgg aaagatacct aaaggatcaa cagctcctgg ggatttgggg    1320
ttgctctgga aaactcattt gcaccactgc tgtgccttgg aatgctagtt ggagtaataa    1380
atctctggaa cagatttgga atcacacgac ctggatggag tgggacagag aaattaacaa    1440
ttacacaagc ttaatacact ccttaattga agaatcgcaa aaccagcaag aaaagaatga    1500
acaagaatta ttggaattag ataaatgggc aagtttgtgg aattggttta acataacaaa    1560
ttggctgtgg tatataaaat tattcataat gatagtagga ggcttggtag gtttaagaat    1620 agttttgct gtactttcta tagtgaatag agttaggcag ggatattcac cattatcgtt    1680
tcagacccac ctcccaaccc cgaggggacc cgacaggccc gaaggaatag aagaagaagg    1740
tggagagaga gacagagaca gatccattcg attagtgaac ggatctcgac ggtatcgcta    1800
gcttttaaaa gaaagggggg gattgggggg tacagtgcag gggaagaat agtagacata    1860 atagcaacag acatacaaac taaagaatta caaaaacaaa ttacaaaaat tcaaaatttt    1920
actagtgatt atcggatcaa cttttgtatag aaaagttgga attcgaacgc tgacgtcatc    1980
aacccgctcc aaggaatcgc gggcccagtg tcactaggcg gaacaccca gcgcgcgtgc    2040 gccctggcag gaagatggct gtgagggaca ggggagtggc gccctgcaat atttgcatgt    2100
cgctatgtgt tctgggaaat caccataaac gtgaaatgtc tttggatttg gaatcttat    2160 aagttctgta tgagaccacc gggtccatac agtcagtatc aattctcgag aattgatact    2220
gactgtatgg atttttggat cccaagtttg tacaaaaaag caggctggct ccggtgcccg    2280
tcagtgggca gagcgcacat cgcccacagt ccccgagaag ttgggggggag gggtcggcaa    2340 ttgaaccggt gcctagagaa ggtggcgcgg ggtaaactgg gaaagtgatg tcgtgtactg    2400
gctccgcctt tttcccgagg gtgggggaga accgtatata agtgcagtag tcgccgtgaa    2460
cgttcttttt cgcaacgggt ttgccgccag aacacaggta agtgccgtgt gtggttcccg    2520
cgggcctggc ctctttacgg gttatggccc ttgcgtgcct tgaattactt ccacctggct    2580
gcagtacgtg attcttgatc ccgagcttcg ggttggaagt gggtgggaga gttcgaggcc    2640
```

```
ttgcgcttaa ggagcccctt cgcctcgtgc ttgagttgag gcctggcctg ggcgctgggg    2700
ccgccgcgtg cgaatctggt ggcaccttcg cgcctgtctc gctgctttcg ataagtctct    2760
agccatttaa aattttttgat gacctgctgc gacgcttttt ttctggcaag atagtcttgt   2820
aaatgcgggc caagatctgc acactggtat ttcggttttt ggggccgcgg gcggcgacgg    2880
ggcccgtgcg tcccagcgca catgttcggc gaggcggggc ctgcgagcgc ggccaccgag    2940
aatcggacgg gggtagtctc aagctggccg gcctgctctg gtgcctggtc tcgcgccgcc    3000
gtgtatcgcc ccgccctggg cggcaaggct ggcccggtcg gcaccagttg cgtgagcgga    3060
aagatggccg cttcccggcc ctgctgcagg gagctcaaaa tggaggacgc ggcgctcggg    3120
agagcgggcg ggtgagtcac ccacacaaag gaaaagggcc tttccgtcct cagccgtcgc    3180
ttcatgtgac tccacggagt accgggcgcc gtccaggcac ctcgattagt tctcgagctt    3240
ttggagtacg tcgtctttag gttgggggga ggggtttat gcgatggagt ttccccacac     3300
tgagtgggtg gagactgaag ttaggccagc ttggcacttg atgtaattct ccttggaatt    3360 tgccctttt gagtttggat cttggttcat tctcaagcct cagacagtgg ttcaaagttt     3420
ttttcttcca tttcaggtgt cgtgagccac catgggcgcc ggcgccaccg gcagagccat    3480
ggacggcccc agactgctgc tgctgctgct gctgggcgtg agcctgggcg cgccagaag     3540 ctggatggag tgggacagag agatcaacaa ctacaccagc ctgatccaca gcctgatcga    3600
ggagagccag aaccagcagg agaagaacga gcaggagctg ctggagctgg acaagtgggc    3660
cagcctgtgg aactggttca gaagcgagag aaagtgctgc gtggagtgcc cccctgccc    3720 cgccccccc gtggccggcc ccctgatcgc cctggtgacc agcggcgccc tgctggccgt     3780
gctgggcatc accggctact tcctgatgaa cagaagaagc tggagcccca ccggcgagag    3840
actggagctg gagccctaaa acccagcttt tcttgtacaa agtggtgata atcgaattcc    3900
gataatcaac ctctggatta caaaatttgt gaaagattga ctggtattct taactatgtt    3960
gctcctttta cgctatgtgg atacgctgct ttaatgcctt tgtatcatgc tattgcttcc    4020
cgtatggctt tcattttctc ctccttgtat aaatcctggt tgctgtctct ttatgaggag    4080
ttgtggcccg ttgtcaggca acgtggcgtg gtgtgcactg tgtttgctga cgcaaccccc    4140
actggttggg gcattgccac cacctgtcag ctcctttccg ggactttcgc ttttcccctc    4200
cctattgcca cggcggaact catcgccgcc tgccttgccc gctgctggac aggggctcgg    4260
ctgttgggca ctgacaattc cgtggtgttg tcggggaagc tgacgtcctt tccatggctg    4320
ctcgcctgtg ttgccacctg gattctgcgc gggacgtcct tctgctacgt cccttcggcc    4380
ctcaatccag cggaccttcc ttcccgcggc ctgctgccgg ctctgcggcc tcttccgcgt    4440
cttcgccttc gccctcagac gagtcggatc tccctttggg ccgcctcccc gcatcgggaa    4500
ttcccgcggt tcgctttaag accaatgact acaaggcag ctgtagatct tagccacttt     4560
ttaaaagaaa aggggggact ggaagggcta attcactccc aacgaagaca agatctgctt    4620
tttgcttgta ctgggtctct ctggttagac cagatctgag cctgggagct ctctggctaa    4680
ctagggaacc cactgcttaa gcctcaataa agcttgcctt gagtgcttca agtagtgtgt    4740
gcccgtctgt tgtgtgactc tggtaactag agatccctca gacccttta gtcagtgtgg     4800 aaaatctcta gcagtagtag ttcatgtcat cttattattc agtatttata acttgcaaag    4860
aaatgaatat cagagagtga gaggaacttg tttattgcag cttataatgg ttacaaataa    4920
agcaatagca tcacaaattt cacaaataaa gcatttttt cactgcattc tagttgtggt      4980
```

```
ttgtccaaac tcatcaatgt atcttatcat gtctggctct agctatcccg cccctaactc    5040
cgcccatccc gccctaact ccgcccagtt ccgcccattc tccgcccat ggctgactaa     5100 tttttttat ttatgcagag gccgaggccg cctcggcctc tgagctattc cagaagtagt    5160
gaggaggctt ttttggaggc ctagggacgt acccaattcg ccctatagtg agtcgtatta    5220
cgcgcgctca ctggccgtcg ttttacaacg tcgtgactgg gaaaaccctg gcgttaccca    5280
acttaatcgc cttgcagcac atccccettt cgccagctgg cgtaatagcg aagaggcccg    5340
caccgatcgc ccttcccaac agttgcgcag cctgaatggc gaatgggacg cgccctgtag    5400
cggcgcatta gcgcggcgg gtgtggtggt tacgcgcagc gtgaccgcta cacttgccag    5460
cgccctagcg cccgctcctt tcgctttctt cccttccttt ctcgccacgt tcgccggctt    5520
tccccgtcaa gctctaaatc gggggctccc tttagggttc cgatttagtg ctttacggca    5580
cctcgacccc aaaaaacttg attagggtga tggttcacgt agtgggccat cgccctgata    5640
gacggttttt cgccctttga cgttggagtc cacgttcttt aatagtggac tcttgttcca    5700
aactggaaca acactcaacc ctatctcggt ctattcttt gatttataag ggattttgcc    5760
gatttcggcc tattggttaa aaaatgagct gatttaacaa aaatttaacg cgaattttaa    5820
caaaatatta acgcttacaa tttaggtggc actttcggg gaaatgtgcg cggaacccct    5880
atttgtttat ttttctaaat acattcaaat atgtatccgc tcatgagaca ataaccctga    5940
taaatgcttc aataatattg aaaaaggaag agtatgagta ttcaacattt ccgtgtcgcc    6000
cttattccct ttttgcggc attttgcctt cctgttttg ctcacccaga acgctggtg     6060 aaagtaaaag atgctgaaga tcagttgggt gcacgagtgg gttacatcga actggatctc    6120
aacagcggta agatccttga gagttttcgc cccgaagaac gttttccaat gatgagcact    6180
tttaaagttc tgctatgtgg cgcggtatta tcccgtattg acgccgggca agagcaactc    6240
ggtcgccgca tacactattc tcagaatgac ttggttgagt actcaccagt cacagaaaag    6300
catcttacgg atggcatgac agtaagagaa ttatgcagtg ctgccataac catgagtgat    6360
aacactgcgg ccaacttact tctgacaacg atcggaggac cgaaggagct aaccgctttt    6420
ttgcacaaca tgggggatca tgtaactcgc cttgatcgtt gggaaccgga gctgaatgaa    6480
gccataccaa acgacgagcg tgacaccacg atgcctgtag caatggcaac aacgttgcgc    6540
aaactattaa ctggcgaact acttactcta gcttcccggc aacaattaat agactggatg    6600
gaggcggata aagttgcagg accacttctg cgctcggccc ttccggctgg ctggtttatt    6660
gctgataaat ctggagccgg tgagcgtggg tctcgcggta tcattgcagc actggggcca    6720
gatggtaagc cctcccgtat cgtagttatc tacacgacgg ggagtcaggc aactatggat    6780
gaacgaaata gacagatcgc tgagataggt gcctcactga ttaagcattg gtaactgtca    6840
gaccaagttt actcatatat actttagatt gatttaaaac ttcattttta atttaaaagg    6900
atctaggtga agatcctttt tgataatctc atgaccaaaa tcccttaacg tgagttttcg    6960
ttccactgag cgtcagaccc cgtagaaaag atcaaaggat cttcttgaga tcctttttt     7020 ctgcgcgtaa tctgctgctt gcaaacaaaa aaaccaccgc taccagcggt ggtttgtttg    7080
ccggatcaag agctaccaac tcttttccg aaggtaactg gcttcagcag agcgcagata    7140
ccaaatactg ttcttctagt gtagccgtag ttaggccacc acttcaagaa ctctgtagca    7200
ccgcctacat acctcgctct gctaatcctg ttaccagtgg ctgctgccag tggcgataag    7260
tcgtgtctta ccgggttgga ctcaagacga tagttaccgg ataaggcgca gcggtcgggc    7320
tgaacggggg gttcgtgcac acagcccagc ttggagcgaa cgacctacac cgaactgaga    7380
```

```
tacctacagc gtgagctatg agaaagcgcc acgcttcccg aagagagaaa ggcggacagg    7440
tatccggtaa gcggcagggt cggaacagga gagcgcacga gggagcttcc aggggggaaac   7500 gcctggtatc tttatagtcc tgtcgggttt cgccacctct gacttgagcg tcgattttg    7560 tgatgctcgt caggggggcg gagcctatgg aaaaacgcca gcaacgcggc cttttacgg    7620 ttcctggcct tttgctggcc ttttgctcac atgttctttc ctgcgttatc ccctgattct    7680
gtggataacc gtattaccgc ctttgagtga gctgataccg ctcgccgcag ccgaacgacc    7740
gagcgcagcg agtcagtgag cgaggaagcg gaagagcgcc caatacgcaa accgcctctc    7800
cccgcgcgtt ggccgattca ttaatgcagc tggcacgaca gtttcccga ctggaaagcg    7860 ggcagtgagc gcaacgcaat taatgtgagt tagctcactc attaggcacc ccaggcttta    7920
cactttatgc ttccggctcg tatgttgtgt ggaattgtga gcggataaca atttcacaca    7980
ggaaacagct atgaccatga ttacgccaag cgcgcaatta accctcacta agggaacaa    8040 aagctggagc tgcaagctt                                                8059

<210> SEQ ID NO 6
<211> LENGTH: 21
<212> TYPE: DNA
<213> ORGANISM: Artificial Sequence
<220> FEATURE:
<223> OTHER INFORMATION: hCCR5 shRNA sense

<400> SEQUENCE: 6
actcttgaca gggctctatt t                                              21

<210> SEQ ID NO 7
<211> LENGTH: 21
<212> TYPE: DNA
<213> ORGANISM: Artificial Sequence
<220> FEATURE:
<223> OTHER INFORMATION: hCCR5 shRNA antisense

<400> SEQUENCE: 7
aaatagagcc ctgtcaagag t                                              21

<210> SEQ ID NO 8
<211> LENGTH: 1096
<212> TYPE: DNA
<213> ORGANISM: Artificial Sequence
<220> FEATURE:
<223> OTHER INFORMATION: Human CD4 Promoter:-1076 to +20

<400> SEQUENCE: 8
aagacaggtt ctcactctgt cactcaggct agagtgcagt ggtgcaatca cggttcactg     60
cagcctcaac ttcctgggct caagcgatcc cccacctcg gcctcctaaa atgctgggat    120
tataggcatg agccaccact cccagcccca cttttttcag actggaaaac gcacactcac   180
atgtgcatct ttaaatgatc acttgggctg tggtatggag aatggcgacc agtgaggagg   240
caggagctgt tgtccgagca agggatgata ttggcatctt ggattggcat ggtggcagta   300
gtggtagtgc agagtgactt gggtagattt tggagccatt tagaaggtaa catccacagg   360
aactggtaaa taaatacgtg ggagaagttg ggtgaagggg gtgtcaaaga ttacacccaa   420
tttattttgc ttgggcaagt tggtggatgg tgagcccctc actgagtgag aagcctggag   480
aagcaggttt ggagggtggt agtatgcagg tggtatgcat agttgggat gtgtgttgag   540 tttgctatgt ccggtgagct tcccagtgga gatgtccaat gggcagacgg atactcacat   600
```

```
agagagttca tggtagattc gggctagagg aaagcacctg aggcctggcc agagacgcct    660
agaggaacag agcctggtta acagtcactc ctggtgtctc agatattctc tgctcagccc    720
acgccctctc ttccacactg gccacctat aaagcctcca cagataccc tggggcaccc      780 actggacaca tgccctcagg gccccagagc aaggagctgt tgtgggctt accactgctg     840 ttcccatatg cccccaactg cctcccactt cttcccac agcctggtca gacatggcgc      900
taccactaat ggaatctttc ttgccatctt tttcttgccg cttaacagtg gcagtgacag    960
tttgactcct gatttaagcc tgattctgct taactttc ccttgactt ggcattttca     1020 ctttgacatg ttccctgaga gcctggggg tggggaaccc agctccagct ggtgacgttt    1080
ggggccggcc caggcc                                                   1096
```

<210> SEQ ID NO 9
<211> LENGTH: 320
<212> TYPE: DNA
<213> ORGANISM: Artificial Sequence
<220> FEATURE:
<223> OTHER INFORMATION: Human CD3E

<400> SEQUENCE: 9

```
aaggtacgga agaggacggt ggcggtggaa gccgggcttg agatgggac acagatttcc     60 acaagctgcc tggaaaagct gcgagccagg gctggggaag tgaaggaggg aggtgtctca   120
agcaggcaca cccccaccct gaggcagccg cctgcagcca gaggcgggct gtggttaagc   180
agcgcaggat gtgggctgca ctgctaagcg tggcttctgg gagtgagggt gggagaggta   240
cagcggcagc tggcggaggc ccgtgtgaga gcgctttgtt ctcagtctcc cacagcacac   300
tctgcttgca gaggggatc                                                320
```

<210> SEQ ID NO 10
<211> LENGTH: 501
<212> TYPE: PRT
<213> ORGANISM: Artificial Sequence
<220> FEATURE:
<223> OTHER INFORMATION: hALDH1 protein

<400> SEQUENCE: 10

```
Met Ser Ser Ser Gly Thr Pro Asp Leu Pro Val Leu Leu Thr Asp Leu
1               5                   10                  15

Lys Ile Gln Tyr Thr Lys Ile Phe Ile Asn Asn Glu Trp His Asp Ser
            20                  25                  30

Val Ser Gly Lys Lys Phe Pro Val Phe Asn Pro Ala Thr Glu Glu Glu
        35                  40                  45

Leu Cys Gln Val Glu Glu Gly Asp Lys Glu Asp Val Asp Lys Ala Val
    50                  55                  60

Lys Ala Ala Arg Gln Ala Phe Gln Ile Gly Ser Pro Trp Arg Thr Met
65                  70                  75                  80

Asp Ala Ser Glu Arg Gly Arg Leu Leu Tyr Lys Leu Ala Asp Leu Ile
                85                  90                  95

Glu Arg Asp Arg Leu Leu Leu Ala Thr Met Glu Ser Met Asn Gly Gly
            100                 105                 110

Lys Leu Tyr Ser Asn Ala Tyr Leu Asn Asp Leu Ala Gly Cys Ile Lys
        115                 120                 125

Thr Leu Arg Tyr Cys Ala Gly Trp Ala Asp Lys Ile Gln Gly Arg Thr
    130                 135                 140

Ile Pro Ile Asp Gly Asn Phe Phe Thr Tyr Thr Arg His Glu Pro Ile
145                 150                 155                 160
```

```
Gly Val Cys Gly Gln Ile Ile Pro Trp Asn Phe Pro Leu Val Met Leu
                165                 170                 175

Ile Trp Lys Ile Gly Pro Ala Leu Ser Cys Gly Asn Thr Val Val Val
            180                 185                 190

Lys Pro Ala Glu Gln Thr Pro Leu Thr Ala Leu His Val Ala Ser Leu
        195                 200                 205

Ile Lys Glu Ala Gly Phe Pro Pro Gly Val Val Asn Ile Val Pro Gly
    210                 215                 220

Tyr Gly Pro Thr Ala Gly Ala Ala Ile Ser Ser His Met Asp Ile Asp
225                 230                 235                 240

Lys Val Ala Phe Thr Gly Ser Thr Glu Val Gly Lys Leu Ile Lys Glu
                245                 250                 255

Ala Ala Gly Lys Ser Asn Leu Lys Arg Val Thr Leu Glu Leu Gly Gly
            260                 265                 270

Lys Ser Pro Cys Ile Val Leu Ala Asp Ala Asp Leu Asp Asn Ala Val
        275                 280                 285

Glu Phe Ala His His Gly Val Phe Tyr His Gln Gly Gln Cys Cys Ile
    290                 295                 300

Ala Ala Ser Arg Ile Phe Val Glu Glu Ser Ile Tyr Asp Glu Phe Val
305                 310                 315                 320

Arg Arg Ser Val Glu Arg Ala Lys Lys Tyr Ile Leu Gly Asn Pro Leu
                325                 330                 335

Thr Pro Gly Val Thr Gln Gly Pro Gln Ile Asp Lys Glu Gln Tyr Asp
            340                 345                 350

Lys Ile Leu Asp Leu Ile Glu Ser Gly Lys Lys Glu Gly Ala Lys Leu
        355                 360                 365

Glu Cys Gly Gly Gly Pro Trp Gly Asn Lys Gly Tyr Phe Val Gln Pro
    370                 375                 380

Thr Val Phe Ser Asn Val Thr Asp Glu Met Arg Ile Ala Lys Glu Glu
385                 390                 395                 400

Ile Phe Gly Pro Val Gln Gln Ile Met Lys Phe Lys Ser Leu Asp Asp
                405                 410                 415

Val Ile Lys Arg Ala Asn Asn Thr Phe Tyr Gly Leu Ser Ala Gly Val
            420                 425                 430

Phe Thr Lys Asp Ile Asp Lys Ala Ile Thr Ile Ser Ser Ala Leu Gln
        435                 440                 445

Ala Gly Thr Val Trp Val Asn Cys Tyr Gly Val Val Ser Ala Gln Cys
    450                 455                 460

Pro Phe Gly Gly Phe Lys Met Ser Gly Asn Gly Arg Glu Leu Gly Glu
465                 470                 475                 480

Tyr Gly Phe His Glu Tyr Thr Glu Val Lys Thr Val Thr Val Lys Ile
                485                 490                 495

Ser Gln Lys Asn Ser
            500
```

<210> SEQ ID NO 11
<211> LENGTH: 135
<212> TYPE: PRT
<213> ORGANISM: Artificial Sequence
<220> FEATURE:
<223> OTHER INFORMATION: Membrane Anchored C46 Fusion Inhibitor Protein

<400> SEQUENCE: 11

```
Met Gly Ala Gly Ala Thr Gly Arg Ala Met Asp Gly Pro Arg Leu Leu
1               5                   10                  15
```

| | | | | | | | | | | | |
|---|---|---|---|---|---|---|---|---|---|---|---|
|Leu|Leu|Leu|Leu|Leu|Gly|Val|Ser|Leu|Gly|Gly|Ala|Arg|Ser|Trp|Met|
| | | |20| | | |25| | | |30| | | | |

Leu Leu Leu Leu Leu Gly Val Ser Leu Gly Gly Ala Arg Ser Trp Met
            20                  25              30

Glu Trp Asp Arg Glu Ile Asn Asn Tyr Thr Ser Leu Ile His Ser Leu
        35              40                  45

Ile Glu Glu Ser Gln Asn Gln Gln Glu Lys Asn Glu Gln Leu Leu
 50              55                  60

Glu Leu Asp Lys Trp Ala Ser Leu Trp Asn Trp Phe Arg Ser Glu Arg
 65              70                  75                  80

Lys Cys Cys Val Glu Cys Pro Pro Cys Pro Ala Pro Val Ala Gly
                85              90                  95

Pro Leu Ile Ala Leu Val Thr Ser Gly Ala Leu Leu Ala Val Leu Gly
            100                 105                 110

Ile Thr Gly Tyr Phe Leu Met Asn Arg Arg Ser Trp Ser Pro Thr Gly
            115                 120                 125

Glu Arg Leu Glu Leu Glu Pro
    130             135

<210> SEQ ID NO 12
<211> LENGTH: 540
<212> TYPE: DNA
<213> ORGANISM: Artificial Sequence
<220> FEATURE:
<223> OTHER INFORMATION: synthetic sequence

<400> SEQUENCE: 12

```
aggatgatgg tgatggggaa ctaaatgggg aaatatggaa ggtcacagga aaagttaaca      60
caagttagca aaaagttaac ataacacaaa aaggtcttgc aggaaaaaaa aaagaaaaga     120
aaagaaagaa aaagtctcca agaatggttt ggacagccaa aatgaatact tatagtcacg     180
tatacctgct cactcctgac gcttcactca cacacagcac aggatctggt gaggctatca     240
ctaaatgtgc cacattgtgg ttaagtttta cctgattaac gaaatgctca cacttctaaa     300
ctgaggtcct tacagtagat tccttttgca agattgttac tggcttacaa cttaaaaata     360
aaggaaaatc acaaggaaag aaaagtgggg aaaaaatcgg aggaaacttg cccctgccct     420
ggccaccggc aaggctgcca caaaggggtt aaaagttaag tggaagtgga gcttgaagaa     480
gtgggatggg gcctctccag gaaagctgaa cgaggcatct ggagcccgaa caaacctcca     540
```

<210> SEQ ID NO 13
<211> LENGTH: 321
<212> TYPE: DNA
<213> ORGANISM: Artificial Sequence
<220> FEATURE:
<223> OTHER INFORMATION: synthetic sequence

<400> SEQUENCE: 13

```
tgtttgaatg aggcttcagt actttacaga atcgttgcct gcacatcttg gaaacacttg      60
ctgggattac ttcgacttct aacccaaca gaaggctcga gaaggtatat tgctgttgac     120
agtgagcgca ctcttgacag ggctctattt tagtgaagcc acagatgtaa aatagagccc     180
tgtcaagagt ttgcctactg cctcggactt caaggggcta gaattcgagc aattatcttg     240
tttactaaaa ctgaatacct tgctatctct ttgatacatt tttacaaagc tgaattaaaa     300
tggtataaat taaatcactt t                                               321
```

<210> SEQ ID NO 14
<211> LENGTH: 132
<212> TYPE: DNA

```
<213> ORGANISM: Artificial Sequence
<220> FEATURE:
<223> OTHER INFORMATION: synthetic sequence

<400> SEQUENCE: 14
gcctggaagg acctggagct gctggagcag gagaacaagg agcagcagaa ccagagcgag      60
gagatcctga gccacatcct gagcacctac aacaacatcg agagagactg ggagatgtgg     120
accatgaaca ac                                                         132

<210> SEQ ID NO 15
<211> LENGTH: 44
<212> TYPE: PRT
<213> ORGANISM: Artificial Sequence
<220> FEATURE:
<223> OTHER INFORMATION: synthetic sequence

<400> SEQUENCE: 15

Ala Trp Lys Asp Leu Glu Leu Leu Glu Gln Glu Asn Lys Glu Gln Gln
1               5                   10                  15

Asn Gln Ser Glu Glu Ile Leu Ser His Ile Leu Ser Thr Tyr Asn Asn
            20                  25                  30

Ile Glu Arg Asp Trp Glu Met Trp Thr Met Asn Asn
        35                  40

<210> SEQ ID NO 16
<211> LENGTH: 273
<212> TYPE: DNA
<213> ORGANISM: Artificial Sequence
<220> FEATURE:
<223> OTHER INFORMATION: synthetic sequence

<400> SEQUENCE: 16
gagctgaaga cccccctggg cgacaccacc cacacctgcc ccagatgccc cgagcccaag      60
agctgcgaca cccccccccc ctgccccaga tgccccgagc ccaagagctg cgacaccccc     120
cccccctgcc ccagatgccc cgagcccaag agctgcgaca cccccccccc ctgccccaga     180
tgccccctgg aaaatggtgg acatccctta tcagagaaaa cagttcttct gctggtgact     240
ccatttctgg cagcagcctg gagccttcat ccc                                  273

<210> SEQ ID NO 17
<211> LENGTH: 91
<212> TYPE: PRT
<213> ORGANISM: Artificial Sequence
<220> FEATURE:
<223> OTHER INFORMATION: synthetic sequence

<400> SEQUENCE: 17

Glu Leu Lys Thr Pro Leu Gly Asp Thr Thr His Thr Cys Pro Arg Cys
1               5                   10                  15

Pro Glu Pro Lys Ser Cys Asp Thr Pro Pro Cys Pro Arg Cys Pro
            20                  25                  30

Glu Pro Lys Ser Cys Asp Thr Pro Pro Cys Pro Arg Cys Pro Glu
        35                  40                  45

Pro Lys Ser Cys Asp Thr Pro Pro Cys Pro Arg Cys Pro Leu Glu
    50                  55                  60

Asn Gly Gly Thr Ser Leu Ser Glu Lys Thr Val Leu Leu Val Thr
65                  70                  75                  80

Pro Phe Leu Ala Ala Trp Ser Leu His Pro
                85                  90
```

```
<210> SEQ ID NO 18
<211> LENGTH: 405
<212> TYPE: DNA
<213> ORGANISM: Artificial Sequence
<220> FEATURE:
<223> OTHER INFORMATION: synthetic sequence

<400> SEQUENCE: 18
gcctggaagg acctggagct gctggagcag gagaacaagg agcagcagaa ccagagcgag      60
gagatcctga gccacatcct gagcacctac aacaacatcg agagagactg ggagatgtgg     120
accatgaaca acgagctgaa gacccccctg ggcgacacca cccacacctg ccccagatgc     180
cccgagccca agagctgcga cacccccccc ccctgcccca gatgccccga gcccaagagc     240
tgcgacaccc cccccctg ccccagatgc cccgagccca agagctgcga cacccccccc       300
ccctgcccca gatgccccct tgaaaatggt gggacatcct tatcagagaa aacagttctt     360
ctgctggtga ctccatttct ggcagcagcc tggagccttc atccc                     405

<210> SEQ ID NO 19
<211> LENGTH: 135
<212> TYPE: PRT
<213> ORGANISM: Artificial Sequence
<220> FEATURE:
<223> OTHER INFORMATION: synthetic sequence

<400> SEQUENCE: 19

Ala Trp Lys Asp Leu Glu Leu Leu Glu Gln Glu Asn Lys Glu Gln Gln
1               5                   10                  15

Asn Gln Ser Glu Glu Ile Leu Ser His Ile Leu Ser Thr Tyr Asn Asn
            20                  25                  30

Ile Glu Arg Asp Trp Glu Met Trp Thr Met Asn Asn Glu Leu Lys Thr
        35                  40                  45

Pro Leu Gly Asp Thr Thr His Thr Cys Pro Arg Cys Pro Glu Pro Lys
    50                  55                  60

Ser Cys Asp Thr Pro Pro Cys Pro Arg Cys Pro Glu Pro Lys Ser
65                  70                  75                  80

Cys Asp Thr Pro Pro Cys Pro Arg Cys Pro Glu Pro Lys Ser Cys
                85                  90                  95

Asp Thr Pro Pro Cys Pro Arg Cys Pro Leu Glu Asn Gly Gly Thr
            100                 105                 110

Ser Leu Ser Glu Lys Thr Val Leu Leu Val Thr Pro Phe Leu Ala
        115                 120                 125

Ala Ala Trp Ser Leu His Pro
    130                 135
```

METHODS FOR NON-MYELOABLATIVE BONE MARROW RECONSTITUTION

CROSS-REFERENCE TO RELATED APPLICATIONS

This application claims priority to U.S. Provisional Application No. 62/586,813, filed Nov. 15, 2017, which is hereby incorporated by reference in its entirety.

FIELD

The present disclosure provides methods and compositions for a non-myeloablative bone marrow transplant including during the treatment of various diseases, such as HIV, cancer (e.g. hematological cancers), and the like. In some embodiments provided herein are modified stem cells that engraft into a patient's bone marrow and allow for bone marrow reconstitution without the negative side effects experienced during conventional bone marrow transplantations. The cells can also be used to express a protein of interest that can be therapeutic in nature.

BACKGROUND

Bone marrow transplantation (BMT) is a procedure that replaces damaged or destroyed bone marrow with healthy bone marrow stem cells isolated from either the patient (autologous) or another person (allogeneic). BMTs have been used to treat not only leukemia, but also numerous other diseases, including severe aplastic anemia, lymphomas, multiple myeloma, immune deficiency disorders and some solid-tumor cancers.

Myeloablative BMTs involve initially treating a patient to kill cells (both normal and abnormal) in the bone marrow, followed by the transfusing of healthy bone marrow cells. For the first step, high doses of chemotherapy and/or radiation are required to kill the cells followed by the introduction of the allogenic or autologous cells. This process of killing off the patient's bone marrow is referred to as myeloablation. Because this process kills not only unhealthy cells, but also healthy immune and stem cells, patients are very susceptible to infections and often are required to take multiple antibiotics and remain in a sterile environment. Until the bone marrow has been reconstituted, the patients remains at a high risk of infection, with the recovery period lasting for up to six months. During this time, it is recommended that the patients remain close to the treating hospital or clinic in case complications arise. In addition to acute toxicities, myeloablative chemotherapy has been associated with many other side effects including cataracts, growth retardation, cardiotoxicity, and endocrine and reproductive problems. Young patients are particularly susceptible to these effects. Accordingly, there is a need for new compositions and methods to perform BMTs. This present disclosure satisfies these needs as well as others.

SUMMARY

[To Be Completed Once claims are Finalized]

BRIEF DESCRIPTION OF THE DRAWINGS

FIG. 2A depicts % total (dead and live) GFP$^-$ cells, FIG. 2B depicts % live GFP$^+$ granulocytes.

FIG. 7 depicts a non-limiting schematic of a study design for a dose range and lentiviral vector efficacy study.

DETAILED DESCRIPTION

Figure 1:
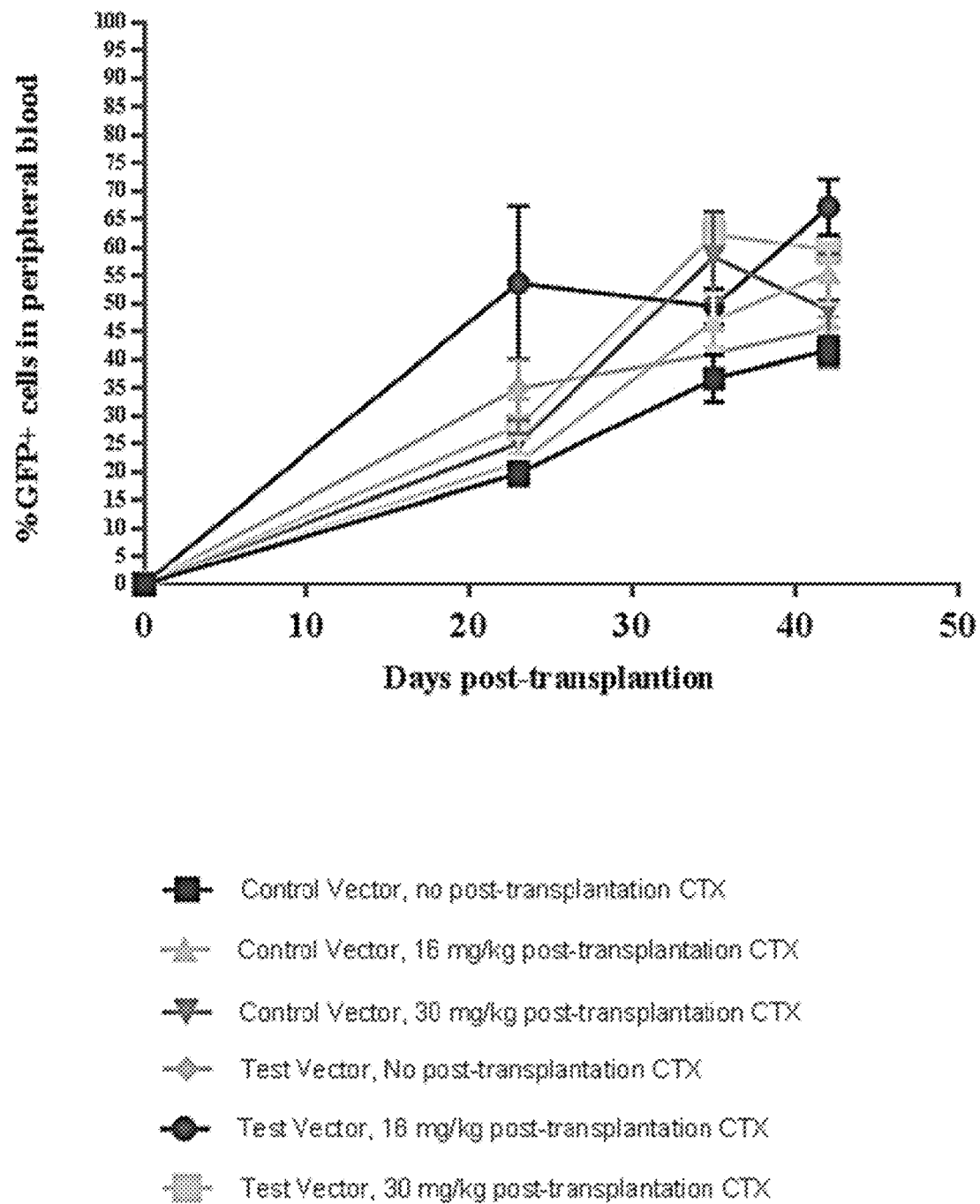
FIG. 1 depicts the percentages of live GFP (green fluorescent protein) positive (GFP$^+$) granulocytes in peripheral blood of mice that were administered bone marrow cells transduced with a lentiviral vector expressing EGFP ("Control Vector") or bone marrow cells transduced with a lentiviral vector expressing EGFP+ALDH1A1 ("Test Vector", SEQ ID NO: 2, FIG. 4) and treated with the indicated concentrations of daily intraperitoneal (i.p.) cyclophosphamide (CTX). On days 23, 35, and 42 of the study (which correspond to days 16, 28, and 35 of CTX administration, respectively) blood was collected by retroorbital bleed and the percentages of live GFP$^+$ granulocytes in peripheral blood were assessed by flow cytometry. For each no post transplantation CTX treatment group, n=3, for all other groups, n=6.

It is to be understood, although not always explicitly stated that all numerical designations are preceded by the term "about." As used herein, the term "about" means that the numerical value is approximate and small variations would not significantly affect the practice of the disclosed embodiments.

It must be noted that as used herein and in the appended claims, the singular forms "a", "an", and "the" include plural referents unless the context clearly dictates otherwise. Thus, for example, reference to "a cell" includes a plurality of cells.

Definitions

As used herein the following terms have the following meanings.

The term "about" when used before a numerical designation, e.g., temperature, time, amount, concentration, and such other, including a range, indicates approximations which may vary by (+) or (−) 20%, 10%, 5% or 1%.

Also as used herein, "and/or" refers to and encompasses any and all possible combinations of one or more of the associated listed items, as well as the lack of combinations when interpreted in the alternative ("or").

The terms "administering," "administer" and the like refer to introducing an agent (e.g., a cell) into a subject. Typically, an effective amount is administered, which amount can be determined by the treating physician or the like. Any route of administration, such as topical, subcutaneous, peritoneal, intravenous, intraarterial, inhalation, vaginal, rectal, nasal, oral, buccal, introduction into the cerebrospinal fluid, or instillation into body compartments can be used. The terms and phrases "administering" and "administration of," when used in connection with a composition (and grammatical equivalents) refer both to direct administration, which may be administration to a patient by a medical professional or by self-administration by the patient, and/or to indirect administration, which may be the act of prescribing a drug. For example, a physician who instructs a patient to self-administer an agent (e.g., a cell) and/or provides a patient with a prescription for a drug is administering the agent to the patient. "Periodic administration" or "periodically administering" refers to multiple treatments that occur on a daily, weekly, or a monthly basis. Periodic administration may also refer to administration of an agent one, two, three or more time(s) per day.

As used herein, the terms "comprising" (and any form of comprising, such as "comprise", "comprises", and "comprised"), "having" (and any form of having, such as "have" and "has"), "including" (and any form of including, such as "includes" and "include"), or "containing" (and any form of containing, such as "contains" and "contain"), are inclusive or open-ended and do not exclude additional, unrecited elements or method steps. Any step or composition that uses the transitional phrase of "comprise" or "comprising" can also be said to describe the same with the transitional phase of "consisting of" or "consists."

An "effective amount" is an amount of an agent or compound (e.g., cell or population of cells) sufficient to effect beneficial or desired results. An effective amount can be in one or more administrations, applications or doses. Determination of these parameters is well within the skill of the art. These considerations, as well as effective formulations and administration procedures are well known in the art and are described in standard textbooks.

As used herein, the term "contacting" means bringing together of two elements in an in vitro system or an in vivo system. For example, "contacting" a virus with a cell or with an individual or patient or cell includes the administration of the virus to an individual or patient, such as a human, as well as, for example, introducing a compound into a sample containing a cellular or purified preparation containing the cells of interest.

The term "heterologous" when referencing a nucleic acid molecule, protein, vector, or expression cassette refers to a nucleic acid molecule, protein, vector, or expression cassette that is expressed in a cell through the manipulation of a user and is not naturally occurring. For example, a heterologous gene refers to a gene that is expressed by a vector or other vehicle that is put in the cell or to a gene that is in the genome that has been modified through a gene editing methods, such as CRISPR, or other recombination techniques to replace the gene in a cell. One of skill in the art would understand that the term "heterologous" does not refer to a naturally occurring gene in the genome of a cell that has not been modified. "Heterologous" can also be referred to as "exogenous."

The term "isolated" as used herein with respect to nucleic acids, such as DNA or RNA, refers to molecules separated from other DNAs or RNAs, respectively that are present in the natural source of the macromolecule. The term "isolated" as used herein also refers to a nucleic acid or peptide that is substantially free of cellular material, viral material, or culture medium when produced by recombinant DNA techniques, or chemical precursors or other chemicals when chemically synthesized. Moreover, an "isolated nucleic acid" is meant to include nucleic acid fragments which are not naturally occurring as fragments and would not be found in the natural state. An "isolated cell," for example, an isolated bone marrow cell is a cell that is substantially free of other cellular material, tissue, medium of the environment in which it is naturally found.

The term "myeloablative" means a treatment that causes long lasting (usually irreversible) pancytopenia, kills cells in the bone marrow within 1 to 3 weeks from administration, and does not allow autologous hematologic recovery. Bacigalupo et al., *Biol Blood Marrow Transplant.* 2009, 15(12): 1628-1633. Examples of myeloablative doses of cyclophosphamide include, without limitation, 2.5 mg/kg/day CTX or greater for a period of time that results in cumulative toxicity (McKinley et al., *Clin J Am Soc Nephrol.* 2009, 4:1754-1760).

The term "non-myeloablative" means a treatment that causes no, minimal, or reversible cytopenia with little toxicity. Non-myeloablative regimens are immuno-ablation. Examples of non-myeloablative doses include, without limitation, approximately 1.3 mg/kg/day for a period of time that does not result in cumulative toxicity or 1.0 to 1.5 mg/kg/day for 2 to 4 months (McKinley et al., *Clin J Am Soc Nephrol.* 2009, 4:1754-1760). Other non-myeloablative doses are described throughout and are included within the definition of non-myeloablative doses. An agent or dose of an agent that results in "cumulative toxicity" refers to a dose that over time will lead to toxicity in the patient. For example, cyclophosphamide that is administered to a human at a dose of 2.5 mg/kg/day for a period of weeks will lead to cumulative toxicity.

A "subject," "individual" or "patient" is used interchangeably herein and refers to a vertebrate, for example a primate, a mammal or preferably a human. Mammals include, but are not limited to equines, canines, bovines, ovines, murines, rats, simians, and humans.

The term "sequence identity" with respect to a protein or amino acid sequence (or a DNA or RNA sequence) refers to the percentage of amino acid residues (or nucleotide residues) in a candidate sequence that are identical to the amino acid residues in the specific protein or amino acid sequence (or nucleotide residues in the specific DNA or RNA sequence), after aligning the sequences and introducing gaps, if necessary, to achieve a maximum percent sequence identity, and not considering any conservative substitutions as part of the sequence identity. Alignment can be achieved by any method known to one of skill in the art, for example, by using publicly available programs such as BLAST and EMBOSS. Those skilled in the art can determine appropriate parameters for measuring alignment, including any algorithms needed to achieve maximal alignment over the full length of the sequences being compared, but in some embodiments, the default parameters are used. The programs can be accessed for example at the National Center for Biotechnology Information.

The term "variant" as used herein, is a nucleic acid or protein that differs from a reference nucleic acid or protein (i.e., calmodulin or fragment thereof), but retains essential properties (i.e., biological activity). A typical variant of a polynucleotide differs in nucleotide sequence from another, reference polynucleotide. Changes in the nucleotide sequence may or may not alter the amino acid sequence of a polypeptide encoded by the reference polynucleotide. Nucleotide changes may result in amino acid substitutions, additions, deletions, fusions, and/or truncations in the polypeptide encoded by the reference sequence.

The term "vector" is used herein to refer to a nucleic acid molecule capable of transferring or transporting another nucleic acid molecule. The transferred nucleic acid is generally linked to, for example, the vector nucleic acid molecule. A vector may include sequences that direct autonomous replication in a cell, or may include sequences sufficient to allow integration into cellular DNA. Vectors include, for example, plasmids (e.g., DNA plasmids or RNA plasmids), transposons, cosmids, bacterial or yeast artificial chromosomes and viral vectors. Useful viral vectors include, for example, adenoviruses, retroviruses, particularly replication defective retroviruses, and lentiviruses. In some embodiments, the vector has a nucleotide sequence of SEQ ID NO: 2 or SEQ ID NO: 4. In some embodiments, the vector comprises the nucleotide sequence of SEQ ID NO: 1, SEQ ID NO: 3, SEQ ID NO: 6, SEQ ID NO: 7, SEQ ID NO: 8, SEQ ID NO: 9, or any combination thereof.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

Methods for Performing Bone Marrow Transplant

Provided herein are methods for performing a bone marrow transplant in a patient in need thereof. Also are provided for methods for replacing a subject's bone marrow cells with a population of cells expressing a heterologous nucleic acid molecule expression cassette or a plurality of heterologous expression cassettes or with a cell that has had its genome edited and differs from the subject's genome. In some embodiments, these methods comprise administering to the patient one or more chemotherapeutic-resistant modified cells and administration of at least one dose of a chemotherapeutic agent. In certain embodiments, the dose is a non-myeloablative dose of a chemotherapeutic agent. In some embodiments, the amount of the cells is a therapeutically effective amount.

In some embodiments of the methods provided herein, the patient has HIV.

Chemotherapeutic-resistant modified cells for use in the disclosed methods may be any suitable cell known to one of skill in the art. For example, the cells can be stem cells or immune cells. Non-limiting examples of stem cells include a cord blood cell, fetal stem cell, embryonic stem cell (ESC), hematopoietic stem cell (HSC), hematopoietic progenitors cell, pluripotent stem cell (PSC), induced PSC (iPSC), or a cell derived therefrom. In some embodiments, the immune cell is a T cell. In some embodiments, the cells are CD34+ and/or CD4+. In some embodiments, the cells are mesenchymal stem cells, stromal stem cells, cord blood derived hematopoietic stem/progenitor cells, cord tissue derived stem/progenitor cells, iPSCs, HESCs, fetal tissue derived stem cells, CD4+ cells, and the like. In some embodiments, the stem cells are CD34+.

Chemotherapeutic Resistance

Chemotherapeutic-resistant cells for use in the present methods may be generated using any method known in the art for conferring chemotherapeutic resistance. In certain embodiments, the bone marrow transplant methods provided herein comprise modifying one or more cells to be chemotherapeutic resistant. For example, in certain embodiments methods are provided for performing a bone marrow transplant in a patient in need thereof comprising generating chemotherapeutic-resistant modified cells, administering to the patient an effective amount of the chemotherapeutic-resistant modified cells, and administering at least one dose of a chemotherapeutic agent. In certain embodiments, the dose is a non-myeloablative dose of a chemotherapeutic agent. In some embodiments, the chemotherapeutic resistant cell is resistant to a cyclophosphamide. In some embodiments, the chemotherapeutic resistant cell is resistant to a non-myeloablative amount of cyclophosphamide.

In some embodiments, the cells may be modified to express an exogenous chemotherapeutic-resistant gene (i.e., a transduced gene), for example, the exogenous chemotherapeutic resistant gene can be a nucleic acid sequence encoding a cyclophosphamide-resistant gene, a variant, or portion thereof. In some embodiments, the cyclophosphamide-resistant gene is aldehyde dehydrogenase 1 (ALDH1). In some embodiments, the ALDH1 is a nucleic acid molecule comprising the sequence as set forth in SEQ ID NO: 1 or a variant thereof. In some embodiments, the ALDH1 is expressed in a lentiviral vector comprising the sequence as set forth in SEQ ID NO: 2 or SEQ ID NO: 4 or a variant thereof. A cell modified with ALDH1, while resistant to cyclophosphamide, can remain sensitive to other non-cyclophosphamide chemotherapeutics (i.e., the cell would not be multidrug resistant).

Any modification method known to one of skill in the art can be employed to express the exogenous chemotherapeutic-resistant gene, including viral vectors (e.g., adenoviruses, retroviruses, such as replication defective retroviruses, and lentiviruses), non-viral vectors (e.g., episomal, plasmids), or a transposon system (e.g., Sleeping Beauty or PiggyBac). In some embodiments, the vector has a nucleotide sequence of SEQ ID NO: 2 or SEQ ID NO: 4. In some embodiments, the chemotherapeutic-resistant gene is a synthetic messenger RNA (mRNA). Synthetic mRNAs provide the genetic information for making proteins of interest and can be chemically modified to avoid triggering an immune response. Zangi et al. (2013) *Nature Biotech* 31:898-907. Since mRNAs do not integrate into the host cell genome, the synthetic RNA acts for a period of time and then disappears as the cell divides. In some embodiments, the synthetic mRNAs are modified, for example, with pseudouridine and/or 5-methyl-cytidine, to reduce innate antiviral response to single-stranded RNA. In some embodiments, the synthetic RNAs encode ALDH (e.g. ALDH1) and/or equivalents of each thereof.

In some embodiments, the chemotherapeutic-resistance, for example the cyclophosphamide resistance, is transiently expressed by the modified cell. In some embodiments, the transiently expressed cyclophosphamide is expressed by the modified cell for a period of about 1 week, about 2 weeks, about 3 weeks, about 1 month, about 2 months, about 3 months, about 6 months, about one year, about two years, or about three years. Transient expression refers to the persistence of the expression of the gene or protein conferring the resistance. Transient means that the resistance is not permanent.

In some embodiments, an exogenous chemotherapeutic-resistance gene, e.g., a cyclophosphamide-resistance gene, is introduced into a cell using any one of a variety of well-known techniques, such as non-viral based transfection of the cell. Introduction into the cell may be performed by any non-viral based transfection method known in the art, such as, but not limited to, electroporation, calcium phosphate mediated transfer, nucleofection, sonoporation, heat shock, magnetofection, liposome mediated transfer, microinjection, microprojectile mediated transfer (nanoparticles), cationic polymer mediated transfer (DEAE-dextran, polyethylenimine, polyethylene glycol (PEG) and the like, or cell fusion. Other methods of transfection include transfection reagents such as Lipofectamine™, Dojindo Hilymax™ Fugene™, jetPEI™, Effectene™, and DreamFect™.

Isolating and/or Purifying Cells

Chemotherapeutic-resistant modified cells for use in the present methods may be cells from a patient (i.e., autologous cells), cells from a donor (i.e., allogeneic cells), or any combination thereof that have been modified to confer chemotherapeutic resistance. In certain embodiments, the methods provided herein further comprise isolating and/or purifying cells from a patient or a donor. In certain of these embodiments, the methods further comprise modifying the cells to be chemotherapeutic resistant. For example, in certain embodiments methods are provided for performing a bone marrow transplant in a patient in need thereof comprising isolating and/or purifying one or more cells from a patient or subject, modifying the one or more cells to be chemotherapeutic resistant as described herein, administering to the patient an effective amount of the one or more chemotherapeutic-resistant modified cells, and administering at least one dose of a chemotherapeutic agent.

Cells can be isolated by any method known to one of skill in the art, for example, based on expression/lack of expression of certain markers, rates of proliferation, and differentiation potential. In some embodiments, the cells are isolated based on the presence of a particular marker or combination of markers including, for example, CD34, CD4, Sca-1 CD38, CD123, CD90, CD45, CD133, antigen presenting cell markers (CD8, CD8alpha, CD11b, CD11c, CD103, CD205, CD24, CD115, CD117, CD135, CD11c$^{low}$, CD45RA, CD123, ILT-7, MHC class II, MHC Class II$^{low}$, TLR7, and/or TRL9). In some embodiments, the cells are isolated based on the absence of a particular marker, for example, CD3, CD14, CD19, CD56, and/or CD66b. In other embodiments, negative selection is performed for markers of, for example, T cells, B cells, granulocytic, and/or myelo-monocytic cells. In some embodiments, cells are isolated based on the presence of Thy-1 alone or in combination with any other marker. In some embodiments, HSCs are isolated based on Lin$^-$Thy1$^+$Sca-1$^+$ expression profile. In some embodiments, mouse HSCs can be isolated by the expression profile CD34$^-$, Sca1$^-$, c-kit$^+$. In some embodiments human HSCs can be isolated based on CD34 expression.

Chemotherapeutic Agent

In some embodiments, the methods provided herein comprise administering one or more doses of a chemotherapeutic agent to the patient. In some embodiments, the dose is a non-myeloablative dose of a chemotherapeutic agent. The chemotherapeutic agent can be any suitable chemotherapeutic agent known to one of skill in the art. Non-limiting examples of chemotherapeutic agents include actinomycin, all-trans retinoic acid, azacitidine, azathioprine, bleomycin, bortezomib, busulfan, capecitabine, carboplatin, carmustine (BCNU), cisplatin, chlorambucil, cyclophosphamide, cytarabine, daunorubicin, docetaxel, doxifluridine, doxorubicin, epirubicin, epothilone, etoposide, fluorouracil, gemcitabine, hydroxyurea, idarubicin, imatinib, irinotecan, lomustine (CCNU), mechlorethamine, melphalan, mercaptopurine, methotrexate, mitoxantrone, nimustin (ACNU) oxaliplatin, paclitaxel, pemetrexed, temezolamide, teniposide, thiotepa, tioguanine, topotecan, treosulfan, valrubicin, vemurafenib, vinblastine, vincristine, vindesine, and vinorelbine.

Disease Specific Modifications

In certain embodiments of the methods provided herein, the chemotherapeutic-resistant modified cells may comprise one or more additional modifications unrelated to chemotherapeutic resistance. For example, in certain embodiments, the cells may be further modified to express additional HIV/disease-specific modifications. Accordingly, in certain embodiments the bone marrow transplant methods provided herein further comprise incorporating one or more additional modifications, including one or more HIV/disease-specific modifications. For example, in certain embodiments, methods are provided for performing a bone marrow transplant in a patient in need thereof comprising isolating and/or purifying one or more cells from a patient or subject, modifying the one or more cells to be chemotherapeutic resistant as described herein, incorporating one or more additional modifications into the one or more cells, administering to the patient an effective amount of the one or more chemotherapeutic-resistant modified cells, and administering at least one dose of a chemotherapeutic agent. In some embodiments, the dose is a non-myeloablative dose of a chemotherapeutic agent.

In some embodiments, the modified cells are further modified to be HIV resistant. For example, the modified cell can be further modified to express at least one mutant HIV co-receptor that confers resistant to HIV infection, a mutation or plurality of mutations of at least one HIV co-receptor, expression of at least one HIV fusion inhibitor, or any combination thereof. In some embodiments, the cells are modified to express a molecule that inhibits or reduces the expression of a HIV co-receptor. In some embodiments, the molecule is an antisense molecule. In some embodiments, the cells are modified to express shCCR5, shCXCR4, a GP-41 fusion inhibitor, C46 fusion inhibitor, a C34 fusion inhibitor, any other C-peptide fusion inhibitor, or any combination thereof. In some embodiments, the CCR5 mutation is the CCR5-delta 32 mutation. In some embodiments, both copies of the CCR5 gene in the cells are replaced with the CCR5-delta 32 mutation. In some embodiments, one copy of the CCR5 gene is replaced with the CCR5-delta 32 mutation.

The present disclosure provides cells that are modified to have chemotherapeutic resistance, for example cyclophosphamide resistance, and HIV resistance. In some embodiments, cells may be modified to have cyclophosphamide resistance and HIV resistance. The HIV-resistance may be conferred by reduced expression of at least one HIV co-receptor, a mutation or plurality of mutations of at least one HIV co-receptor, expression of at least one HIV fusion inhibitor, or any combination thereof. The HIV-resistance may be conferred from reduced expression of the CCR5 HIV co-receptor, reduced expression of the CXCR4 co-receptor, expression of a C-peptide fusion inhibitor (e.g., a C46 fusion inhibitor or a C34 fusion inhibitor) or any combination thereof.

The cells can also be modified to express any molecule of interest. The molecule of interest can be modified as determined by the user or the specific patient need.

Administration to Patients

In some embodiments, the methods provided herein comprise administering to the subject an effective amount of the chemotherapeutic-resistance modified cells and a non-myeloablative dose of a chemotherapeutic agent. The modified cells and chemotherapeutic agent can be administered by any appropriate route, which will be apparent to the skilled person depending on the disease or condition to be treated. Typical routes of administration include intravenous, intra-arterial, intramuscular, subcutaneous, intracranial, intranasal, intradermal, oral or intraperitoneal.

In some embodiments, about $1\times10^8$ to about $1\times10^{11}$ cells per $m^2$ of body surface area of the subject are administered to the subject. The cells can be administered to an individual by absolute numbers of cells, e.g., said individual can be administered from about 1000 cells/injection to up to about 10 billion cells/injection, such as at about, at least about, or at most about, $1\times10^8$, $1\times10^7$, $5\times10^7$, $1\times10^6$, $5\times10^6$, $1\times10^5$, $5\times10^5$, $1\times10^4$, $5\times10^4$, $1\times10^3$, $5\times10^3$ (and so forth) cells per injection, or any ranges between any two of the numbers, end points inclusive. In some embodiments, about $5\times10^6$/kg to about $10\times10^6$/kg of cells are used for a HSC transplant.

In other embodiments, the subject can be administered from about 1000 cells/injection/$m^2$ to up to about 10 billion cells/injection/$m^2$, such as at about, at least about, or at most about, $1\times10^8/m^2$, $1\times10^7/m^2$, $5\times10^7/m^2$, $1\times10^6/m^2$, $5\times10^6/m^2$, $1\times10^5/m^2$, $5\times10^5/m^2$, $1\times10^4/m^2$, $5\times10^4/m^2$, $1\times10^3/m^2$, $5\times10^3/m^2$ (and so forth) cells per injection, or any ranges between any two of the numbers, end points inclusive.

In other embodiments, the cells can be administered to such individual by relative numbers of cells, e.g., said individual can be administered about 1000 cells to up to about 10 billion cells per kilogram of the individual, such as at about, at least about, or at most about $1\times10^8$, $5\times10^7$, $1\times10^7$, $5\times10^6$, $1\times10^6$, $5\times10^5$, $1\times10^5$, $5\times10^4$, $1\times10^4$, $5\times10^3$, $1\times10^3$, (and so forth) cells per kilogram of the individual, or any ranges between any two of the numbers, end points inclusive.

In some embodiments, at least one non-myeloablative dose of a chemotherapeutic agent is administered to the patient. The administration of the chemotherapeutic agent can occur concurrently or sequentially with the administration of the modified cells. In some embodiments, at least one non-myeloablative dose of the chemotherapeutic agent is administered after administration of the modified cells. In some embodiments, a preconditioning step (also referred to herein as "pretreatment step") is performed prior to administration of the cells wherein the patient is administered at least one dose of a chemotherapeutic agent, for example, fludarabine or cyclophosphamide, prior to administration of the modified cells. In some embodiments, the preconditioning step is a non-myeloablative chemotherapeutic preconditioning step. In some embodiments, a preconditioning step is not performed prior to administration of the cells. It is contemplated that cells of the present disclosure will still be able to efficiently engraft into the patient's bone marrow even without the preconditioning step (e.g., fludarabine) prior to administration of the cells.

In some embodiments, the at least one non-myeloablative dose of a chemotherapeutic agent for a human subject or patient is a non-myeloablative dose of cyclophosphamide. In some embodiments, the non-myeloablative dose of cyclophosphamide is from about 0.15 mg/kg/day to less than 2.5 mg/kg/day, from about 0.4 mg/kg/day to about 1.7 mg/kg/day, or from about 0.8 mg/kg/day to about 1.5 mg/kg/day. In some embodiments, the non-myeloablative dose of cyclophosphamide is about 0.15 mg/kg/day, about 0.2 mg/kg/day, about 0.25 mg/kg/day, about 0.3 mg/kg/day, about 0.35 mg/kg/day, about 0.4 mg/kg/day, about 0.45 mg/kg/day, about 0.5 mg/kg/day, about 0.55 mg/kg/day, about 0.6 mg/kg/day, about 0.65 mg/kg/day, about 0.7 mg/kg/day, about 0.75 mg/kg/day, about 0.8 mg/kg/day, about 0.85 mg/kg/day, about 0.9 mg/kg/day, about 0.95 mg/kg/day, about 1.0 mg/kg/day, about 1.1 mg/kg/day, about 1.2 mg/kg/day, about 1.3 mg/kg/day, about 1.4 mg/kg/day, about 1.5 mg/kg/day, about 1.6 mg/kg/day, about 1.7 mg/kg/day, about 1.8 mg/kg/day, about 1.9 mg/kg/day, about 2.0 mg/kg/day, about 2.1 mg/kg/day, about 2.2 mg/kg/day, about 2.3 mg/kg/day, or about 2.4 mg/kg/day. In some embodiments, the non-myeloablative dose of cyclophosphamide is about 1.3 mg/kg/day. In some embodiments, the non-myeloablative dose of cyclophosphamide is from about 0.8 mg/kg/day to about 1.6 mg/kg/day, about 0.8 mg/kg/day, about 0.98 mg/kg/day, about 1.3 mg/kg/day, about 1.5 mg/kg/day, or about 1.6 mg/kg/day. In some embodiments, the non-myeloablative dose of cyclophosphamide is about 0.5 to about 2 mg/kg/day.

In some embodiments, the non-myeloablative dose of the chemotherapeutic agent is administered every day for at least about 1 day, at least about 2 days, at least about 3 days, at least about 4 days, at least about 5 days, at least about 6 days, at least about 1 week, at least about 2 weeks, at least about 3 weeks, at least about 1 month, at least about 2 months, at least about 3 months, at least about 4 months, at least about 5 months, at least about 6 months, at least about 1 year, or longer.

In some embodiments, the non-myeloablative dose is provided for a period of time that does not result in cumulative toxicity. For example, the period of time that does not result in cumulative toxicity is a period of times less than about 1 year, less than about 6 months, less than about 3 months, less than about 2 months, less than about 1 month, less than about 3 weeks, less than about 2 weeks, less than about 1 week, less than about 6 days, less than about 5 days, less than about 4 days, less than about 3 days, or less than about 2 days.

In some embodiments, there is at least one break for a period of time between the administering of the cyclophosphamide-resistant modified cells and at least one non-myeloablative dose of a chemotherapeutic agent. For example, the period of time can be for about 2 days, about 3 days, about 4 days, about 5 days, about 6 days, about 1 week, about 2 weeks, about 3 weeks, about a month, about 2 months, about 3 months, about 6 months, about a year or more. In some embodiments, the period of time is about 3 days, about 7 days, about 10 days, and about 14 days.

In some embodiments, greater than about 60%, about 70%, about 80%, about 90%, about 95%, or 100% of the patient's bone marrow is replaced with the modified cells. In some embodiments, greater than about 60%, about 70%, about 80%, about 90%, about 95%, or 100% of the patient's bone marrow is replaced with the modified cells within about a year. In some embodiments, greater than about 60%, about 70%, about 80%, about 90%, about 95%, or 100% of the patient's bone marrow is replaced with the modified cells within about 6 months. In some embodiments, greater than about 60%, about 70%, about 80%, about 90%, about 95%, or 100% of the patient's bone marrow is replaced with the modified cells within about 5 months. In some embodiments, greater than about 60%, about 70%, about 80%, about 90%, about 95%, or 100% of the patient's bone marrow is replaced with the modified cells within about 4 months. In some embodiments, greater than about 60%, about 70%, about 80%, about 90%, about 95%, or 100% of the patient's bone marrow is replaced with the modified cells within about 3 months. In some embodiments, greater than about 60%, about 70%, about 80%, about 90%, about 95%, or 100% of the patient's bone marrow is replaced with the modified cells within about 2 months. In some embodiments, greater than about 60%, about 70%, about 80%, about 90%, about 95%, or 100% of the patient's bone marrow is replaced with the modified cells within about 1 month. In some embodiments, greater than about 60%, about 70%, about 80%, about 90%, about 95%, or 100% of the patient's bone marrow is replaced with the modified cells within about 2 weeks. In some embodiments, greater than about 60%, about 70%, about 80%, about 90%, about 95%, or 100% of the patient's bone marrow is replaced with the modified cells within about 1 week.

In some embodiments, the patient is not myeloablated and/or immunocompromised during the method. In some embodiments, the patient does not experience clinically relevant anemia, neutropenia, thrombocytopenia, pancytopenia, low platelets, low white blood cells, low red cells, or any combination thereof or related symptom(s).

In another embodiment, upon treatment with the cells and chemotherapeutic agent of the present disclosure, the subject or subject group may exhibit one or more of the following outcomes:

(i) an increase in white blood cells of at least about 5%, at least about 10%, at least about 15%, at least about 20%, at least about 25%, at least about 30%, at least about 35%, at least about 40%, at least about 45%, at least about 50%, at least about 55%, at least 60%, at least 65%, at least 70%, at least about 75%, at least 80%, at least 85%, at least 90%, at least 95%, or at least 99% (actual % change or median % change) as compared to a control;

(ii) an increase in granulocytes of at least about 5%, at least about 10%, at least about 15%, at least about 20%, at least about 25%, at least about 30%, at least about 35%, at least about 40%, at least about 45%, at least about 50%, at least about 55%, at least 60%, at least 65%, at least 70%, at least about 75%, at least 80%, at least 85%, at least 90%, at least 95%, or at least 99% (actual % change or median % change) compared to a control;

(iii) an increase in neutrophils of at least about 5%, at least about 10%, at least about 15%, at least about 20%, at least about 25%, at least about 30%, at least about 35%, at least about 40%, at least about 45%, at least about 50%, at least about 55%, at least 60%, at least 65%, at least 70%, at least about 75%, at least 80%, at least 85%, at least 90%, at least 95%, or at least 99% (actual % change or median % change) compared to a control;

(iv) an increase in lymphocytes of at least about 5%, at least about 10%, at least about 15%, at least about 20%, at least about 25%, at least about 30%, at least about 35%, at least about 40%, at least about 45%, at least about 50%, at least about 55%, at least 60%, at least 65%, at least 70%, at least about 75%, at least 80%, at least 85%, at least 90%, at least 95%, or at least 99% (actual % change or median % change) compared to a control;

(v) an increase in eosinophils of at least about 5%, at least about 10%, at least about 15%, at least about 20%, at least about 25%, at least about 30%, at least about 35%, at least about 40%, at least about 45%, at least about 50%, at least about 55%, at least 60%, at least 65%, at least 70%, at least about 75%, at least 80%, at least 85%, at least 90%, at least 95%, or at least 99% (actual % change or median % change) compared to a control;

(vi) an increase in monocytes of at least about 5%, at least about 10%, at least about 15%, at least about 20%, at least about 25%, at least about 30%, at least about 35%, at least about 40%, at least about 45%, at least about 50%, at least about 55%, at least 60%, at least 65%, at least 70%, at least about 75%, at least 80%, at least 85%, at least 90%, at least 95%, or at least 99% (actual % change or median % change) compared to a control;

(vii) an increase in basophils of at least about 5%, at least about 10%, at least about 15%, at least about 20%, at least about 25%, at least about 30%, at least about 35%, at least about 40%, at least about 45%, at least about 50%, at least about 55%, at least 60%, at least 65%, at least 70%, at least about 75%, at least 80%, at least 85%, at least 90%, at least 95%, or at least 99% (actual % change or median % change) compared to a control;

(viii) an increase in red blood cells of at least about 5%, at least about 10%, at least about 15%, at least about 20%, at least about 25%, at least about 30%, at least about 35%, at least about 40%, at least about 45%, at least about 50%, at least about 55%, at least 60%, at least 65%, at least 70%, at least about 75%, at least 80%, at least 85%, at least 90%, at least 95%, or at least 99% (actual % change or median % change) compared to a control;

(ix) an increase in all three cellular components of the blood (red cells, white cells, and platelets) of at least about 5%, at least about 10%, at least about 15%, at least about 20%, at least about 25%, at least about 30%, at least about 35%, at least about 40%, at least about 45%, at least about 50%, at least about 55%, at least 60%, at least 65%, at least 70%, at least about 75%, at least 80%, at least 85%, at least 90%, at least 95%, or at least 99% (actual % change or median % change) compared to a control;

(x) no relapse for a period of at least about 6 months, about 1 year, about 2 years, about 3 years, about 4 years, about 5 years, about 6 years, about 7 years, about 8 years, about 9 years, about 10 years, about 15 years, about 20 years, about 25 years, about 30 years, about 35 years, about 40 years, about 45 years, about 50 years, about 55 years, about 60 years, or longer;

(xi) an increase in relapse free survival of a patient of at least about 1 year, about 2 years, about 3 years, about 4 years, about 5 years, about 6 years, about 7 years, about 8 years, about 9 years, about 10 years, about 15 years, about 20 years, about 25 years, about 30 years, about 35 years, about 40 years, about 45 years, about 50 years, about 55 years, about 60 years, or longer as compared to a control;

(xii) an increase in survival of a patient of at least about 1 year, about 2 years, about 3 years, about 4 years, about 5 years, about 6 years, about 7 years, about 8 years, about 9 years, about 10 years, about 15 years, about 20 years, about 25 years, about 30 years, about 35 years, about 40 years, about 45 years, about 50 years, about 55 years, about 60 years, or longer as compared to a control;

(xiii) a decrease in HIV intracellular longevity of at least about 5%, at least about 10%, at least about 15%, at least about 20%, at least about 25%, at least about 30%, at least about 35%, at least about 40%, at least about 45%, at least about 50%, at least about 55%, at least 60%, at least 65%, at least 70%, at least about 75%, at least 80%, at least 85%, at least 90%, at least 95%, or at least 99% (actual % change or median % change) compared to a control;

(xiv) a decrease in HIV reservoirs of at least about 5%, at least about 10%, at least about 15%, at least about 20%, at least about 25%, at least about 30%, at least about 35%, at least about 40%, at least about 45%, at least about 50%, at least about 55%, at least about 60%, at least 65%, at least 70%, at least about 75%, at least 80%, at least 85%, at least 90%, at least 95%, or at least 99% (actual % change or median % change) compared to a control; and (xv) a depletion of viral DNA of at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least 70%, at least about 75%, at least 80%, at least 85%, at least 90%, at least 95%, or at least 99% (actual % change or median % change) compared to a control.

In some embodiments, the control can be a subject treated with a placebo, a baseline control, or a subject treated with unmodified cells.

In some embodiments, the modified cells are administered to the subject for a period effective to reduce at least one symptom of HIV by at least about 2%, at least about 3%, at least about 4%, at least about 5%, at least about 6%, at least about 7%, at least about 8%, at least about 9%, at least about 10%, at least about 11%, at least about 12%, at least about 13%, at least about 14%, at least about 15%, at least about 20%, at least about 25%, at least about 30% at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 97%, at least about 98%, at least about 99%, or by 100% compared to a control. The control can be a subject treated with a placebo, a baseline control, or a subject treated with unmodified cells.

Non-limiting symptoms include, fever, headache, lack of energy, skin rashes, skin sores, swollen glands, infections (e.g., pneumonia, tuberculosis, hepatitis C), night sweats, diarrhea, nausea and vomiting, weight loss, severe headache, joint pain, muscle aches, and chronic cough.

In some embodiments the modified cells are administered with at least one other HIV therapy. Suitable other HIV therapies include any HIV therapy known to one of skill in the art. Non-limiting examples of other HIV therapies include and combination drugs (e.g., efavirenz/emtricitabine/tenofovir disoproxil fumarate (Atripla®), emtricitabine/rilpivirine/tenofovir disoproxil fumarate (Complera®), elvitegravir/cobicistat/emtricitabine/tenofovir disoproxil fumarate (Stribild®), and abacavir/dolutegravir/lamivudine (Triumeq®)), a nucleoside/nucleotide reverse transcriptase inhibitor (NRTI) (e.g., abacavir (Ziagen®), efavirenz/emtricitabine/tenofovir disoproxil fumarate (Atripla®), lamivudine/zidovudine (Combivir®), emtricitabine/rilpivirine/tenofovir disoproxil fumarate (Complera®), emtricitabine (Emtriva®), lamivudine (Epivir®), abacavir/lamivudine (Epzicom®), zidovudine (Retrovir®), abacavir/lamivudine/zidovudine (Trizivir), emtricitabine/tenofovire disoproxil fumarate (Truvada®), didanosine (Videx®), didanosine extended release (Videx EC®), tenofovir disoproxil fumarate (Viread®), and stavudine (Zerit®)), a non-nucleoside reverse transcriptase inhibitor (NNRTI), a protease inhibitor (e.g. tipranavir (Aptivus®), indinavir (Crixivan®), atazanavir/cobicistat (Evotaz®), saquinavir (Invirase®), lopinavir/ritonavir (Kaletra®), fosamprenavir (Lexiva®), ritonavir (Norvir®), darunavir/cobicistat (Prezcobix®), darunavir (Prezista®), atazanavir (Reyataz®), nelfinavir (Viracept®)), an entry inhibitor (e.g., enfuvirtide (Fuzeon®)), an integrase inhibitor (e.g., raltegravir (Isentress®), dolutegravir (Tivicay®), and elvitegravir (Vitekta®)), a chemokine co-receptor antagonists (CCR5 antagonists) (e.g., maraviroc (Selzentry®) or vicriviroc), a cytochrome P4503A inhibitor, and immune-based therapies (e.g., hydroxychloroquine sulfate (Plaquenil). In some embodiments, the modified cells and the at least one other HIV therapy are administered simultaneously. In other embodiments, the modified cells and the at least one other HIV therapy are administered sequentially. In some embodiments, administration of at least one of the above-mentioned other HIV therapies is expressly excluded, for example, in some embodiments a NRTI is expressly excluded. In some embodiments, no other HIV therapy is administered other than the modified cells disclosed herein and at least one non-myeloablative dose of a chemotherapeutic agent (e.g., cyclophosphamide).

The cells, chemotherapeutic agent, and optionally, other HIV therapies can be administered once to a patient with HIV or can be administered multiple times, e.g., once every 1, 2, 3, 4, 5, 6, 7, 8, 9, 10, 11, 12, 13, 14, 15, 16, 17, 18, 19, 20, 21, 22 or 23 hours, or once every 1, 2, 3, 4, 5, 6 or 7 days, or once every 1, 2, 3, 4, 5, 6, 7, 8, 9, 10 or more weeks during therapy, or any ranges between any two of the numbers, end points inclusive.

In some embodiments, methods of treating a patient with HIV are provided. In some embodiments, the methods comprise mobilizing the patients CD34$^+$ stem cells out of the marrow and into the periphery. In some embodiments, the cells are mobilized by the administration of G-CSF (Granulocyte-colony stimulating factor). G-CSF can be administered as, for example, a 1, 2, 3, 4, or 5 day regimen. In some embodiments, the G-CSF is administered for 3-5 days. The mobilized cells can be captured using methodology, such as apheresis. In some embodiments, the isolation of the cells, by, for example, apheresis is performed once the CD34$^+$ cell count is or exceeds 10.0 to 20.0×10$^6$/kg body weight. In some embodiments, the cell count is or exceeds 5.0 to 25.0×10$^6$/kg body weight. Although Cd34+ cells are used as the marker to capture the cells for transduction, other cell markers can be used, such as those described herein. For example, the cells that are used are isolated based on the presence of a particular marker or combination of markers including, for example, CD34, CD4, Sca-1 CD38, CD123, CD90, CD45, CD133, antigen presenting cell markers (CD8, CD8alpha, CD11b, CD11c, CD103, CD205, CD24, CD115, CD117, CD135, CD11c$^{low}$, CD45RA, CD123, ILT-7, MHC class II, MHC Class II$^{low}$, TLR7, and/or TRL9). In some embodiments, the cells are isolated based on the absence of a particular marker, for example, CD3, CD14, CD19, CD56, and/or CD66b. In other embodiments, negative selection is performed for markers of, for example, T cells, B cells, granulocytic, and/or myelomonocytic cells. In some embodiments, cells are isolated based on the presence of Thy-1 alone or in combination with any other marker. In some embodiments, HSCs are isolated based on Lin$^-$Thy1$^+$ Sca-1$^+$ expression profile. In some embodiments, mouse HSCs can be isolated by the expression profile CD34⁻, Sca1⁺, c-kit⁺. In some embodiments human HSCs can be isolated based on CD34 expression. In some embodiments, the isolated cells are CD34+ or CD4+, or any combination thereof.

In some embodiments, the methods comprise centrifuging the collection of cells. This can be done, for example, to develop a cell rich pellet. The cells can then be re-suspended in a cryopreservation solution and frozen. In some embodiments, the cryopreservation solution comprises a solution of heparinized Plasmalyte solution and 10% DMSO (Dimethylsulfoxide). In some embodiments, the cells are initially stored at −4° C., then the sample will be frozen down to the target temperature of −156° C. (when stored in the vapor phase) to −196° C. (when stored in the liquid phase).

In some embodiments, the methods comprise transducing the isolated cells to become resistant to a chemotherapeutic agents, such as cyclophosphamide. As described herein, chemotherapeutic resistance can be achieved by the expression of ALDH1. The ALDH1 can be introduced to the selected cells through the use of a vector (as described throughout the present specification), such as the use of a lentivral vector. The ALDH1 can be operably connected to a promoter that can be cell specific. In some embodiments, the promoter is CD34 promoter. In some embodiments, the promoter is a hCD34 promoter. In some embodiments, the promoter has a sequence of SEQ ID NO: 12. In some embodiments, the promoter is a hCD4 promoter, such as provided in SEQ ID NO: 8. In some embodiments, the sequence of ALDH1 is expressed as a protein as provided in SEQ ID NO: 10. In some embodiments, ALDH1 is encoded by a nucleic acid molecule comprising the sequence of SEQ ID NO: 1. Due to the degenerate nature of the genetic code the sequence of SEQ ID NO: 1 is provided as a non-limiting example and other nucleic acid molecules can be used to encode for the expression of a protein comprising SEQ ID NO: 10. In some embodiments, the ALDH1 comprises 1-10 conservative substitutions that do not change the function of ALDH1. In some embodiments, the expressed ALDH1 is at least 95% homologous or identical to SEQ ID NO: 10.

The expression of ALDH1 in the vector can also be driven by an enhancer element. For example, the enhancer element can be a CD3E enhancer. In some embodiments, the CD3E enhancer comprises the sequence of SEQ ID NO: 9.

In some embodiments, CD34⁺ cells can be isolated by magnetic bead separation. Lentiviral vector-mediated human CD34⁺ cell transduction can include, for example, a 24 h prestimulation of cells in media with the addition of the cytokines Stem Cell Factor (SCF), Fms-related tyrosine kinase 3 ligand (FLT3L), thrombopoietin (TPO), IL-6, IL-2, IL-3, fibronectin, or any combination thereof. In some embodiments, the cells are then contacted (infected) with the lentivirus expressing the ALDH1. In some embodiments, the vector comprises a sequence of SEQ ID NO: 2, SEQ ID NO: 4, or SEQ ID NO: 5. The contacting can be performed in the presence of the cytokines of SCF, FLT3L and TPO (each 100 ng ml⁻¹) in serum-free X-Vivo 10 media. The cells can then be optionally frozen or not frozen. In some embodiments, the cell are not contacted with an AAV or AV vector.

In some embodiments, the methods comprising infusing the transduced cells into the subject. In some embodiments, the subject has HIV. In some embodiments, the subject does not have HIV but is at high risk to obtain HIV and, therefore, desires to become HIV resistant.

Figure 9:
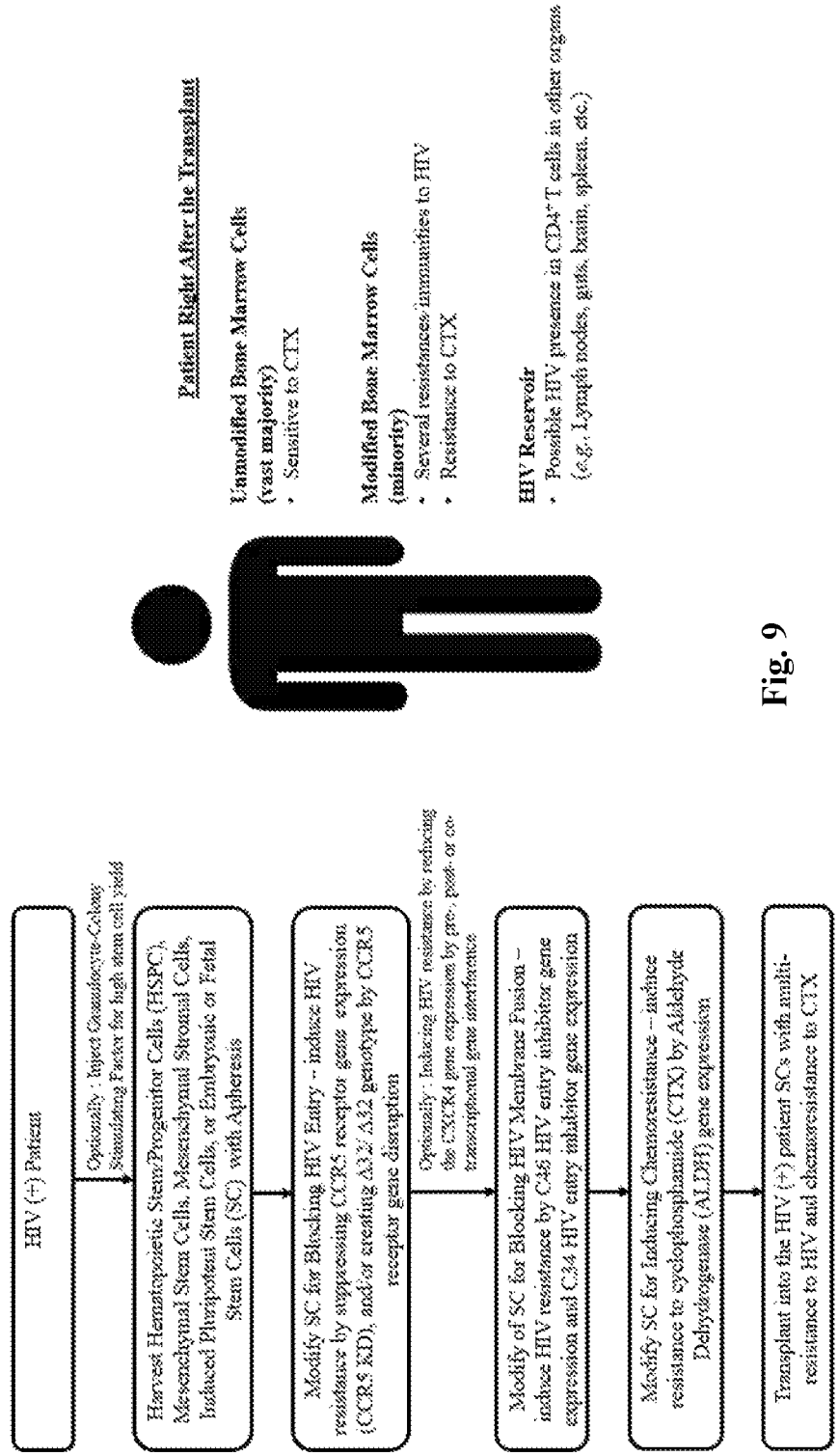
FIG. 9 depicts a non-limiting schematic of a study design for transplanting cells with multi-resistance to HIV and chemoresistance to CTX into an HIV$^+$ patient according to one embodiment of the present disclosure.
Figure 10:
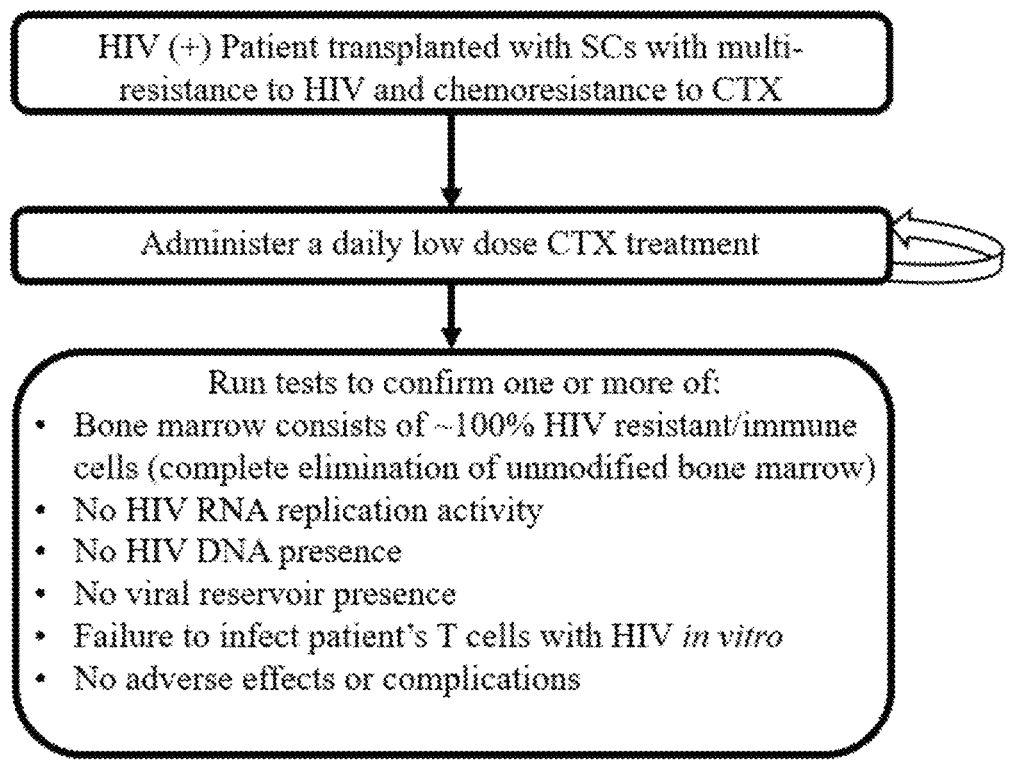
FIG. 10 depicts a non-limiting schematic of a study design treating an HIV$^-$ patient with daily CTX after transplanting cells having multi-resistance to HIV and chemoresistance to CTX to the patient. It is contemplated that the same study design can be performed on an HIV subject to prevent HIV.
Figure 11:
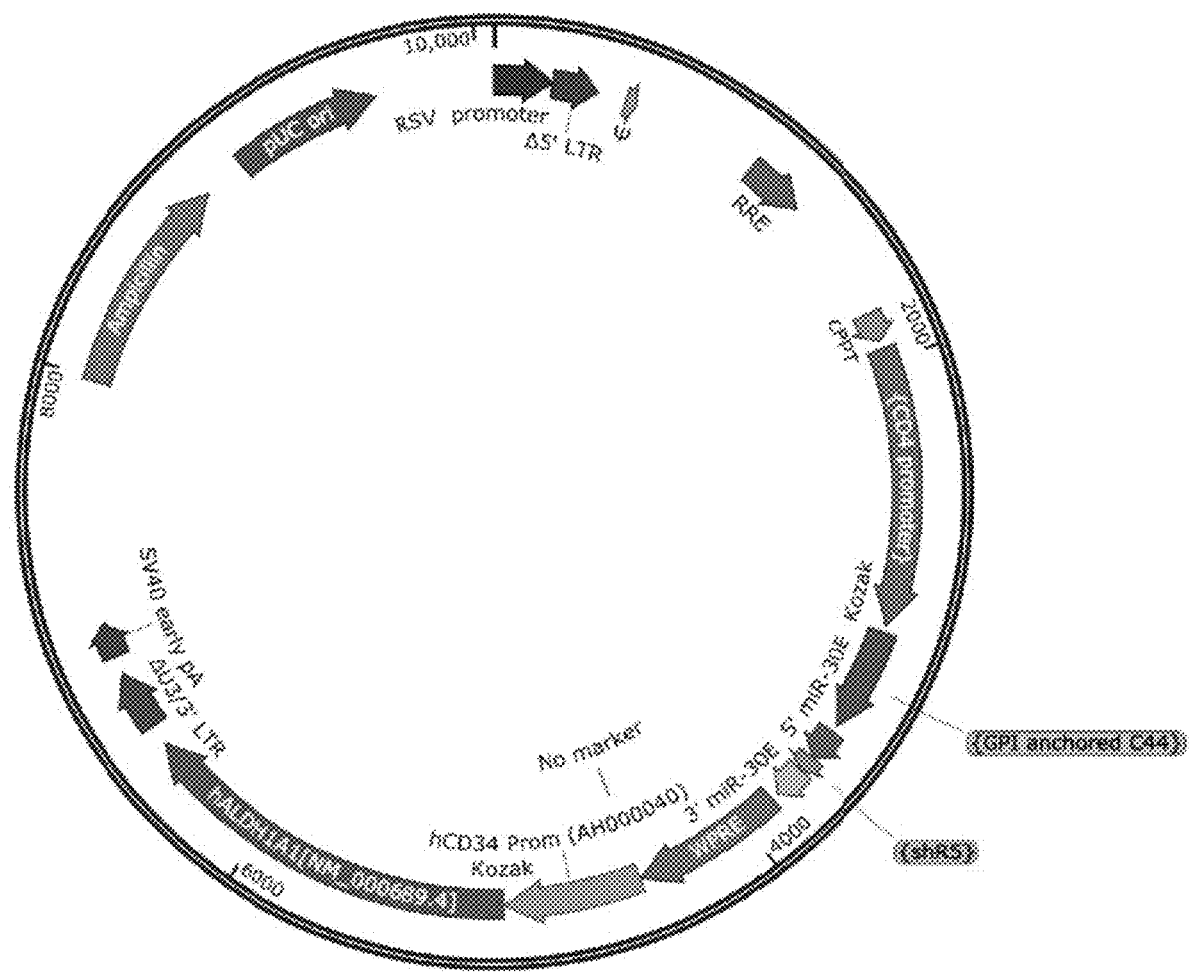
FIG. 11 depicts a non-limiting schematic of a lentiviral vector according to one embodiment of the present disclosure.
Figure 12:
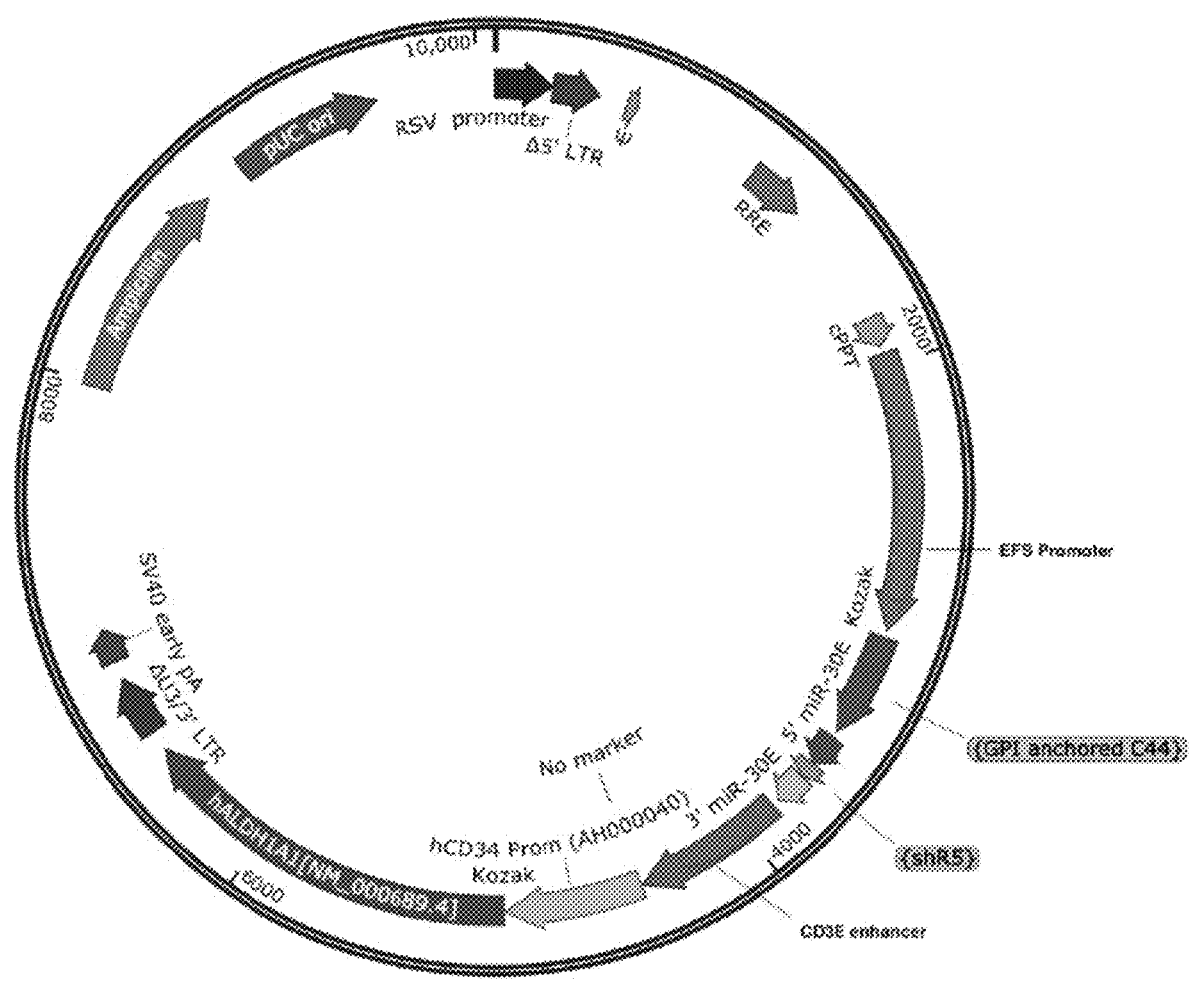
FIG. 12 depicts a non-limiting schematic of a lentiviral vector according to one embodiment of the present disclosure.

In some embodiments, after the infusion of the modified cells, a non-myeloblative dose of the chemotherapeutic, such as cyclophosphamide is administered. In some emboidments, the dosage is a dose of 50-200 mg and is given daily. In some embodiments, the non-myeloablative dose of cyclophosphamide is from about 0.15 mg/kg/day to less than 2.5 mg/kg/day, from about 0.4 mg/kg/day to about 1.7 mg/kg/day, or from about 0.8 mg/kg/day to about 1.5 mg/kg/day. In some embodiments, the non-myeloablative dose of cyclophosphamide is about 0.15 mg/kg/day, about 0.2 mg/kg/day, about 0.25 mg/kg/day, about 0.3 mg/kg/day, about 0.35 mg/kg/day, about 0.4 mg/kg/day, about 0.45 mg/kg/day, about 0.5 mg/kg/day, about 0.55 mg/kg/day, about 0.6 mg/kg/day, about 0.65 mg/kg/day, about 0.7 mg/kg/day, about 0.75 mg/kg/day, about 0.8 mg/kg/day, about 0.85 mg/kg/day, about 0.9 mg/kg/day, about 0.95 mg/kg/day, about 1.0 mg/kg/day, about 1.1 mg/kg/day, about 1.2 mg/kg/day, about 1.3 mg/kg/day, about 1.4 mg/kg/day, about 1.5 mg/kg/day, about 1.6 mg/kg/day, about 1.7 mg/kg/day, about 1.8 mg/kg/day, about 1.9 mg/kg/day, about 2.0 mg/kg/day, about 2.1 mg/kg/day, about 2.2 mg/kg/day, about 2.3 mg/kg/day, or about 2.4 mg/kg/day. In some embodiments, the non-myeloablativedose of cyclophosphamide is about 1.3 mg/kg/day. In some embodiments, the non-myeloablative dose of cyclophosphamide is from about 0.8 mg/kg/day to about 1.6 mg/kg/day, about 0.8 mg/kg/day, about 0.98 mg/kg/day, about 1.3 mg/kg/day, about 1.5 mg/kg/day, or about 1.6 mg/kg/day. In some embodiments, the non-myeloablative dose of cyclophosphamide is about 0.5 to about 2 mg/kg/day. The dose can be administered as provided for herein. Without being bound to any particular theory, the daily oral cyclophosphamide to facilitate the engraftment increase of the gene modified bone marrow cells. It is contemplated that the patient can be HIV⁺ at the time the modified CD34⁺ cells are infused, in which case the cells are functioning to treat and/or cure HIV, or the patient can be HIV⁻ at the time the modified CD34⁺ cells are infused, in which case the cells are functioning to prevent a future HIV infection. A non-limiting schematic for treating an HIV⁺ patient is provided in FIG. 9 and FIG. 10, but it is to be understood that the patient could also be HIV⁻.

In some embodiments, the subject is also treated Fludarabine prior to the infusion of the modified cells. In some embodiments, on day 2 after collection (or day −5 before transplant), the patients are treated with fludarabine (15 mg/m²) for 5 days (until day −1 before the transplant). In some embodiments in the place of fludarabine, on day −1 before the transplant patients can be treated with 4 mg/kg busulfan. In some embodiments, the patients are treated day −2 before the transplant with a single dose of 1000 mg/m2 cyclophosphamide. However, after the infusion of the cells, the subject is treated with a non-myeloablative dose of cyclophosphamide as provided for herein.

As described herein, the vector can also comprise other expression cassettes including those that express for shCCR5 or a fusion inhibitor, such as C44, C46 or others as described herein. The fusion inhibitor can be a fusion of a GPI anchor and the HIV fusion inhibitor. In some embodiments, the fusion inhibitor is encoded by a nucleic acid sequence of SEQ ID NO: 3. In some embodiments, the fusion inhibitor is a protein comprising the amino acid sequence of SEQ ID NO: 11. In some embodiments, the fusion inhibitor is encoded by a nucleic acid sequence of SEQ ID NO: 14. In some embodiments, the fusion inhibitor is a protein comprising the amino acid sequence of SEQ ID NO: 15. In some embodiments, the fusion inhibitor is anchored to the membrane by a GPI anchor. In some embodiments, the anchor is encoded by a nucleic acid molecule comprising the sequence of SEQ ID NO: 16. In some embodiments, the anchor comprises a sequence of SEQ ID NO: 17. In some embodiments, the fusion-anchor protein comprises a IgG hinge region. In some embodiments, the IgG hinge region is IgG3. In some embodiments, the fusion inhibitor protein comprises the sequence of SEQ ID NO: 19. In some embodiments, the fusion inhibitor protein is encoded for by a nucleic acid molecule comprising the sequence of SEQ ID NO: 18. In some embodiments, the anchor is GP41.

In some embodiments, the fusion inhibitor is put under the control of a different promoter than that of the ALDH1 promoter. In some embodiments, the promoter is a EFS promoter. In some embodiments, the promoter is a CD4 promoter, such as the one described herein.

In some embodiments, vector that is transduced into the cells as provided herein expressed an antisense molecule that reduces or inhibits the expression of CCR5. In some embodiments, vector encodes a shCCR5 inhibitor molecule. In some embodiments, the lentiviral vector encodes for a hCCR5 shRNA sense sequence of SEQ ID NO: 6, or the complement thereof, and/or the hCCR5 shRNA antisense sequence of SEQ ID NO: 7, or the complement thereof. In some embodiments, the sequences may also be in the reverse orientation. In some embodiments, the vector comprises a mir30 expression cassette. In some embodiments, the mir30 expression cassette encodes for the hCCR5 shRNA. In some embodiments, the mir30 construct comprises the sequence of SEQ ID NO: 13. The antisense molecule that can be used to inhibit CCR5 expression is a non-limiting example and other antisense molecules targeting CCR5 can be used.

Accordingly, in some embodiments, nucleic acid molecules are provided comprising the sequence of SEQ ID NO: 6, SEQ ID NO: 7, and/or SEQ ID NO: 13.

In some embodiments, the present disclosure provides for proteins comprising SEQ ID NO: 10, SEQ ID NO: 11, SEQ ID NO: 14, SEQ ID NO: 17, SEQ ID NO: 18, and/or SEQ ID NO: 19.

In some embodiments, nucleic acid molecules are provided, wherein the nucleic acid molecule comprises SEQ ID NO 1, or a variant thereof, SEQ ID NO: 3, or a variant thereof, SEQ ID NO: 6, or a variant thereof, SEQ ID NO: 7, or a variant thereof, SEQ ID NO: 13, or a variant thereof, SEQ ID N: 14, or a variant thereof, SEQ ID NO: 16, or a variant thereof, SEQ ID NO: 18, or a variant thereof, or any combination thereof. In some embodiments, the nucleic acid molecules comprises SEQ ID NO: 1, or a variant thereof, SEQ ID NO: 6, or a variant thereof, SEQ ID NO: 7, or a variant thereof, and one or more of SEQ ID NO: 3, SEQ ID NO: 14, and SEQ ID NO: 18. In some embodiments, nucleic acid molecules are provided that encode for proteins comprising SEQ ID NO: 2 and one or more of SEQ ID NO: 11, SEQ ID NO: 15, and SEQ ID NO: 19.

In some embodiments, the present disclosure provides for a nucleic acid molecule encoding for ALDH1, or a variant thereof, a shCCR5 molecule, or a variant thereof, and/or a fusion inhibitor, including anchored fusion inhibitors.

In some embodiments, a single nucleic acid molecule, such as a single vector, is used to encode for or express each of the nucleic acid molecules or proteins provided herein. In some embodiments, a single lentivirus comprises the nucleic acid sequences provided for herein. In some embodiments, a lentivirus is provided that comprises a single expression construct that encodes for each of ALDH1, or a variant thereof, a shCCR5 molecule, or a variant thereof, and/or a fusion inhibitor. Non-limiting examples of vectors comprising the various elements described herein are illustrated in FIGS. 4, 5, 6, 11, and 12. The promoters and response elements that operably connect the nucleic acid molecules that encode for ALDH1, shCCR5, and the fusion inhibitor (including anchored fusion inhibitor) are non-limiting and other promoters and response elements can be used. One of skill in the art would understand that the different promoters illustrated can be swapped with one another.

Non-limiting examples of nucleic acid sequences that can be used as viral vectors or the basis to form the lentivirus include those, for example, that comprise SEQ ID NO: 2, 4, and 5.

In some embodiments, the nucleic acid molecule comprises a 5' LTR and a 3' LTR that flanks the nucleic acid molecule encoding for ALDH1, shCCR5, and or the fusion inhibitor protein. For the avoidance of doubt, the shCCR5 sequences and the fusion inhibitor sequences can be swapped out for other sequences of interest that would be used to be co-expressed with ALDH1. Thus, in some embodiments, the nucleic acid molecule comprises a sequence encoding for ALDH1 and a sequence of interest, which can be for example, any other protein, antisense, miRNA, or other nucleic acid molecule that is desired to be expressed in the bone marrow or the cells types provided for herein.

Accordingly, in some embodiments, methods are provided comprising administering to an individual cells expressing ALDH1 and a molecule of interest and administering to the subject a non-myeloablative dose of a chemotherapeutic (e.g. cyclophosphamide).

In some embodiments, method of treating HIV in a subject are provdied, the method comprising administering to the subject a population of cells heterologously expressing ALDH1 and one of: i) a heterologous nucleotide molecule encoding for at least one HIV co-receptor mutant, a mutation or plurality of mutations of at least one HIV co-receptor, at least one HIV fusion inhibitor, a molecule that reduces the expression of a HIV co-receptor, or any combination thereof. In some embodiments, the methods comprise administering at least one non-myeloablative dose of a chemotherapeutic agent. In some embodiments, the cells are autologous to the subject. In some embodiments, the cells are allogenic to the subject. In some embodmients, cells express shCCR5, shCXCR4, and/or a C-peptide fusion inhibitor. In some embodiments, the cell comprises a nucleic acid molecule comprising a sequence of 1, 3, 6, 7, 8, 9, 12, 13, 14, 16, 18, or any combination thereof. In some embodiments, the cell comprises a nucleic acid molecule that encodes for a sequence of SEQ ID NO: 10, 11, 6, 7, 13, 15, 17, 19, or any combination thereof. In some embodiments, the cell is CD34+ and/or CD4+, or as otherwise as provided herein.

In some embodiments, methods of expressing a molecule of interest in a subject, the method comprising administering to the subject a cell that heterologously expresses ALDH1 and the molecule of interest; and administering a non-myeloablative dose of cyclophosphamide. In some embodiments, the cell is CD34+ and/or CD4+, or as otherwise as provided herein. In some embodiments, the molecule of interest is one that reduces expression of the CCR5; reduces expression of the CXCR4; encodes for the expression of a C-peptide fusion inhibitor; or any combination thereof. In some embodiments, the molecule of interest that reduces expression of the CCR5 is shCCR5. In some embodiments, the molecule comprises a nucleic acid molecule comprising or encoding for SEQ ID NO: 6 and/or SEQ ID NO: 7. In some embodiments, the C-peptide fusion inhibitor comprises a sequence of SEQ ID NO: 11, 15, 19, or any combination thereof.

It is to be understood that various sequences are provided for herein. In addition to the exact sequence, sequences that are variants of the discloses sequences are also provided. In some embodiments, sequence that have at least, about, or exactly, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99 percent homology or identity to the stated sequence are provided. Those of skill in the art readily understand how to determine the homology of two proteins or nucleic acids. For example, the homology can be calculated after aligning the two sequences so that the homology is at its highest level. In some embodiments, calculating homology can be performed by published algorithms. Optimal alignment of sequences for comparison may be conducted by the local homology algorithm of Smith and Waterman Adv. Appl. Math. 2: 482 (1981), by the homology alignment algorithm of Needleman and Wunsch, J. MoL Biol. 48: 443 (1970), by the search for similarity method of Pearson and Lipman, Proc. Natl. Acad. Sci. U.S.A. 85: 2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by inspection. The same types of homology can be obtained for nucleic acids by for example the algorithms disclosed in Zuker, M. Science 244:48-52, 1989, Jaeger et al. Proc. Natl. Acad. Sci. USA 86:7706-7710, 1989, Jaeger et al. Methods Enzymol. 183:281-306, 1989 which are herein incorporated by reference for at least material related to nucleic acid alignment. Websites maintained by the National Center for Biotechnology Information can be used to align two sequences, for example, using Blastn or BlastP using the default settings.

For example, as used herein, a sequence recited as having a particular percent homology to another sequence refers to sequences that have the recited homology as calculated by any one or more of the calculation methods described above. For example, a first sequence has 80 percent homology, as defined herein, to a second sequence if the first sequence is calculated to have 80 percent homology to the second sequence using the Zuker calculation method even if the first sequence does not have 80 percent homology to the second sequence as calculated by any of the other calculation methods. As another example, a first sequence has 80 percent homology, as defined herein, to a second sequence if the first sequence is calculated to have 80 percent homology to the second sequence using both the Zuker calculation method and the Pearson and Lipman calculation method even if the first sequence does not have 80 percent homology to the second sequence as calculated by the Smith and Waterman calculation method, the Needleman and Wunsch calculation method, the Jaeger calculation methods, or any of the other calculation methods. As yet another example, a first sequence has 80 percent homology, as defined herein, to a second sequence if the first sequence is calculated to have 80 percent homology to the second sequence using each of calculation methods (although, in practice, the different calculation methods will often result in different calculated homology percentages).

Cells and Compositions

Provided herein in certain embodiments are chemotherapeutic-resistant modified cells as described above with regard to the disclosed methods, and the use of these cells in the disclosed methods. Also provided are methods of generating these cells by incorporating one or more modifications that confer chemotherapeutic resistance into a suitable cell, and, optionally, incorporating one or more additional modifications unrelated to chemotherapeutic resistance, e.g., additional HIV/diseas-specific modifications.

Also provided herein in certain embodiments are compositions, including compositions for use in the methods provided herein, comprising at least one chemotherapeutic-resistant modified cell as provided herein. In some embodiments, the composition further comprises a pharmaceutically acceptable excipient, diluent, carrier, or any combination thereof.

The composition may comprise a pharmaceutically acceptable excipient, a pharmaceutically acceptable salt, diluents, carriers, vehicles and such other inactive agents well known to the skilled artisan. Vehicles and excipients commonly employed in pharmaceutical preparations include, for example, talc, gum Arabic, lactose, starch, magnesium stearate, cocoa butter, aqueous or non-aqueous solvents, oils, paraffin derivatives, glycols, etc. Solutions can be prepared using water or physiologically compatible organic solvents such as ethanol, 1,2-propylene glycol, polyglycols, dimethylsulfoxide, fatty alcohols, triglycerides, partial esters of glycerine and the like. Compositions may be prepared using conventional techniques that may include sterile isotonic saline, water, 1,3-butanediol, ethanol, 1,2-propylene glycol, polyglycols mixed with water, Ringer's solution, etc. In one aspect, a coloring agent is added to facilitate in locating and properly placing the composition to the intended treatment site.

Compositions may include a preservative and/or a stabilizer. Non-limiting examples of preservatives include methyl-, ethyl-, propyl-parabens, sodium benzoate, benzoic acid, sorbic acid, potassium sorbate, propionic acid, benzalkonium chloride, benzyl alcohol, thimerosal, phenylmercurate salts, chlorhexidine, phenol, 3-cresol, quaternary ammonium compounds (QACs), chlorbutanol, 2-ethoxyethanol, and imidurea.

To control tonicity, the composition can comprise a physiological salt, such as a sodium salt. Sodium chloride (NaCl) is preferred, which may be present at between 1 and 20 mg/ml. Other salts that may be present include potassium chloride, potassium dihydrogen phosphate, disodium phosphate dehydrate, magnesium chloride and calcium chloride.

Compositions may include one or more buffers. Typical buffers include: a phosphate buffer; a Tris buffer; a borate buffer; a succinate buffer; a histidine buffer; or a citrate buffer. Buffers will typically be included at a concentration in the 5-20 mM range. The pH of a composition will generally be between 5 and 8, and more typically between 6 and 8 e.g. between 6.5 and 7.5, or between 7.0 and 7.8.

In some embodiments, the composition may include a cryoprotectant agent. Non-limiting examples of cryoprotectant agents include a glycol (e.g., ethylene glycol, propylene glycol, and glycerol), dimethyl sulfoxide (DMSO), formamide, sucrose, trehalose, dextrose, and any combinations thereof.

In one embodiment, the cell is part of a population of cultured cells (i.e., in vitro). In another embodiment, the cell is part of a population of cells of a subject (i.e., in vivo). For example, the modified cell and/or non-myeloablative dose of a chemotherapeutic agent may be delivered to a cell in vivo or a population of cells in vivo that form a tissue or organ in a subject for the purpose of treating or preventing HIV or the disease of interest. Alternatively, the modified cells and/or a non-myeloablative dose of a chemotherapeutic agent may be delivered to a cultured cell or a population of cultured cells for the purpose of conducting experiments to study its effect on a particular type of cell.

The composition can be included in an implantable device. Suitable implantable devices contemplated by this invention include intravascular stents (e.g., self-expandable stents, balloon-expandable stents, and stent-grafts), scaffolds, grafts, and the like. Such implantable devices can be coated on at least one surface, or impregnated, with a composition capable of treating or preventing HIV or other disease.

Sequences are referenced herein and can refer to the sequences in the following table or equivalents thereof:

| SEQ ID NO: | Name | Sequence |
|---|---|---|
| 1 | hALDH1 cDNA | ATGTCATCCTCAGGCACGCCAGACTTACCTGTCCTACTCACCGATTT GAAGATTCAATATACTAAGATCTTCATAAACAATGAATGGCATGATT CAGTGAGTGGCAAGAAATTTCCTGTCTTTAATCCTGCAACTGAGGAG GAGCTCTGCCAGGTAGAAGAAGGAGATAAGGAGGATGTTGACAAGGC AGTGAAGGCCGCAAGACAGGCTTTTCAGATTGGATCCCCGTGGCGTA CTATGGATGCTTCCGAGAGGGGCGACTATTATACAAGTTGGCTGAT TTAATCGAAAGAGATCGTCTGCTGCTGGCGACAATGGAGTCAATGAA TGGTGGAAAACTCTATTCCAATGCATATCTGAATGATTTAGCAGGCT GCATCAAAACATTGCGCTACTGTGCAGGTTGGGCTGACAAGATCCAG GGCCGTACAATACCAATTGATGGAAATTTTTTTACATATACAAGACA TGAACCTATTGGTGTATGTGGCCAAATCATTCCTTGGAATTTCCCGT TGGTTATGCTCATTTGGAAGATAGGGCCTGCACTGAGCTGTGGAAAC ACAGTGGTTGTCAAACCAGCAGAGCAAACTCCTCTCACTGCTCTCCA CGTGGCATCTTTAATAAAAGAGGCAGGGTTTCCTCCTGGAGTAGTGA ATATTGTTCCTGGTTATGGGCCTACAGCAGGGGCAGCCATTTCTTCT CACATGGATATAGACAAAGTAGCCTTCACAGGATCAACAGAGGTTGG CAAGTTGATCAAAGAAGCTGCCGGGAAAAGCAATCTGAAGAGGGTGA CCCTGGAGCTTGGAGGAAAGAGCCCTTGCATTGTGTTAGCTGATGCC GACTTGGACAATGCTGTTGAATTTGCACACCATGGGGTATTCTACCA CCAGGGCCAGTGTTGTATAGCCGCATCCAGGATTTTTGTGGAAGAAT CAATTTATGATGAGTTTGTTCGAAGGAGTGTTGAGCGGGCTAAGAAG TATATCCTTGGAAATCCTCTGACCCCAGGAGTCACTCAAGGCCCTCA GATTGACAAGGAACAATATGATAAAATACTTGACCTCATTGAGAGTG GGAAGAAAGAAGGGGCCAAACTGGAATGTGGAGGAGGCCCGTGGGGG AATAAAGGCTACTTTGTCCAGCCCACAGTGTTCTCTAATGTTACAGA TGAGATGCGCATTGCCAAAGAGGAGATTTTTGGACCAGTGCAGCAAA TCATGAAGTTTAAATCTTTAGATGACGTGATCAAAAGAGCAAACAAT ACTTTCTATGGCTTATCAGCAGGAGTGTTTACCAAAGACATTGATAA AGCCATAACAATCTCCTCTGCTCTGCAGGCAGGAACAGTGTGGGTGA ATTGCTATGGCGTGGTAAGTGCCCAGTGCCCCTTTGGTGGATTCAAG ATGTCTGGAAATGGAAGAGAACTGGGAGAGTACGGTTTCCATGAATA TACAGAGGTCAAAACAGTCACAGTGAAAATCTCTCAGAAGAACTCA |
| 10 | hALDH1 protein | MSSSGTPDLPVLLTDLKIQYTKIFINNEWHDSVSGKKFPVFNPAIEE ELCQVEEGDKEDVDKAVKAARQAFQIGSPWRTMDASERGRLLYKLAD LIERDRLLLATMESMNGGKLYSNAYLNDLAGCIKTLRYCAGWADKIQ GRTIPIDGNFFTYTRHEPIGVCGQIIPWNFPLVMLIWKIGPALSCGN TVVVKPAEQTPLTALHVASLIKEAGFPPGVVNIVPGYGPTAGAAISS HMDIDKVAFTGSIEVGKLIKEAAGKSNLKRVTLELGGKSPCIVLADA DLDNAVEFAHHGVFYHQGQCCIAASRIFVEESIYDEFVRRSVERAKK YILGNPLTPGVTQGPQIDKEQYDKILDLIESGKKEGAKLECGGGPWG NKGYFVQPTVFSNVTDEMRIAKEEIFGPVQQIMKFKSLDDVIKRANN TFYGLSAGVFTKDIDKAITISSALQAGTVWVNCYGVVSAQCPFGGFK MSGNGRELGEYGFHEYIEVKTVTVKISQKNS |
| 2 | pLV-Puro-EF1A-hALDH1A1:T2A:EGFP | AATGTAGTCTTATGCAATACTCTTGTAGTCTTGCAACATGGTAACGA TGAGTTAGCAACATGCCTTACAAGGAGAGAAAAAGCACCGTGCATGC CGATTGGTGGAAGTAAGGTGGTACGATCGTGCCTTATTAGGAAGGCA ACAGACGGGTCTGACATGGATTGGACGAACCACTGAATTGCCGCATT GCAGAGATATTGTATTTAAGTGCCTAGCTCGATACATAAACGGGTCT CTCTGGTTAGACCAGATCTGAGCCTGGGAGCTCTCTGGCTAACTAGG GAACCCACTGCTTAAGCCTCAATAAAGCTTGCCTTGAGTGCTTCAAG TAGTGTGTGCCCGTCTGTTGTGTGACTCTGGTAACTAGAGATCCCTC AGACCCTTTTAGTCAGTGTGGAAAATCTCTAGCAGTGGCGCCCGAAC AGGGACTTGAAAGCGAAAGGGAAACCAGAGGAGCTCTCTCGACGCAG GACTCGGCTTGCTGAAGCGCGCACGGCAAGAGGCGAGGGGCGGCGAC TGGTGAGTACGCCAAAATTTTGACTAGCGGAGGCTAGAAGGAGAGA GATGGGTGCGAGAGCGTCAGTATTAAGCGGGGGAGAATTAGATCGCG ATGGGAAAAATTCGGTTAAGGCCAGGGGGAAAGAAAAAATATAAAT TAAAACATATAGTATGGGCAAGCAGGGAGCTAGAACGATTCGCAGTT AATCCTGGCCTGTTAGAAACATCAGAAGGCTGTAGACAAATACTGGG ACAGCTACAACCATCCCTTCAGACAGGATCAGAAGAACTTAGATCAT TATATAATACAGTAGCAACCCTCTATTGTGTGCATCAAAGGATAGAG ATAAAAGACACCAAGGAAGCTTTAGACAAGATAGAGGAAGAGCAAAA CAAAAGTAAGACCACCGCACAGCAAGCGGCCGCTGATCTTCAGACCT GGAGGAGGAGATATGAGGGACAATTGGAGAAGTGAATTATATAAATA TAAAGTAGTAAAAATTGAACCATTAGGAGTAGCACCCACCAAGGCAA AGAAGAGTGGTGCAGAGAGAAAAAAGAGCAGTGGGAATAGGAGCT TTGTTCCTTGGGTTCTTGGGAGCAGCAGGAAGCACTATGGGCGCAGC GTCAATGACGCTGACGGTACAGGCCAGACAATTATTGTCTGGTATAG TGCAGCAGCAGAACAATTTGCTGAGGGCTATTGAGGCGCAACAGCAT CTGTTGCAACTCACAGTCTGGGGCATCAAGCAGCTCCAGGCAAGAAT |

| SEQ ID NO: Name | Sequence |
|---|---|
| | CCTGGCTGTGGAAAGATACCTAAAGGATCAACAGCTCCTGGGGATTT |
| | GGGGTTGCTCTGGAAAACTCATTTGCACCACTGCTGTGCCTTGGAAT |
| | GCTAGTTGGAGTAATAAATCTCTGGAACAGATTTGGAATCACACGAC |
| | CTGGATGGAGTGGGACAGAGAAATTAACAATTACACAAGCTTAATAC |
| | ACTCCTTAATTGAAGAATCGCAAACCAGCAAGAAAAGAATGAACAA |
| | GAATTATTGGAATTAGATAAATGGGCAAGTTTGTGGAATTGGTTTAA |
| | CATAACAAATTGGCTGTGGTATATAAAATTATTCATAATGATAGTAG |
| | GAGGCTTGGTAGGTTTAAGAATAGTTTTTGCTGTACTTTCTATAGTG |
| | AATAGAGTTAGGCAGGGATATTCACCATTATCGTTTCAGACCCACCT |
| | CCCAACCCCGAGGGGACCCGACAGGCCCGAAGGAATAGAAGAAGAAG |
| | GTGGAGAGAGAGACAGAGACAGATCCATTCGATTAGTGAACGGATCT |
| | CGACGGTATCGCTAGCTTTTAAAAGAAAAGGGGGGATTGGGGGGTAC |
| | AGTGCAGGGGAAGAATAGTAGACATAATAGCAACAGACATACAAAC |
| | TAAAGAATTACAAAAACAAATTACAAAAATTCAAATTTTACTAGTG |
| | ATTATCGGATCAACTTTGTATAGAAAAGTTGGGCTCCGGTGCCCGTC |
| | AGTGGGCAGAGCGCACATCGCCCACAGTCCCGAGAAGTTGGGGGGA |
| | GGGGTCGGCAATTGAACCGGTGCCTAGAGAAGGTGGCGCGGGGTAAA |
| | CTGGGAAAGTGATGTCGTGTACTGGCTCCGCCTTTTTCCCGAGGGTG |
| | GGGGAGAACCGTATATAAGTGCAGTAGTCGCCGTGAACGTTCTTTTT |
| | CGCAACGGGTTTGCCGCCAGAACACAGGTAAGTGCCGTGTGTGGTTC |
| | CCGCGGGCCTGGCCTCTTTACGGGTTATGGCCCTTGCGTGCCTTGAA |
| | TTACTTCCACCTGGCTGCAGTACGTGATTCTTGATCCCGAGCTTCGG |
| | GTTGGAAGTGGGTGGGAGAGTTCGAGGCCTTGCGCTTAAGGAGCCCC |
| | TTCGCCTCGTGCTTGAGTTGAGGCCTGGCCTGGGCGCTGGGGCCGCC |
| | GCGTGCGAATCTGGTGGCACCTTCGCGCCTGTCTCGCTGCTTTCGAT |
| | AAGTCTCTAGCCATTTAAAATTTTTGATGACCTGCTGCGACGCTTTT |
| | TTTCTGGCAAGATAGTCTTGTAAATGCGGGCCAAGATCTGCACACTG |
| | GTATTTCGGTTTTTGGGGCCGCGGGCGGCGACGGGGCCCGTGCGTCC |
| | CAGCGCACATGTTCGGCGAGGCGGGGCCTGCGAGCGCGGCCACCGAG |
| | AATCGGACGGGGGTAGTCTCAAGCTGGCCGGCCTGCTCTGGTGCCTG |
| | GTCTCGCGCCGCCGTGTATCGCCCCGCCCTGGGCGGCAAGGCTGGCC |
| | CGGTCGGCACCAGTTGCGTGAGCGGAAAGATGGCCGCTTCCCGGCCC |
| | TGCTGCAGGGAGCTCAAAATGGAGGACGCGGCGCTCGGGAGAGCGGG |
| | CGGGTGAGTCACCCACACAAAGGAAAAGGGCCTTTCCGTCCTCAGCC |
| | GTCGCTTCATGTGACTCCACGGAGTACCGGGCGCCGTCCAGGCACCT |
| | CGATTAGTTCTCGAGCTTTTGGAGTACGTCGTCTTTAGGTTGGGGGG |
| | AGGGGTTTTATGCGATGGAGTTTCCCCACACTGAGTGGGTGGAGACT |
| | GAAGTTAGGCCAGCTTGGCACTTGATGTAATTCTCCTTGGAATTTGC |
| | CCTTTTTGAGTTTGGATCTTGGTTCATTCTCAAGCCTCAGACAGTGG |
| | TTCAAAGTTTTTTTCTTCCATTTCAGGTGTCGTGACAAGTTTGTACA |
| | AAAAAGCAGGCTGCCACCATGTCATCCTCAGGCACGCCAGACTTACC |
| | TGTCCTACTCACCGATTTGAAGATTCAATATACTAAGATCTTCATAA |
| | ACAATGAATGGCATGATTCAGTGAGTGGCAAGAAATTTCCTGTCTTT |
| | AATCCTGCAACTGAGGAGGAGCTCTGCCAGGTAGAAGAAGGAGATAA |
| | GGAGGATGTTGACAAGGCAGTGAAGGCCGCAAGACAGGCTTTTCAGA |
| | TTGGATCCCCGTGGCGTACTATGGATGCTTCCGAGAGGGGGCGACTA |
| | TTTATACAAGTTGGCTGATTTAATCGAAAGAGATCGTCTGCTGCTGGC |
| | GACAATGGAGTCAATGAATGGTGGAAAACTCTATTCCAATGCATATC |
| | TGAATGATTTAGCAGGCTGCATCAAAACATTGCGCTACTGTGCAGGT |
| | TGGGCTGACAAGATCCAGGGCCGTACAATACCAATTGATGGAAATTT |
| | TTTTACATATACAAGACATGAACCTATTGGTGTATGTGGCCAAATCA |
| | TTCCTTGGAATTTCCCGTTGGTTATGCTCATTTGGAAGATAGGGCCT |
| | GCACTGAGCTGTGGAAACACAGTGGTTGTCAAACCAGCAGAGCAAAC |
| | TCCTCTCACTGCTCTCCACGTGGCATCTTTAATAAAAGAGGCAGGGT |
| | TTCCTCCTGGAGTAGTGAATATTGTTCCTGGTTATGGGCCTACAGCA |
| | GGGGCAGCCATTTCTTCTCACATGGATATAGACAAAGTAGCCTTCAC |
| | AGGATCAACAGAGGTTGGCAAGTTGATCAAAGAAGCTGCCGGGAAAA |
| | GCAATCTGAAGAGGGTGACCCTGGAGCTTGGAGGAAAGAGCCCTTGC |
| | ATTGTGTTAGCTGATGCCGACTTGGACAATGCTGTTGAATTTGCACA |
| | CCATGGGGTATTCTACCACCAGGGCCAGTGTTGTATAGCCGCATCCA |
| | GGATTTTTGTGGAAGAATCAATTTATGATGAGTTTGTTCGAAGGAGT |
| | GTTGAGCGGGCTAAGAAGTATATCCTTGGAAATCCTCTGACCCCAGG |
| | AGTCACTCAAGGCCCTCAGATTGACAAGGAACAATATGATAAAATAC |
| | TTGACCTCATTGAGAGTGGGAAGAAAGAAGGGGCCAAACTGGAATGT |
| | GGAGGAGGCCCGTGGGGAATAAAGGCTACTTTGTCCAGCCCACAGT |
| | GTTCTCTAATGTTACAGATGAGATGCGCATTGCCAAAGAGGAGATTT |
| | TTGGACCAGTGCAGCAAATCATGAAGTTTAAATCTTTAGATGACGTG |
| | ATCAAAAGAGCAAACAATACTTTCTATGGCTTATCAGCAGGAGTGTT |
| | TACCAAAGACATTGATAAAGCCATAACAATCCTCTGCTCTGCAGG |
| | CAGGAACAGTGTGGGTGAATTGCTATGGCGTGGTAAGTGCCCAGTGC |
| | CCCTTTGGTGGATTCAAGATGTCTGGAAATGGAAGAGAACTGGGAGA |
| | GTACGGTTTCCATGAATATACAGAGGTCAAAACAGTCACAGTGAAAA |
| | TCTCTCAGAAGAACTCAGGAAGCGGAGAGGGCAGGGGAAGTCTTCTA |
| | ACATGCGGGACGTGGAGGAAAATCCCGGCCCCATGGTGAGCAAGGG |
| | CGAGGAGCTGTTCACCGGGGTGGTGCCCATCCTGGTCGAGCTGGACG |
| | GCGACGTAAACGGCCACAAGTTCAGCGTGTCCGGCGAGGGCGAGGGC |
| | GATGCCACCTACGGCAAGCTGACCCTGAAGTTCATCTGCACCACCGG |

| SEQ ID NO: Name | Sequence |
|---|---|
| | CAAGCTGCCCGTGCCCTGGCCCACCCTCGTGACCACCCTGACCTACG
GCGTGCAGTGCTTCAGCCGCTACCCCGACCACATGAAGCAGCACGAC
TTCTTCAAGTCGCCATGCCCGAAGGCTACGTCCAGGAGCGCACCAT
CTTCTTCAAGGACGACGGCAACTACAAGACCCGCGCCGAGGTGAAGT
TCGAGGGCGACACCCTGGTGAACCGCATCGAGCTGAAGGGCATCGAC
TTCAAGGAGGACGGCAACATCCTGGGGCACAAGCTGGAGTACAACTA
CAACAGCCACAACGTCTATATCATGGCCGACAAGCAGAAGAACGGCA
TCAAGGTGAACTTCAAGATCCGCCACAACATCGAGGACGGCAGCGTG
CAGCTCGCCGACCACTACCAGCAGAACACCCCCATCGGCGACGGCCC
CGTGCTGCTGCCCGACAACCACTACCTGAGCACCCAGTCCGCCCTGA
GCAAAGACCCCAACGAGAAGCGCGATCACATGGTCCTGCTGGAGTTC
GTGACCGCCGCGGGATCACTCTCGGCATGGACGAGCTGTACAAGTA
AACCCAGCTTTCTTGTACAAAGTGGTGATAATCGAATTCCGATAATC
AACCTCTGGATTACAAAATTTGTGAAAGATTGACTGGTATTCTTAAC
TATGTTGCTCCTTTTACGCTATGTGGATACGCTGCTTTAATGCCTTT
GTATCATGCTATTGCTTCCCGTATGGCTTTCATTTTCTCCTCCTTGT
ATAAATCCTGGTTGCTGTCTCTTTATGAGGAGTTGTGGCCCGTTGTC
AGGCAACGTGGCGTGGTGTGCACTGTGTTTGCTGACGCAACCCCCAC
TGGTTGGGGCATTGCCACCACCTGTCAGCTCCTTTCCGGGACTTTCG
CTTTCCCCCTCCCTATTGCCACGGCGGAACTCATCGCCGCCTGCCTT
GCCCGCTGCTGGACAGGGGCTCGGCTGTTGGGCACTGACAATTCCGT
GGTGTTGTCGGGAAGCTGACGTCCTTTCCATGGCTGCTCGCCTGTG
TTGCCACCTGGATTCTGCGCGGGACGTCCTTCTGCTACGTCCCTTCG
GCCCTCAATCCAGCGGACCTTCCTTCCCGCGGCCTGCTGCCGGCTCT
GCGGCCTCTTCCGCGTCTTCGCCTTCGCCCTCAGACGAGTCGGATCT
CCCTTTGGGCCGCCTCCCCGCATCGGGAATTCCCGCGGTTCGAATTC
TACCGGGTAGGGGAGGCGCTTTTCCCAAGGCAGTCTGGAGCATGCGC
TTTAGCAGCCCCGCTGGGCACTTGGCGCTACACAAGTGGCCTCTGGC
CTCGCACACATTCCACATCCACCGGTAGGCGCCAACCGGCTCCGTTC
TTTGGTGGCCCCTTCGCGCCACCTTCTACTCCTCCCCTAGTCAGGAA
GTTCCCCCCCGCCCGCAGCTCGCGTCGTGCAGGACGTGACAAATGG
AAGTAGCACGTCTCACTAGTCTCGTGCAGATGGACAGCACCGCTGAG
CAATGGAAGCGGGTAGGCCTTTGGGGCAGCGGCCAATAGCAGCTTTG
CTCCTTCGCTTTCTGGGCTCAGAGGCTGGGAAGGGGTGGGTCCGGGG
GCGGGCTCAGGGGCGGGCTCAGGGGCGGGCGGGCGCCCGAAGGTCC
TCCGGAGGCCCGGCATTCTGCACGCTTCAAAAGCGCACGTCTGCCGC
GCTGTTCTCCTCTTCCTCATCTCCGGGCCTTTCGACCTCACGTGGCC
ACCATGACCGAGTACAAGCCCACGGTGCGCCTCGCCACCCGCGACGA
CGTCCCCAGGGCCGTACGCACCCTCGCCGCCGCGTTCGCCGACTACC
CCGCCACGCGCCACACCGTCGATCCGGACCGCCACATCGAGCGGGTC
ACCGAGCTGCAAGAACTCTTCCTCACGCGCGTCGGGCTCGACATCGG
CAAGGTGTGGGTCGCGGACGACGGCGCCGCGGTGGCGGTCTGGACCA
CGCCGGAGAGCGTCGAAGCGGGGGCGGTGTTCGCCGAGATCGGCCCG
CGCATGGCCGAGTTGAGCGGTTCCCGGCTGGCCGCGCAGCAACAGAT
GGAAGGCCTCCTGGCGCCGCACCGGCCCAAGGAGCCCGCGTGGTTCC
TGGCCACCGTCGGCGTCTCGCCCGACCACCAGGGCAAGGGTCTGGGC
AGCGCCGTCGTGCTCCCCGGAGTGGAGGCGGCCGAGCGCGCCGGGGT
GCCCGCCTTCCTGGAGACCTCCGCGCCCCGCAACCTCCCCCTTCTACG
AGCGGCTCGGCTTCACCGTCACCGCCGACGTCGAGGTGCCCGAAGGA
CCGCGCACCTGGTGCATGACCCGCAAGCCCGGTGCCTGAGGTACCTT
TAAGACCAATGACTTACAAGGCAGCTGTAGATCTTAGCCACTTTTTA
AAAGAAAAGGGGGGACTGGAAGGGCTAATTCACTCCCAACGAAGACA
AGATCTGCTTTTTGCTTGTACTGGGTCTCTCTGGTTAGACCAGATCT
GAGCCTGGGAGCTCTCTGGCTAACTAGGGAACCCACTGCTTAAGCCT
CAATAAAGCTTGCCTTGAGTGCTTCAAGTAGTGTGTGCCCGTCTGTT
GTGTGACTCTGGTAACTAGAGATCCCTCAGACCCTTTTAGTCAGTGT
GGAAAATCTCTAGCAGTAGTAGTTCATGTCATCTTATTATTCAGTAT
TTATAACTTGCAAAGAAATGAATATCAGAGAGTGAGAGGAACTTGTT
TATTGCAGCTTATAATGGTTACAAATAAAGCAATAGCATCACAAATT
TCACAAATAAAGCATTTTTTTCACTGCATTCTAGTTGTGGTTTGTCC
AAACTCATCAATGTATCTTATCATGTCTGGCTCTAGCTATCCCGCCC
CTAACTCCGCCCATCCCGCCCCTAACTCCGCCCAGTTCCGCCCATTC
TCCGCCCCATGGCTGACTAATTTTTTTTATTTATGCAGAGGCCGAGG
CCGCCTCGGCCTCTGAGCTATTCCAGAAGTAGTGAGGAGGCTTTTTT
GGAGGCCTAGGGACGTACCCAATTCGCCCTATAGTGAGTCGTATTAC
GCGCGCTCACTGGCCGTCGTTTTACAACGTCGTGACTGGGAAAACCC
TGGCGTTACCCAACTTAATCGCCTTGCAGCACATCCCCCTTTCGCCA
GCTGGCGTAATAGCGAAGAGGCCCGCACCGATCGCCCTTCCCAACAG
TTGCGCAGCCTGAATGGCGAATGGACGCGCCCTGTAGCGGCGCATT
AAGCGCGGCGGGTGTGGTGGTTACGCGCAGCGTGACCGCTACACTTG
CCAGCGCCCTAGCGCCCGCTCCTTTCGCTTTCTTCCCTTCCTTTCTC
GCCACGTTCGCCGGCTTTCCCCGTCAAGCTCTAAATCGGGGGCTCCC
TTTAGGGTTCCGATTTAGTGCTTTACGGCACCTCGACCCCAAAAAAC
TTGATTAGGGTGATGGTTCACGTAGTGGGCCATCGCCCTGATAGACG
GTTTTTCGCCCTTTGACGTTGGAGTCCACGTTCTTTAATAGTGGACT
CTTGTTCCAAACTGGAACAACACTCAACCCTATCTCGGTCTATTCTT
TTGATTTATAAGGGATTTTGCCGATTTCGGCCTATTGGTTAAAAAAT |

| SEQ ID NO: | Name | Sequence |
|---|---|---|
|  |  | GAGCTGATTTAACAAAAATTTAACGCGAATTTTAACAAAATATTAAC<br>GCTTACAATTTAGGTGGCACTTTTCGGGGAAATGTGCGCGGAACCCC<br>TATTTGTTTATTTTTCTAAATACATTCAAATATGTATCCGCTCATGA<br>GACAATAACCCTGATAAATGCTTCAATAATATTGAAAAAGGAAGAGT<br>ATGAGTATTCAACATTTCCGTGTCGCCCTTATTCCCTTTTTTGCGGC<br>ATTTTGCCTTCCTGTTTTTGCTCACCCAGAAACGCTGGTGAAAGTAA<br>AAGATGCTGAAGATCAGTTGGGTGCACGAGTGGGTTACATCGAACTG<br>GATCTCAACAGCGGTAAGATCCTTGAGAGTTTTCGCCCCGAAGAACG<br>TTTTCCAATGATGAGCACTTTTAAAGTTCTGCTATGTGGCGCGGTAT<br>TATCCCGTATTGACGCCGGGCAAGAGCAACTCGGTCGCCGCATACAC<br>TATTCTCAGAATGACTTGGTTGAGTACTCACCAGTCACAGAAAAGCA<br>TCTTACGGATGGCATGACAGTAAGAGAATTATGCAGTGCTGCCATAA<br>CCATGAGTGATAACACTGCGGCCAACTTACTTCTGACAACGATCGGA<br>GGACCGAAGGAGCTAACCGCTTTTTTGCACAACATGGGGGATCATGT<br>AACTCGCCTTGATCGTTGGGAACCGGAGCTGAATGAAGCCATACCAA<br>ACGACGAGCGTGACACCACGATGCCTGTAGCAATGGCAACAACGTTG<br>CGCAAACTATTAACTGGCGAACTACTTACTCTAGCTTCCCGGCAACA<br>ATTAATAGACTGGATGGAGGCGGATAAAGTTGCAGGACCACTTCTGC<br>GCTCGGCCCTTCCGGCTGGCTGGTTTATTGCTGATAAATCTGGAGCC<br>GGTGAGCGTGGGTCTCGCGGTATCATTGCAGCACTGGGGCCAGATGG<br>TAAGCCCTCCCGTATCGTAGTTATCTACACGACGGGGAGTCAGGCAA<br>CTATGGATGAACGAAATAGACAGATCGCTGAGATAGGTGCCTCACTG<br>ATTAAGCATTGGTAACTGTCAGACCAAGTTTACTCATATATACTTTA<br>GATTGATTTAAAACTTCATTTTTAATTTAAAAGGATCTAGGTGAAGA<br>TCCTTTTTGATAATCTCATGACCAAAATCCCTTAACGTGAGTTTTCG<br>TTCCACTGAGCGTCAGACCCCGTAGAAAAGATCAAAGGATCTTCTTG<br>AGATCCTTTTTTTCTGCGCGTAATCTGCTGCTTGCAAACAAAAAAAC<br>CACCGCTACCAGCGGTGGTTTGTTTGCCGGATCAAGAGCTACCAACT<br>CTTTTTCCGAAGGTAACTGGCTTCAGCAGAGCGCAGATACCAAATAC<br>TGTTCTTCTAGTGTAGCCGTAGTTAGGCCACCACTTCAAGAACTCTG<br>TAGCACCGCCTACATACCTCGCTCTGCTAATCCTGTTACCAGTGGCT<br>GCTGCCAGTGGCGATAAGTCGTGTCTTACCGGGTTGGACTCAAGACG<br>ATAGTTACCGGATAAGGCGCAGCGGTCGGGCTGAACGGGGGGTTCGT<br>GCACACAGCCCAGCTTGGAGCGAACGACCTACACCGAACTGAGATAC<br>CTACAGCGTGAGCTATGAGAAAGCGCCACGCTTCCCGAAGAGAGAAA<br>GGCGGACAGGTATCCGGTAAGCGGCAGGGTCGGAACAGGAGAGCGCA<br>CGAGGGAGCTTCCAGGGGGAAACGCCTGGTATCTTTATAGTCCTGTC<br>GGGTTTCGCCACCTCTGACTTGAGCGTCGATTTTTGTGATGCTCGTC<br>AGGGGGGCGGAGCCTATGGAAAAACGCCAGCAACGCGGCCTTTTTAC<br>GGTTCCTGGCCTTTTGCTGGCCTTTTGCTCACATGTTCTTTCCTGCG<br>TTATCCCCTGATTCTGTGGATAACCGTATTACCGCCTTTGAGTGAGC<br>TGATACCGCTCGCCGCAGCCGAACGACCGAGCGCAGCGAGTCAGTGA<br>GCGAGGAAGCGGAAGAGCGCCCAATACGCAAACCGCCTCTCCCCGCG<br>CGTTGGCCGATTCATTAATGCAGCTGGCACGACAGGTTTCCCGACTG<br>GAAAGCGGGCAGTGAGCGCAACGCAATTAATGTGAGTTAGCTCACTC<br>ATTAGGCACCCCAGGCTTTACACTTTATGCTTCCGGCTCGTATGTTG<br>TGTGGAATTGTGAGCGGATAACAATTTCACACAGGAAACAGCTATGA<br>CCATGATTACGCCAAGCGCGCAATTAACCCTCACTAAAGGGAACAAA<br>AGCTGGAGCTGCAAGCTT |
| 3 | Membrane<br>Anchored<br>C46 Fusion<br>Inhibitor | ATGGGCGCCGGCGCCACCGGCAGAGCCATGGACGGCCCCAGACTGCT<br>GCTGCTGCTGCTGGGCGTGAGCCTGGGCGGCGCCAGAAGCTGGA<br>TGGAGTGGGACAGAGAGATCAACAACTACACCAGCCTGATCCTACAGC<br>CTGATCGAGGAGAGCCAGAACCAGCAGGAGAAGAACGAGCAGGAGCT<br>GCTGGAGCTGGACAAGTGGGCCAGCCTGTGGAACTGGTTCAGAAGCG<br>AGAGAAAGTGCTGCGTGGAGTGCCCCCCCTGCCCCGCCCCCCCGTG<br>GCCGGCCCCCTGATCGCCCTGGTGACCAGCGGCGCCCTGCTGGCCGT<br>GCTGGGCATCACCGGCTACTTCCTGATGAACAGAAGAAGCTGGAGCC<br>CCACCGGCGAGAGACTGGAGCTGGAGCCCTAA |
| 11 | Membrane<br>Anchored<br>C46 Fusion<br>Inhibitor<br>Protein | MGAGATGRAMDGPRULLLLLGVSLGGARSWIVIEWDREINNYTSLIH<br>SLIEESQNQQEKNEQELLELDKWASLWNWFRSERKCCVECPPCPAPP<br>VAGPLIALVTSGALLAVLGITGYFLMNRRSWSPTGERLELEP |
| 4 | pLV:<br>hALDH1A1:<br>T2A:<br>maC46:<br>shCCR5 | AATGTAGTCTTATGCAATACTCTTGTAGTCTTGCAACATGGTAACGA<br>TGAGTTAGCAACATGCCTTACAAGGAGAGAAAAAGCACCGTGCATGC<br>CGATTGGTGGAAGTAAGGTGGTACGATCGTGCCTTATTAGGAAGGCA<br>ACAGACGGGTCTGACATGGATTGGACGAACCACTGAATTGCCGCATT<br>GCAGAGATATTGTATTTAAGTGCCTAGCTCGATACATAAACGGGTCT<br>CTCTGGTTAGACCAGATCTGAGCCTGGGAGCTCTCTGGCTAACTAGG<br>GAACCCACTGCTTAAGCCTCAATAAAGCTTGCCTTGAGTGCTTCAAG<br>TAGTGTGTGCCCGTCTGTTGTGTGACTCTGGTAACTAGAGATCCCTC<br>AGACCCTTTTAGTCAGTGTGGAAAATCTCTAGCAGTGGCGCCCGAAC<br>AGGGACTTGAAAGCGAAAGGGAAACCAGAGGAGCTCTCTCGACGCAG<br>GACTCGGCTTGCTGAAGCGCGCACGGCAAGAGGCGAGGGGCGGCGAC |

| SEQ ID NO: Name | Sequence |
|---|---|
| | TGGTGAGTACGCCAAAAATTTTGACTAGCGGAGGCTAGAAGGAGAGA |
| | GATGGGTGCGAGAGCGTCAGTATTAAGCGGGGGAGAATTAGATCGCG |
| | ATGGGAAAAAATTCGGTTAAGGCCAGGGGGAAAGAAAAAATATAAAT |
| | TAAAACATATAGTATGGGCAAGCAGGGAGCTAGAACGATTCGCAGTT |
| | AATCCTGGCCTGTTAGAAACATCAGAAGGCTGTAGACAAATACTGGG |
| | ACAGCTACAACCATCCCTTCAGACAGGATCAGAAGAACTTAGATCAT |
| | TATATAATACAGTAGCAACCCTCTATTGTGTGCATCAAAGGATAGAG |
| | ATAAAAGACACCAAGGAAGCTTTAGACAAGATAGAGGAAGAGCAAAA |
| | CAAAAGTAAGACCACCGCACAGCAAGCGGCCGCTGATCTTCAGACCT |
| | GGAGGAGGAGATATGAGGGACAATTGGAGAAGTGAATTATATAAATA |
| | TAAAGTAGTAAAAATTGAACCATTAGGAGTAGCACCCACCAAGGCAA |
| | AGAGAAGAGTGGTGCAGAGAGAAAAAAGAGCAGTGGGAATAGGAGCT |
| | TTGTTCCTTGGGTTCTTGGGAGCAGCAGGAAGCACTATGGGCGCAGC |
| | GTCAATGACGCTGACGGTACAGGCCAGACAATTATTGTCTGGTATAG |
| | TGCAGCAGCAGAACAATTTGCTGAGGGCTATTGAGGCGCAACAGCAT |
| | CTGTTGCAACTCACAGTCTGGGGCATCAAGCAGCTCCAGGCAAGAAT |
| | CCTGGCTGTGGAAAGATACCTAAAGGATCAACAGCTCCTGGGGATTT |
| | GGGGTTGCTCTGGAAAACTCATTTGCACCACTGCTGTGCCTTGGAAT |
| | GCTAGTTGGAGTAATAAATCTCTGGAACAGATTTGGAATCACACGAC |
| | CTGGATGGAGTGGGACAGAGAAATTAACAATTACACAAGCTTAATAC |
| | ACTCCTTAATTGAAGAATCGCAAAACCAGCAAGAAAAGAATGAACAA |
| | GAATTATTGGAATTAGATAAATGGGCAAGTTTGTGGAATTGGTTTAA |
| | CATAACAAATTGGCTGTGGTATATAAAATTATTCATAATGATAGTAG |
| | GAGGCTTGGTAGGTTTAAGAATAGTTTTTGCTGTACTTTCTATAGTG |
| | AATAGAGTTAGGCAGGGATATTCACCATTATCGTTTCAGACCCACCT |
| | CCCAACCCCGAGGGGACCCGACAGGCCCGAAGGAATAGAAGAAGAAG |
| | GTGGAGAGAGAGACAGAGACAGATCCATTCGATTAGTGAACGGATCT |
| | CGACGGTATCGCTAGCTTTTAAAAGAAAAGGGGGGATTGGGGGGTAC |
| | AGTGCAGGGGAAAGAATAGTAGACATAATAGCAACAGACATACAAAC |
| | TAAAGAATTACAAAAACAAATTACAAAAATTCAAAATTTTACTAGTG |
| | ATTATCGGATCAACTTTGTATAGAAAAGTTGGAATTCGAACGCTGAC |
| | GTCATCAACCCGCTCCAAGGAATCGCGGGCCCAGTGTCACTAGGCGG |
| | GAACACCCAGCGCGCGTGCGCCCTGGCAGGAAGATGGCTGTGAGGGA |
| | CAGGGGAGTGGCGCCCTGCAATATTTGCATGTCGCTATGTGTTCTGG |
| | GAAATCACCATAAACGTGAAATGTCTTTGGATTTGGGAATCTTATAA |
| | GTTCTGTATGAGACCACCGGGTCCATACAGTCAGTATCAATTCTCGA |
| | GAATTGATACTGACTGTATGGATTTTTGGATCCCAAGTTTGTACAAA |
| | AAAGCAGGCTGGCTCCGGTGCCCGTCAGTGGGCAGAGCGCACATCGC |
| | CCACAGTCCCCGAGAAGTTGGGGGGAGGGGTCGGCAATTGAACCGGT |
| | GCCTAGAGAAGGTGGCGCGGGGTAAACTGGGAAAGTGATGTCGTGTA |
| | CTGGCTCCGCCTTTTTCCCGAGGGTGGGGGAGAACCGTATATAAGTG |
| | CAGTAGTCGCCGTGAACGTTCTTTTTCGCAACGGGTTTGCCGCCAGA |
| | ACACAGGTAAGTGCCGTGTGTGGTTCCCGCGGGCCTGGCCTCTTTAC |
| | GGGTTATGGCCCTTGCGTGCCTTGAATTACTTCCACCTGGCTGCAGT |
| | ACGTGATTCTTGATCCCGAGCTTCGGGTTGGAAGTGGGTGGGAGAGT |
| | TCGAGGCCTTGCGCTTAAGGAGCCCCTTCGCCTCGTGCTTGAGTTGA |
| | GGCCTGGCCTGGGCGCTGGGGCCGCCGCGTGCGAATCTGGTGGCACC |
| | TTCGCGCCTGTCTCGCTGCTTTCGATAAGTCTCTAGCCATTTAAAAT |
| | TTTTGATGACCTGCTGCGACGCTTTTTTTCTGGCAAGATAGTCTTGT |
| | AAATGCGGGCCAAGATCTGCACACTGGTATTTCGGTTTTTGGGGCCG |
| | CGGGCGGCGACGGGGCCCGTGCGTCCCAGCGCACATGTTCGGCGAGG |
| | CGGGGCCTGCGAGCGCGGCCACCGAGAATCGGACGGGGGTAGTCTCA |
| | AGCTGGCCGGCCTGCTCTGGTGCCTGGTCTCGCGCCGCCGTGTATCG |
| | CCCCGCCCTGGGCGGCAAGGCTGGCCCGGTCGGCACCAGTTGCGTGA |
| | GCGGAAAGATGGCCGCTTCCCGGCCCTGCTGCAGGGAGCTCAAAATG |
| | GAGGACGCGGCGCTCGGGAGAGCGGGCGGGTGAGTCACCCACACAAA |
| | GGAAAAGGGCCTTTCCGTCCTCAGCCGTCGCTTCATGTGACTCCACG |
| | GAGTACCGGGCGCCGTCCAGGCACCTCGATTAGTTCTCGAGCTTTTG |
| | GAGTACGTCGTCTTTAGGTTGGGGGGAGGGGTTTTATGCGATGGAGT |
| | TTCCCCACACTGAGTGGGTGGAGACTGAAGTTAGGCCAGCTTGGCAC |
| | TTGATGTAATTCTCCTTGGAATTTGCCCTTTTTGAGTTTGGATCTTG |
| | GTTCATTCTCAAGCCTCAGACAGTGGTTCAAAGTTTTTTTCTTCCAT |
| | TTCAGGTGTCGTGAGCCACCATGTCATCCTCAGGCACGCCAGACTTA |
| | CCTGTCCTACTCACCGATTTGAAGATTCAATATACTAAGATCTTCAT |
| | AAACAATGAATGGCATGATTCAGTGAGTGGCAAGAAATTTCCTGTCT |
| | TTAATCCTGCAACTGAGGAGGAGCTCTGCCAGGTAGAAGAAGGAGAT |
| | AAGGAGGATGTTGACAAGGCAGTGAAGGCCGCAAGACAGGCTTTTCA |
| | GATTGGATCCCCGTGGCGTACTATGGATGCTTCCGAGAGGGGCGAC |
| | TATTATACAAGTTGGCTGATTTAATCGAAAGAGATCGTCTGCTGCTG |
| | GCGACAATGGAGTCAATGAATGGTGGAAAACTCTATTCCAATGCATA |
| | TCTGAATGATTTAGCAGGCTGCATCAAAACATTGCGCTACTGTGCAG |
| | GTTGGGCTGACAAGATCCAGGGCCGTACAATACCAATTGATGGAAAT |
| | TTTTTTACATATACAAGACATGAACCTATTGGTGTATGTGGCCAAAT |
| | CATTCCTTGGAATTTCCCGTTGGTTATGCTCATTTGGAAGATAGGGC |
| | CTGCACTGAGCTGTGGAAACACAGTGGTTGTCAAACCAGCAGAGCAA |
| | ACTCCTCTCACTGCTCTCCACGTGGCATCTTTAATAAAGAGGCAGG |
| | GTTTCCTCCTGGAGTAGTGAATATTGTTCCTGGTTATGGGCCTACAG |

| SEQ ID NO: Name | Sequence |
|---|---|
| | CAGGGGCAGCCATTTCTTCTCACATGGATATAGACAAAGTAGCCTTC |
| | ACAGGATCAACAGAGGTTGGCAAGTTGATCAAAGAAGCTGCCGGGAA |
| | AAGCAATCTGAAGAGGGTGACCCTGGAGCTTGGAGGAAAGAGCCCTT |
| | GCATTGTGTTAGCTGATGCCGACTTGGACAATGCTGTTGAATTTGCA |
| | CACCATGGGGTATTCTACCACCAGGGCCAGTGTTGTATAGCCGCATC |
| | CAGGATTTTTGTGGAAGAATCAATTTATGATGAGTTTGTTCGAAGGA |
| | GTGTTGAGCGGGCTAAGAAGTATATCCTTGGAAATCCTCTGACCCCA |
| | GGAGTCACTCAAGGCCCTCAGATTGACAAGGAACAATATGATAAAAT |
| | ACTTGACCTCATTGAGAGTGGGAAGAAGAAGGGGCCAAACTGGAAT |
| | GTGGAGGAGGCCCGTGGGGGAATAAAGGCTACTTTGTCCAGCCCACA |
| | GTGTTCTCTAATGTTACAGATGAGATGCGCATTGCCAAAGAGGAGAT |
| | TTTTGGACCAGTGCAGCAAATCATGAAGTTTAAATCTTTAGATGACG |
| | TGATCAAAAGAGCAAACAATACTTTCTATGGCTTATCAGCAGGAGTG |
| | TTTACCAAAGACATTGATAAAGCCATAACAATCTCCTCTGCTCTGCA |
| | GGCAGGAACAGTGTGGGTGAATTGCTATGGCGTGGTAAGTGCCCAGT |
| | GCCCCTTTGGTGGATTCAAGATGTCTGGAAATGGAAGAGAACTGGGA |
| | GAGTACGGTTTCCATGAATATACAGAGGTCAAAACAGTCACAGTGAA |
| | AATCTCTCAGAAGAACTCAGGAAGCGGAGAGGGCAGGGGAAGTCTTC |
| | TAACATGCGGGGACGTGGAGGAAAATCCCGGCCCCATGGGCGCCGGC |
| | GCCACCGGCAGAGCCATGGACGGCCCCAGACTGCTGCTGCTGCTGCT |
| | GCTGGGCGTGAGCCTGGGCGGCGCCAGAAGCTGGATGGAGTGGGACA |
| | GAGAGATCAACAACTACACCAGCCTGATCCACAGCCTGATCGAGGAG |
| | AGCCAGAACCAGCAGGAGAAGAACGAGCAGGAGCTGCTGGAGCTGGA |
| | CAAGTGGGCCAGCCTGTGGAACTGGTTCAGAAGCGAGAGAAAGTGCT |
| | GCGTGGAGTGCCCCCCCTGCCCCGCCCCCCCGTGGCCGGCCCCCTG |
| | ATCGCCCTGGTGACCAGCGGCGCCCTGCTGGCCGTGCTGGGCATCAC |
| | CGGCTACTTCCTGATGAACAGAAGAAGCTGGAGCCCCACCGGCGAGA |
| | GACTGGAGCTGGAGCCCTAAACCCAGCTTTCTTGTACAAAGTGGTGA |
| | TAATCGAATTCCGATAATCAACCTCTGGATTACAAAATTTGTGAAAG |
| | ATTGACTGGTATTCTTAACTATGTTGCTCCTTTTACGCTATGTGGAT |
| | ACGCTGCTTTAATGCCTTTGTATCATGCTATTGCTTCCCGTATGGCT |
| | TTCATTTTCTCCTCCTTGTATAAATCCTGGTTGCTGTCTCTTTATGA |
| | GGAGTTGTGGCCCGTTGTCAGGCAACGTGGCGTGGTGTGCACTGTGT |
| | TTGCTGACGCAACCCCCACTGGTTGGGGCATTGCCACCACCTGTCAG |
| | CTCCTTTCCGGGACTTTCGCTTTCCCCCTCCCTATTGCCACGGCGGA |
| | ACTCATCGCCGCCTGCCTTGCCCGCTGCTGGACAGGGGCTCGGCTGT |
| | TGGGCACTGACAATTCCGTGGTGTTGTCGGGGAAGCTGACGTCCTTT |
| | CCATGGCTGCTCGCCTGTGTTGCCACCTGGATTCTGCGCGGGACGTC |
| | CTTCTGCTACGTCCCTTCGGCCCTCAATCCAGCGGACCTTCCTTCCC |
| | GCGGCCTGCTGCCGGCTCTGCGGCCTCTTCCGCGTCTTCGCCTTCGC |
| | CCTCAGACGAGTCGGATCTCCCTTTGGGCCGCCTCCCCGCATCGGGA |
| | ATTCCCGCGGTTCGCTTTAAGACCAATGACTTACAAGGCAGCTGTAG |
| | ATCTTAGCCACTTTTTAAAAGAAAAGGGGGGACTGGAAGGGCTAATT |
| | CACTCCCAACGAAGACAAGATCTGCTTTTTGCTTGTACTGGGTCTCT |
| | CTGGTTAGACCAGATCTGAGCCTGGGAGCTCTCTGGCTAACTAGGGA |
| | ACCCACTGCTTAAGCCTCAATAAAGCTTGCCTTGAGTGCTTCAAGTA |
| | GTGTGTGCCCGTCTGTTGTGTGACTCTGGTAACTAGAGATCCCTCAG |
| | ACCCTTTTAGTCAGTGTGGAAAATCTCTAGCAGTAGTAGTTCATGTC |
| | ATCTTATTATTCAGTATTTATAACTTGCAAAGAAATGAATATCAGAG |
| | AGTGAGAGGAACTTGTTTATTGCAGCTTATAATGGTTACAAATAAAG |
| | CAATAGCATCACAAATTTCACAAATAAAGCATTTTTTTCACTGCATT |
| | CTAGTTGTGGTTTGTCCAAACTCATCAATGTATCTTATCATGTCTGG |
| | CTCTAGCTATCCCGCCCCTAACTCCGCCCATCCCGCCCCTAACTCCG |
| | CCCAGTTCCGCCCATTCTCCGCCCCATGGCTGACTAATTTTTTTTAT |
| | TTATGCAGAGGCCGAGGCCGCCTCGGCCTCTGAGCTATTCCAGAAGT |
| | AGTGAGGAGGCTTTTTTGGAGGCCTAGGGACGTACCCAATTCGCCCT |
| | ATAGTGAGTCGTATTACGCGCGCTCACTGGCCGTCGTTTTACAACGT |
| | CGTGACTGGGAAAACCCTGGCGTTACCCAACTTAATCGCCTTGCAGC |
| | ACATCCCCCTTTCGCCAGCTGGCGTAATAGCGAAGAGGCCCGCACCG |
| | ATCGCCCTTCCCAACAGTTGCGCAGCCTGAATGGCGAATGGGACGCG |
| | CCCTGTAGCGGCGCATTAAGCGCGGCGGGTGTGGTGGTTACGCGCAG |
| | CGTGACCGCTACACTTGCCAGCGCCCTAGCGCCCGCTCCTTTCGCTT |
| | TCTTCCCTTCCTTTCTCGCCACGTTCGCCGGCTTTCCCCGTCAAGCT |
| | CTAAATCGGGGGCTCCCTTTAGGGTTCCGATTTAGTGCTTTACGGCA |
| | CCTCGACCCCAAAAAACTTGATTAGGGTGATGGTTCACGTAGTGGGC |
| | CATCGCCCTGATAGACGGTTTTTCGCCCTTTGACGTTGGAGTCCACG |
| | TTCTTTAATAGTGGACTCTTGTTCCAAACTGGAACAACACTCAACCC |
| | TATCTCGGTCTATTCTTTTGATTTATAAGGGATTTTGCCGATTTCGG |
| | CCTATTGGTTAAAAAATGAGCTGATTTAACAAAAATTTAACGCGAAT |
| | TTTAACAAAATATTAACGCTTACAATTTAGGTGGCACTTTTCGGGGA |
| | AATGTGCGCGGAACCCCTATTTGTTTATTTTTCTAAATACATTCAAA |
| | TATGTATCCGCTCATGAGACAATAACCCTGATAAATGCTTCAATAAT |
| | ATTGAAAAGGAAGAGTATGAGTATTCAACATTTCCGTGTCGCCCTT |
| | ATTCCCTTTTTTGCGGCATTTTGCCTTCCTGTTTTTGCTCACCCAGA |
| | AACGCTGGTGAAAGTAAAAGATGCTGAAGATCAGTTGGGTGCACGAG |
| | TGGGTTACATCGAACTGGATCTCAACAGCGGTAAGATCCTTGAGAGT |
| | TTTCGCCCCGAAGAACGTTTTCCAATGATGAGCACTTTTAAAGTTCT |

| SEQ ID NO: | Name | Sequence |
|---|---|---|
| | | GCTATGTGGCGCGGTATTATCCCGTATTGACGCCGGGCAAGAGCAAC |
| | | TCGGTCGCCGCATACACTATTCTCAGAATGACTTGGTTGAGTACTCA |
| | | CCAGTCACAGAAAAGCATCTTACGGATGGCATGACAGTAAGAGAATT |
| | | ATGCAGTGCTGCCATAACCATGAGTGATAACACTGCGGCCAACTTAC |
| | | TTCTGACAACGATCGGAGGACCGAAGGAGCTAACCGCTTTTTTGCAC |
| | | AACATGGGGGATCATGTAACTCGCCTTGATCGTTGGGAACCGGAGCT |
| | | GAATGAAGCCATACCAAACGACGAGCGTGACACCACGATGCCTGTAG |
| | | CAATGGCAACAACGTTGCGCAAACTATTAACTGGCGAACTACTTACT |
| | | CTAGCTTCCCGGCAACAATTAATAGACTGGATGGAGGCGGATAAAGT |
| | | TGCAGGACCACTTCTGCGCTCGGCCCTTCCGGCTGGCTGGTTTATTG |
| | | CTGATAAATCTGGAGCCGGTGAGCGTGGGTCTCGCGGTATCATTGCA |
| | | GCACTGGGGCCAGATGGTAAGCCCTCCCGTATCGTAGTTATCTACAC |
| | | GACGGGGAGTCAGGCAACTATGGATGAACGAAATAGACAGATCGCTG |
| | | AGATAGGTGCCTCACTGATTAAGCATTGGTAACTGTCAGACCAAGTT |
| | | TACTCATATATACTTTAGATTGATTTAAAACTTCATTTTTAATTTAA |
| | | AAGGATCTAGGTGAAGATCCTTTTTGATAATCTCATGACCAAAATCC |
| | | CTTAACGTGAGTTTTCGTTCCACTGAGCGTCAGACCCCGTAGAAAAG |
| | | ATCAAAGGATCTTCTTGAGATCCTTTTTTTCTGCGCGTAATCTGCTG |
| | | CTTGCAAACAAAAAAACCACCGCTACCAGCGGTGGTTTGTTTGCCGG |
| | | ATCAAGAGCTACCAACTCTTTTTCCGAAGGTAACTGGCTTCAGCAGA |
| | | GCGCAGATACCAAATACTGTTCTTCTAGTGTAGCCGTAGTTAGGCCA |
| | | CCACTTCAAGAACTCTGTAGCACCGCCTACATACCTCGCTCTGCTAA |
| | | TCCTGTTACCAGTGGCTGCTGCCAGTGGCGATAAGTCGTGTCTTACC |
| | | GGGTTGGACTCAAGACGATAGTTACCGGATAAGGCGCAGCGGTCGGG |
| | | CTGAACGGGGGGTTCGTGCACACAGCCCAGCTTGGAGCGAACGACCT |
| | | ACACCGAACTGAGATACCTACAGCGTGAGCTATGAGAAAGCGCCACG |
| | | CTTCCCGAAGAGAGAAAGGCGGACAGGTATCCGGTAAGCGGCAGGGT |
| | | CGGAACAGGAGAGCGCACGAGGGAGCTTCCAGGGGGAAACGCCTGGT |
| | | ATCTTTATAGTCCTGTCGGGTTTCGCCACCTCTGACTTGAGCGTCGA |
| | | TTTTTGTGATGCTCGTCAGGGGGGCGGAGCCTATGGAAAAACGCCAG |
| | | CAACGCGGCCTTTTTACGGTTCCTGGCCTTTTGCTGGCCTTTTGCTC |
| | | ACATGTTCTTTCCTGCGTTATCCCCTGATTCTGTGGATAACCGTATT |
| | | ACCGCCTTTGAGTGAGCTGATACCGCTCGCCGCAGCCGAACGACCGA |
| | | GCGCAGCGAGTCAGTGAGCGAGGAAGCGGAAGAGCGCCCAATACGCA |
| | | AACCGCCTCTCCCCGCGCGTTGGCCGATTCATTAATGCAGCTGGCAC |
| | | GACAGGTTTCCCGACTGGAAAGCGGGCAGTGAGCGCAACGCAATTAA |
| | | TGTGAGTTAGCTCACTCATTAGGCACCCCAGGCTTTACACTTTATGC |
| | | TTCCGGCTCGTATGTTGTGTGGAATTGTGAGCGGATAACAATTTCAC |
| | | ACAGGAAACAGCTATGACCATGATTACGCCAAGCGCGCAATTAACCC |
| | | TCACTAAAGGGAACAAAAGCTGGAGCTGCAAGCTT |
| 5 | pLV: maC46: shCCR5 | AATGTAGTCTTATGCAATACTCTTGTAGTCTTGCAACATGGTAACGA |
| | | TGAGTTAGCAACATGCCTTACAAGGAGAGAAAAAGCACCGTGCATGC |
| | | CGATTGGTGGAAGTAAGGTGGTACGATCGTGCCTTATTAGGAAGGCA |
| | | ACAGACGGGTCTGACATGGATTGGACGAACCACTGAATTGCCGCATT |
| | | GCAGAGATATTGTATTTAAGTGCCTAGCTCGATACATAAACGGGTCT |
| | | CTCTGGTTAGACCAGATCTGAGCCTGGGAGCTCTCTGGCTAACTAGG |
| | | GAACCCACTGCTTAAGCCTCAATAAAGCTTGCCTTGAGTGCTTCAAG |
| | | TAGTGTGTGCCCGTCTGTTGTGTGACTCTGGTAACTAGAGATCCCTC |
| | | AGACCCTTTTAGTCAGTGTGGAAAATCTCTAGCAGTGGCGCCCGAAC |
| | | AGGGACTTGAAAGCGAAAGGGAAACCAGAGGAGCTCTCTCGACGCAG |
| | | GACTCGGCTTGCTGAAGCGCGCACGGCAAGAGGCGAGGGGCGGCGAC |
| | | TGGTGAGTACGCCAAAAATTTTGACTAGCGGAGGCTAGAAGGAGAGA |
| | | GATGGGTGCGAGAGCGTCAGTATTAAGCGGGGAGAATTAGATCGCG |
| | | ATGGGAAAAAATTCGGTTAAGGCCAGGGGGAAAGAAAAAATATAAAT |
| | | TAAAACATATAGTATGGGCAAGCAGGGAGCTAGAACGATTCGCAGTT |
| | | AATCCTGGCCTGTTAGAAACATCAGAAGGCTGTAGACAAATACTGGG |
| | | ACAGCTACAACCATCCCTTCAGACAGGATCAGAAGAACTTAGATCAT |
| | | TATATAATACAGTAGCAACCCTCTATTGTGTGCATCAAAGGATAGAG |
| | | ATAAAAGACACCAAGGAAGCTTTAGACAAGATAGAGGAAGAGCAAAA |
| | | CAAAAGTAAGACCACCGCACAGCAAGCGGCCGCTGATCTTCAGACCT |
| | | GGAGGAGGAGATATGAGGGACAATTGGAGAAGTGAATTATATAAATA |
| | | TAAAGTAGTAAAAATTGAACCATTAGGAGTAGCACCCACCAAGGCAA |
| | | AGAGAAGAGTGGTGCAGAGAGAAAAAAGAGCAGTGGGAATAGGAGCT |
| | | TTGTTCCTTGGGTTCTTGGGAGCAGCAGGAAGCACTATGGGCGCAGC |
| | | GTCAATGACGCTGACGGTACAGGCCAGACAATTATTGTCTGGTATAG |
| | | TGCAGCAGCAGAACAATTTGCTGAGGGCTATTGAGGCGCAACAGCAT |
| | | CTGTTGCAACTCACAGTCTGGGGCATCAAGCAGCTCCAGGCAAGAAT |
| | | CCTGGCTGTGGAAAGATACCTAAAGGATCAACAGCTCCTGGGGATTT |
| | | GGGGTTGCTCTGGAAAACTCATTTGCACCACTGCTGTGCCTTGGAAT |
| | | GCTAGTTGGAGTAATAAATCTCTGGAACAGATTTGGAATCACACGAC |
| | | CTGGATGGAGTGGGACAGAGAAATTAACAATTACACAAGCTTAATAC |
| | | ACTCCTTAATTGAAGAATCGCAAAACCAGCAAGAAAAGAATGAACAA |
| | | GAATTATTGGAATTAGATAAATGGGCAAGTTTGTGGAATTGGTTTAA |
| | | CATAACAAATTGGCTGTGGTATATAAAATTATTCATAATGATAGTAG |
| | | GAGGCTTGGTAGGTTTAAGAATAGTTTTTGCTGTACTTTCTATAGTG |
| | | AATAGAGTTAGGCAGGGATATTCACCATTATCGTTTCAGACCCACCT |

| SEQ ID NO: Name | Sequence |
|---|---|
| | CCCAACCCCGAGGGGACCCGACAGGCCCGAAGGAATAGAAGAAGAAG |
| | GTGGAGAGAGAGACAGAGACAGATCCATTCGATTAGTGAACGGATCT |
| | CGACGGTATCGCTAGCTTTTAAAAGAAAAGGGGGGATTGGGGGGTAC |
| | AGTGCAGGGGAAAGAATAGTAGACATAATAGCAACAGACATACAAAC |
| | TAAAGAATTACAAAAACAAATTACAAAAATTCAAAATTTTACTAGTG |
| | ATTATCGGATCAACTTTGTATAGAAAAGTTGGAATTCGAACGCTGAC |
| | GTCATCAACCCGCTCCAAGGAATCGCGGGCCCAGTGTCACTAGGCGG |
| | GAACACCCAGCGCGCGTGCGCCCTGGCAGGAAGATGGCTGTGAGGGA |
| | CAGGGGAGTGGCGCCCTGCAATATTTGCATGTCGCTATGTGTTCTGG |
| | GAAATCACCATAAACGTGAAATGTCTTTGGATTTGGGAATCTTATAA |
| | GTTCTGTATGAGACCACCGGGTCCATACAGTCAGTATCAATTCTCGA |
| | GAATTGATACTGACTGTATGGATTTTTGGATCCCAAGTTTGTACAAA |
| | AAAGCAGGCTGGCTCCGGTGCCCGTCAGTGGGCAGAGCGCACATCGC |
| | CCACAGTCCCCGAGAAGTTGGGGGGAGGGGTCGGCAATTGAACCGGT |
| | GCCTAGAGAAGGTGGCGCGGGGTAAACTGGGAAAGTGATGTCGTGTA |
| | CTGGCTCCGCCTTTTTCCCGAGGGTGGGGGAGAACCGTATATAAGTG |
| | CAGTAGTCGCCGTGAACGTTCTTTTTCGCAACGGGTTTGCCGCCAGA |
| | ACACAGGTAAGTGCCGTGTGTGGTTCCCGCGGGCCTGGCCTCTTTAC |
| | GGGTTATGGCCCTTGCGTGCCTTGAATTACTTCCACCTGGCTGCAGT |
| | ACGTGATTCTTGATCCCGAGCTTCGGGTTGGAAGTGGGTGGGAGAGT |
| | TCGAGGCCTTGCGCTTAAGGAGCCCCTTCGCCTCGTGCTTGAGTTGA |
| | GGCCTGGCCTGGGCGCTGGGGCCGCCGCGTGCGAATCTGGTGGCACC |
| | TTCGCGCCTGTCTCGCTGCTTTCGATAAGTCTCTAGCCATTTAAAAT |
| | TTTTGATGACCTGCTGCGACGCTTTTTTTCTGGCAAGATAGTCTTGT |
| | AAATGCGGGCCAAGATCTGCACACTGGTATTTCGGTTTTTGGGGCCG |
| | CGGGCGGCGACGGGGCCCGTGCGTCCCAGCGCACATGTTCGGCGAGG |
| | CGGGGCCTGCGAGCGCGGCCACCGAGAATCGGACGGGGGTAGTCTCA |
| | AGCTGGCCGGCCTGCTCTGGTGCCTGGTCTCGCGCCGCCGTGTATCG |
| | CCCCGCCCTGGGCGGCAAGGCTGGCCCGGTCGGCACCAGTTGCGTGA |
| | GCGGAAAGATGGCCGCTTCCCGGCCCTGCTGCAGGGAGCTCAAAATG |
| | GAGGACGCGGCGCTCGGGAGAGCGGGCGGGTGAGTCACCCACACAAA |
| | GGAAAAGGGCCTTTCCGTCCTCAGCCGTCGCTTCATGTGACTCCACG |
| | GAGTACCGGGCGCCGTCCAGGCACCTCGATTAGTTCTCGAGCTTTTG |
| | GAGTACGTCGTCTTTAGGTTGGGGGGAGGGGTTTTATGCGATGGAGT |
| | TTCCCCACACTGAGTGGGTGGAGACTGAAGTTAGGCCAGCTTGGCAC |
| | TTGATGTAATTCTCCTTGGAATTTGCCCTTTTTGAGTTTGGATCTTG |
| | GTTCATTCTCAAGCCTCAGACAGTGGTTCAAAGTTTTTTTCTTCCAT |
| | TTCAGGTGTCGTGAGCCACCATGGGCGCCGGCGCCACCGGCAGAGCC |
| | ATGGACGGCCCCAGACTGCTGCTGCTGCTGCTGGGCGTGAGCCT |
| | GGGCGGCGCCAGAAGCTGGATGGAGTGGGACAGAGAGATCAACAACT |
| | ACACCAGCCTGATCCACAGCCTGATCGAGGAGAGCCAGAACCAGCAG |
| | GAGAAGAACGAGCAGGAGCTGCTGGAGCTGGACAAGTGGGCCAGCCT |
| | GTGGAACTGGTTCAGAAGCGAGAGAAAGTGCTGCGTGGAGTGCCCCC |
| | CCTGCCCCGCCCCCCCGTGGCCGGCCCCCTGATCGCCCTGGTGACC |
| | AGCGGCGCCCTGCTGGCCGTGCTGGGCATCACCGGCTACTTCCTGAT |
| | GAACAGAAGAAGCTGGAGCCCCACCGGCGAGAGACTGGAGCTGGAGC |
| | CCTAAAAACCCAGCTTTCTTGTACAAAGTGGTGATAATCGAATTCCG |
| | ATAATCAACCTCTGGATTACAAAATTTGTGAAAGATTGACTGGTATT |
| | CTTAACTATGTTGCTCCTTTTACGCTATGTGGATACGCTGCTTTAAT |
| | GCCTTTGTATCATGCTATTGCTTCCCGTATGGCTTTCATTTTCTCCT |
| | CCTTGTATAAATCCTGGTTGCTGTCTCTTTATGAGGAGTTGTGGCCC |
| | GTTGTCAGGCAACGTGGCGTGGTGTGCACTGTGTTTGCTGACGCAAC |
| | CCCCACTGGTTGGGGCATTGCCACCACCTGTCAGCTCCTTTCCGGGA |
| | CTTTCGCTTTCCCCCTCCCTATTGCCACGGCGGAACTCATCGCCGCC |
| | TGCCTTGCCCGCTGCTGGACAGGGGCTCGGCTGTTGGGCACTGACAA |
| | TTCCGTGGTGTTGTCGGGGAAGCTGACGTCCTTTCCATGGCTGCTCG |
| | CCTGTGTTGCCACCTGGATTCTGCGCGGGACGTCCTTCTGCTACGTC |
| | CCTTCGCCCTCAATCCAGCGGACCTTCCTTCCCGCGGCCTGCTGCC |
| | GGCTCTGCGGCCTCTTCCGCGTCTTCGCCTTCGCCCTCAGACGAGTC |
| | GGATCTCCCTTTGGGCCGCCTCCCCGCATCGGGAATTCCCGCGGTTC |
| | GCTTTAAGACCAATGACTTACAAGGCAGCTGTAGATCTTAGCCACTT |
| | TTTAAAAGAAAAGGGGGACTGGAAGGGCTAATTCACTCCCAACGAA |
| | GACAAGATCTGCTTTTTGCTTGTACTGGGTCTCTCTGGTTAGACCAG |
| | ATCTGAGCCTGGGAGCTCTCTGGCTAACTAGGGAACCCACTGCTTAA |
| | GCCTCAATAAAGCTTGCCTTGAGTGCTTCAAGTAGTGTGTGCCCGTC |
| | TGTTGTGTGACTCTGGTAACTAGAGATCCCTCAGACCCTTTTAGTCA |
| | GTGTGGAAAATCTCTAGCAGTAGTAGTTCATGTCATCTTATTATTCA |
| | GTATTTATAACTTGCAAAGAAATGAATATCAGAGAGTGAGAGGAACT |
| | TGTTTATTGCAGCTTATAATGGTTACAAATAAAGCAATAGCATCACA |
| | AATTTCACAAATAAAGCATTTTTTTCACTGCATTCTAGTTGTGGTTT |
| | GTCCAAACTCATCAATGTATCTTATCATGTCTGGCTCTAGCTATCCC |
| | GCCCCTAACTCCGCCCATCCCGCCCCTAACTCCGCCCAGTTCCGCCC |
| | ATTCTCCGCCCCATGGCTGACTAATTTTTTTTATTTATGCAGAGGCC |
| | GAGGCCGCCTCGGCCTCTGAGCTATTCCAGAAGTAGTGAGGAGGCTT |
| | TTTTGGAGGCCTAGGGACGTACCCAATTCGCCCTATAGTGAGTCGTA |
| | TTACGCGCGCTCACTGGCCGTCGTTTTACAACGTCGTGACTGGGAAA |
| | ACCCTGGCGTTACCCAACTTAATCGCCTTGCAGCACATCCCCCTTTC |

| SEQ ID NO: | Name | Sequence |
|---|---|---|
| | | GCCAGCTGGCGTAATAGCGAAGAGGCCCGCACCGATCGCCCTTCCCA |
| | | ACAGTTGCGCAGCCTGAATGGCGAATGGGACGCGCCCTGTAGCGGCG |
| | | CATTAAGCGCGGCGGGTGTGGTGGTTACGCGCAGCGTGACCGCTACA |
| | | CTTGCCAGCGCCCTAGCGCCCGCTCCTTTCGCTTTCTTCCCTTCCTT |
| | | TCTCGCCACGTTCGCCGGCTTTCCCCGTCAAGCTCTAAATCGGGGGC |
| | | TCCCTTTAGGGTTCCGATTTAGTGCTTTACGGCACCTCGACCCCAAA |
| | | AAACTTGATTAGGGTGATGGTTCACGTAGTGGGCCATCGCCCTGATA |
| | | GACGGTTTTTCGCCCTTTGACGTTGGAGTCCACGTTCTTTAATAGTG |
| | | GACTCTTGTTCCAAACTGGAACAACACTCAACCCTATCTCGGTCTAT |
| | | TCTTTTGATTTATAAGGGATTTTGCCGATTTCGGCCTATTGGTTAAA |
| | | AAATGAGCTGATTTAACAAAAATTTAACGCGAATTTTAACAAAATAT |
| | | TAACGCTTACAATTTAGGTGGCACTTTTCGGGGAAATGTGCGCGGAA |
| | | CCCCTATTTGTTTATTTTTCTAAATACATTCAAATATGTATCCGCTC |
| | | ATGAGACAATAACCCTGATAAATGCTTCAATAATATTGAAAAAGGAA |
| | | GAGTATGAGTATTCAACATTTCCGTGTCGCCCTTATTCCCTTTTTTG |
| | | CGGCATTTTGCCTTCCTGTTTTTGCTCACCCAGAAACGCTGGTGAAA |
| | | GTAAAAGATGCTGAAGATCAGTTGGGTGCACGAGTGGGTTACATCGA |
| | | ACTGGATCTCAACAGCGGTAAGATCCTTGAGAGTTTTCGCCCCGAAG |
| | | AACGTTTTCCAATGATGAGCACTTTTAAAGTTCTGCTATGTGGCGCG |
| | | GTATTATCCCGTATTGACGCCGGGCAAGAGCAACTCGGTCGCCGCAT |
| | | ACACTATTCTCAGAATGACTTGGTTGAGTACTCACCAGTCACAGAAA |
| | | AGCATCTTACGGATGGCATGACAGTAAGAGAATTATGCAGTGCTGCC |
| | | ATAACCATGAGTGATAACACTGCGGCCAACTTACTTCTGACAACGAT |
| | | CGGAGGACCGAAGGAGCTAACCGCTTTTTTGCACAACATGGGGGATC |
| | | ATGTAACTCGCCTTGATCGTTGGGAACCGGAGCTGAATGAAGCCATA |
| | | CCAAACGACGAGCGTGACACCACGATGCCTGTAGCAATGGCAACAAC |
| | | GTTGCGCAAACTATTAACTGGCGAACTACTTACTCTAGCTTCCCGGC |
| | | AACAATTAATAGACTGGATGGAGGCGGATAAAGTTGCAGGACCACTT |
| | | CTGCGCTCGGCCCTTCCGGCTGGCTGGTTTATTGCTGATAAATCTGG |
| | | AGCCGGTGAGCGTGGGTCTCGCGGTATCATTGCAGCACTGGGGCCAG |
| | | ATGGTAAGCCCTCCCGTATCGTAGTTATCTACACGACGGGGAGTCAG |
| | | GCAACTATGGATGAACGAAATAGACAGATCGCTGAGATAGGTGCCTC |
| | | ACTGATTAAGCATTGGTAACTGTCAGACCAAGTTTACTCATATATAC |
| | | TTTAGATTGATTTAAAACTTCATTTTTAATTTAAAAGGATCTAGGTG |
| | | AAGATCCTTTTTGATAATCTCATGACCAAAATCCCTTAACGTGAGTT |
| | | TTCGTTCCACTGAGCGTCAGACCCCGTAGAAAAGATCAAAGGATCTT |
| | | CTTGAGATCCTTTTTTTCTGCGCGTAATCTGCTGCTTGCAAACAAAA |
| | | AAACCACCGCTACCAGCGGTGGTTTGTTTGCCGGATCAAGAGCTACC |
| | | AACTCTTTTTCCGAAGGTAACTGGCTTCAGCAGAGCGCAGATACCAA |
| | | ATACTGTTCTTCTAGTGTAGCCGTAGTTAGGCCACCACTTCAAGAAC |
| | | TCTGTAGCACCGCCTACATACCTCGCTCTGCTAATCCTGTTACCAGT |
| | | GGCTGCTGCCAGTGGCGATAAGTCGTGTCTTACCGGGTTGGACTCAA |
| | | GACGATAGTTACCGGATAAGGCGCAGCGGTCGGGCTGAACGGGGGGT |
| | | TCGTGCACACAGCCCAGCTTGGAGCGAACGACCTACACCGAACTGAG |
| | | ATACCTACAGCGTGAGCTATGAGAAAGCGCCACGCTTCCCGAAGAGA |
| | | GAAAGGCGGACAGGTATCCGGTAAGCGGCAGGGTCGGAACAGGAGAG |
| | | CGCACGAGGGAGCTTCCAGGGGGAAACGCCTGGTATCTTTATAGTCC |
| | | TGTCGGGTTTCGCCACCTCTGACTTGAGCGTCGATTTTTGTGATGCT |
| | | CGTCAGGGGGGCGGAGCCTATGGAAAAACGCCAGCAACGCGGCCTTT |
| | | TTACGGTTCCTGGCCTTTTGCTGGCCTTTTGCTCACATGTTCTTTCC |
| | | TGCGTTATCCCCTGATTCTGTGGATAACCGTATTACCGCCTTTGAGT |
| | | GAGCTGATACCGCTCGCCGCAGCCGAACGACCGAGCGCAGCGAGTCA |
| | | GTGAGCGAGGAAGCGGAAGAGCGCCCAATACGCAAACCGCCTCTCCC |
| | | CGCGCGTTGGCCGATTCATTAATGCAGCTGGCACGACAGGTTTCCCG |
| | | ACTGGAAAGCGGGCAGTGAGCGCAACGCAATTAATGTGAGTTAGCTC |
| | | ACTCATTAGGCACCCCAGGCTTTACACTTTATGCTTCCGGCTCGTAT |
| | | GTTGTGTGGAATTGTGAGCGGATAACAATTTCACACAGGAAACAGCT |
| | | ATGACCATGATTACGCCAAGCGCGCAATTAACCCTCACTAAAGGGAA |
| | | CAAAAGCTGGAGCTGCAAGCTT |
| 6 | hCCR5 shRNA sense | ACTCTTGACAGGGCTCTATTT |
| 7 | hCCR5 shRNA antisense | AAATAGAGCCCTGTCAAGAGT |
| 8 | Human CD4 Promoter: -1076 to +20 | AAGACAGGTTCTCACTCTGTCACTCAGGCTAGAGTGCAGTGGTGCAA |
| | | TCACGGTTCACTGCAGCCTCAACTTCCTGGGCTCAAGCGATCCCCCC |
| | | ACCTCGGCCTCCTAAAATGCTGGGATTATAGGCATGAGCCACCACTC |
| | | CCAGCCCCACTTTTTTCAGACTGGAAAACGCACACTCACATGTGCAT |
| | | CTTTAAATGATCACTTGGGCTGTGGTATGGAGAATGGCGACCAGTGA |
| | | GGAGGCAGGAGCTGTTGTCCGAGCAAGGGATGATATTGGCATCTTGG |
| | | ATTGGCATGGTGGCAGTAGTGGTAGTGCAGAGTGACTTGGGTAGATT |
| | | TTGGAGCCATTTAGAAGGTAACATCCACAGGAACTGGTAAATAAATA |
| | | CGTGGGAGAAGTTGGGTGAAGGGGGTGTCAAAGATTACACCCAATTT |

-continued

| SEQ ID NO: | Name | Sequence |
|---|---|---|
|  |  | ATTTTGCTTGGGCAAGTTGGTGGATGGTGAGCCCCTCACTGAGTGAG<br>AAGCCTGGAGAAGCAGGTTTGGAGGGTGGTAGTATGCAGGTGGTATG<br>CATAGTTGGGGATGTGTGTTGAGTTTGCTATGTCCGGTGAGCTTCCC<br>AGTGGGAGATGTCCAATGGGCAGACGGATACTCACATAGAGAGTTCAT<br>GGTAGATTCGGGCTAGAGGAAAGCACCTGAGGCCTGGCCAGAGACGC<br>CTAGAGGAACAGAGCCTGGTTAACAGTCACTCCTGGTGTCTCAGATA<br>TTCTCTGCTCAGCCCACGCCCTCTCTTCCACACTGGGCCACCTATAA<br>AGCCTCCACAGATACCCCTGGGGCACCCACTGGACACATGCCCTCAG<br>GGCCCCAGAGCAAGGAGCTGTTTGTGGGCTTACCACTGCTGTTCCCA<br>TATGCCCCAACTGCCTCCCACTTCTTTCCCCACAGCCTGGTCAGAC<br>ATGGCGCTACCACTAATGGAATCTTTCTTGCCATCTTTTTCTTGCCG<br>CTTAACAGTGGCAGTGACAGTTTGACTCCTGATTTAAGCCTGATTCT<br>GCTTAACTTTTTCCCTTGACTTTGGCATTTTCACTTTGACATGTTCC<br>CTGAGAGCCTGGGGGGTGGGAACCCAGCTCCAGCTGGTGACGTTTG<br>GGGCCGGCCCAGGCC |
| 9 | Human<br>CD3E | AAGGTACGGAAGAGGACGGTGGCGGTGGAAGCCGGGCTTGGAGATGG<br>GACACAGATTTCCACAAGCTGCCTGGAAAAGCTGCGAGCCAGGGCTG<br>GGGAAGTGAAGGAGGGAGGTGTCTCAAGCAGGCACACCCCCACCCTG<br>AGGCAGCCGCCTGCAGCCAGAGGCGGGCTGTGGTTAAGCAGCGCAGG<br>ATGTGGGCTGCACTGCTAAGCGTGGCTTCTGGGAGTGAGGGTGGGAG<br>AGGTACAGCGGCAGCTGGCGGAGGCCCGTGTGAGAGCGCTTTGTTCT<br>CAGTCTCCCACAGCACACTCTGCTTGCAGAGGGGGATC |
| 12 | CD34<br>Promoter<br>Sequence | AGGATGATGGTGATGGGGAACTAAATGGGGAAATATGGAAGGTCACA<br>GGAAAAGTTAACACAAGTTAGCAAAAAGTTAACATAACACAAAAAGG<br>TCTTGCAGGAAAAAAAAAGAAAAGAAAAGAAAGAAAAAGTCTCCAA<br>GAATGGTTTGGACAGCCAAAATGAATACTTATAGTCACGTATACCTG<br>CTCACTCCTGACGCTTCACTCACACAGCACAGGATCTGGTGAGGC<br>TATCACTAAATGTGCCACATTGTGGTTAAGTTTTACCTGATTAACGA<br>AATGCTCACACTTCTAAACTGAGGTCCTTACAGTAGATTCCTTTTGC<br>AAGATTGTTACTGGCTTACAACTTAAAAATAAAGGAAAATCACAAGG<br>AAAGAAAAGTGGGGAAAAAATCGGAGGAAACTTGCCCCTGCCCTGGC<br>CACCGGCAAGGCTGCCACAAAGGGGTTAAAAGTTAAGTGGAAGTGGA<br>GCTTGAAGAAGTGGGATGGGGCCTCTCCAGGAAAGCTGAACGAGGCA<br>TCTGGAGCCCGAACAAACCTCCA |
| 13 | miR30<br>cassette<br>carrying<br>CCR5<br>shRNA | TGTTTGAATGAGGCTTCAGTACTTTACAGAATCGTTGCCTGCACATC<br>TTGGAAACACTTGCTGGGATTACTTCGACTTCTTAACCCAACAGAAG<br>GCTCGAGAAGGTATATTGCTGTTGACAGTGAGCGCACTCTTGACAGG<br>GCTCTATTTTAGTGAAGCCACAGATGTAAAATAGAGCCCTGTCAAGA<br>GTTTGCCTACTGCCTCGGACTTCAAGGGGCTAGAATTCGAGCAATTA<br>TCTTGTTTACTAAAACTGAATACCTTGCTATCTCTTTGATACATTTT<br>TACAAAGCTGAATTAAAATGGTATAAATTAAATCACTTT |
| 14 | C44 gp41<br>Fusion<br>Inhibitor<br>Peptide<br>Sequence | GCCTGGAAGGACCTGGAGCTGCTGGAGCAGGAGAACAAGGAGCAGCA<br>GAACCAGAGCGAGGAGATCCTGAGCCACATCCTGAGCACCTACAACA<br>ACATCGAGAGAGACTGGGAGATGTGGACCATGAACAAC |
| 15 | C44 gp41<br>Fusion<br>Inhibitor<br>Peptide<br>Sequence | AWKDLELLEQENKEQQNQSEEILSHILSTYNNIERDWEMWTMNN |
| 16 | GPI anchor | GAGCTGAAGACCCCCCTGGGCGACACCACCCACACCTGCCCCAGATG<br>CCCCGAGCCCAAGAGCTGCGACACCCCCCCCCCTGCCCCAGATGCC<br>CCGAGCCCAAGAGCTGCGACACCCCCCCCCCTGCCCCAGATGCCCC<br>GAGCCCAAGAGCTGCGACACCCCCCCCCCTGCCCCAGATGCCCCCT<br>TGAAAATGGTGGGACATCCTTATCAGAGAAAACAGTTCTTCTGCTGG<br>TGACTCCATTTCTGGCAGCAGCCTGGAGCCTTCATCCC |
| 17 | GPI Anchor | ELKTPLGDTTHTCPRCPEPKSCDTPPPCPRCPEPKSCDTPPPCPRCP<br>EPKSCDTPPPCPRCPLENGGTSLSEKTVLLLVTPFLAAAWSLHP |
| 18 | C44: hIgG3/<br>GPI | GCCTGGAAGGACCTGGAGCTGCTGGAGCAGGAGAACAAGGAGCAGCA<br>GAACCAGAGCGAGGAGATCCTGAGCCACATCCTGAGCACCTACAACA<br>ACATCGAGAGAGACTGGGAGATGTGGACCATGAACAACGAGCTGAAG<br>ACCCCCCTGGGCGACACCACCCACACCTGCCCCAGATGCCCCGAGCC<br>CAAGAGCTGCGACACCCCCCCCCCTGCCCCAGATGCCCCGAGCCCA<br>AGAGCTGCGACACCCCCCCCCCTGCCCCAGATGCCCCGAGCCCAAG<br>AGCTGCGACACCCCCCCCCCTGCCCCAGATGCCCCCTTGAAAATGG<br>TGGGACATCCTTATCAGAGAAAACAGTTCTTCTGCTGGTGACTCCAT<br>TTCTGGCAGCAGCCTGGAGCCTTCATCCC |

-continued

| SEQ ID NO: | Name | Sequence |
|---|---|---|
| 19 | C44: hIgG3/ GPI | AWKDLELLEQENKEQQNQSEEILSHILSTYNNIERDWEMWTMNNELK TPLGDTTHTCPRCPEPKSCDTPPPCPRCPEPKSCDTPPPCPRCPEPK SCDTPPPCPRCPLENGGTSLSEKTVLLLVTPFLAAAWSLHP |

The compositions can be administered to a subject by any suitable mode and route. Non-limiting examples include internal, pulmonary, rectal, nasal, vaginal, lingual, intravenous, intraarterial, intramuscular, intraperitoneal, intracutaneous and subcutaneous routes. Compositions may also be suitable for transdermal delivery as part of a cream, gel, or patch. Other dosage forms include tablets, capsules, pills, powders, aerosols, suppositories, parenterals, and oral liquids, including suspensions, solutions and emulsions. Sustained release dosage forms may also be used. The non-myeloablative dose of the chemotherapeutic can be administered orally or as otherwise provided herein.

In some embodiments, embodiments provided herein also include, but are not limited to:

1. A method for performing a bone marrow transplant in a patient, the method comprising: administering to the patient a population of cyclophosphamide-resistant modified cells and at least one non-myeloablative dose of cyclophosphamide.
2. The method of embodiment 1, wherein the population of cyclophosphamide resistance modified cells comprises a heterologous gene encoding aldehyde dehydrogenase 1 (ALDH1).
3. The method of embodiment 1, wherein the population of cyclophosphamide resistance modified cells express ALDH1.
4. The method of embodiment 1, wherein the cyclophosphamide resistance of cyclophosphamide-resistant modified cells is conferred by expression of aldehyde dehydrogenase 1 (ALDH 1).
5. The method of any one of embodiments 1-4, wherein greater than 50% of the patient's bone marrow is replaced with the cyclophosphamide-resistant modified cells or cells derived therefrom within 6 months.
6. The method of any one of embodiments 1-5, wherein the patient has HIV.
7. The method of any one of embodiments 1-6, wherein cyclophosphamide resistance of the modified cells is transient.
8. The method according to any one of embodiments 1-7, wherein the cells are stem cells or immune cells.
9. The method of embodiment 8, wherein the stem cell are fetal stem cells, cord blood derived stem cells, hematopoietic stem cells (HSCs), pluripotent stem cells (PSCs), induced PSCs (iPSCs), embryonic stem cells (ESCs) or cells derived therefrom, such as CD34+ cells, CD90+ cells, CD45+ cells, CD17+ cells, CD45RA-cells, CD38-, or any combination thereof.
10. The method of embodiment 8, wherein the immune cells are T cells.
11. The method of any one of embodiments 1-10, wherein the modified cells are autologous to the patient, allogeneic to the patient, or a combination thereof.
12. The method of any one of embodiments 1-11, further comprising contacting unmodified cells with an expression vector encoding for the expression of ALDH1 to produce the cyclophosphamide-resistant modified cells.
13. The method of embodiment 12, wherein the expression vector is a viral vector or a non-viral vector.
14. The method of embodiment 13, wherein the viral vector is a lentiviral or adenoviral vector.
15. The method of embodiments 12, wherein the expression vector is a retrovirus, a transposon, an episomal expression vector, modified RNA, a plasmid, or any combination thereof.
16. The method of any one of embodiments 1-15, wherein the at least one non-myeloablative dose of the chemotherapeutic agent is administered after administration of the modified cells.
17. The method of any one of embodiments 1-16 embodiment 1, wherein the at least one non-myeloablative dose of the chemotherapeutic agent is a non-myeloablative dose of cyclophosphamide.
18. The method of embodiment 17, wherein the non-myeloablative dose of cyclophosphamide is from about 0.16 mg/kg/day to less than 2.5 mg/kg/day.
19. The method of embodiment 17, wherein the non-myeloablative dose of cyclophosphamide is from about 0.41 mg/kg/day to about 1.63 mg/kg/day.
20. The method of embodiment 17, wherein the non-myeloablative dose of cyclophosphamide is from about 0.81 mg/kg/day to about 1.46 mg/kg/day.
21. The method of embodiment 17, wherein the non-myeloablative dose of cyclophosphamide is about 1.3 mg/kg/day.
22. The method of any one of embodiments 17-21, wherein the patient is not administered a dose of 100 mg/m$^2$/day of cyclophosphamide for 1-14 consecutive days.
23. The method of any one of embodiments 17-22, wherein the patient is not administered a dose of 5-7 g/m$^2$ of cyclophosphamide over 12-24 hours.
24. The method according to any one of the preceding embodiments, wherein the non-myeloablative chemotherapeutic agent is administered every day for at least 1 week, at least 2 weeks, at least 3 weeks, at least 1 month, at least 2 months, at least 3 months, at least 4 months, at least 5 months, or at least 6 months.
25. The method according to any one of the preceding embodiments, further comprising not administering the non-myeloablative dose of the chemotherapeutic agent for a period of time between the administering of the cyclophosphamide-resistant modified cells and at least one non-myeloablative dose of the chemotherapeutic agent.
26. The method of embodiment 25, wherein the period of time is selected from the group consisting of about 3 days, about 7 days, about 10 days, and about 14 days.
27. The method of embodiment and one of the preceding embodiments, wherein greater than about 60%, about 70%, about 80%, about 90%, about 95%, or 100% of the patient's bone marrow is replaced with the modified cells.
28. The method according to any one of the preceding embodiments, wherein the patient is not myeloablated and/or immunocompromised as a result of the administration of the at least one non-myeloablative dose of the chemotherapeutic agent 29. The method according to any one of the preceding embodiments, wherein the patient does not experience clinically relevant anemia, neutropenia, thrombocytopenia, pancytopenia, low platelet, low white blood cells, or any combination thereof or related symptoms.

30. The method according to any one of the preceding embodiments, wherein a preconditioning step is performed prior to administration of the cells.

31. The method of embodiment 30, wherein the preconditioning step is a non-myeloablative chemotherapy preconditioning step.

32. The method of according to any one of the preceding embodiments, wherein the modified cells are resistant to HIV infection.

33. The method of embodiment 32, wherein the modified cells heterologously express a mutation of at least one HIV co-receptor resistant to HIV infection, a mutation or plurality of mutations of at least one HIV co-receptor, at least one HIV fusion inhibitor, a molecule that reduces the expression of a HIV co-receptor, or any combination thereof.

34. The method of embodiment 32, wherein the modified cells heterologously express shCCR5, shCXCR4, a C-peptide fusion inhibitor or any combination thereof.

35. The method of embodiment 32, wherein the modified cells do not express a HIV co-receptor.

36. The method of embodiment 32, wherein the modified cells do not express CCR5, CXCR4, or express CCR5-Δ32 or a combination thereof.

37. A cell comprising a heterologous nucleotide molecule that encodes for the expression of ALDH1 and one of: i) a heterologous nucleotide molecule encoding for at least one HIV co-receptor mutant, a mutation or plurality of mutations of at least one HIV co-receptor, at least one HIV fusion inhibitor, a molecule that reduces the expression of a HIV co-receptor, or any combination thereof; and/or ii) an endogenous HIV co-receptor mutation or deletion.

38. The cell of embodiment 37, wherein the cell comprises a heterologous nucleotide sequence that: i. encodes for a molecule reduces expression of the CCR5; encodes for a reduces expression of the CXCR4; iii. encodes for the expression of a C-peptide fusion inhibitor; iv. comprises a sequence of: 1, 3, 6, 7, 8, 9, 12, 13, 14, 16, 18, or any combination thereof v. encodes for a sequence of SEQ ID NO: 10, 11, 6, 7, 13, 15, 17, 19, or any combination thereof; or any combination thereof.

39. The cell of embodiments 37 and 38, wherein the cell expresses shCCR5, shCXCR4, and/or a C-peptide fusion inhibitor, such as C44.

40. The cell of embodiment 37, wherein the cell is modified to express the heterologous nucleotide sequences with a non-viral gene transfer system.

41. The cell of embodiment 40, wherein the non-viral gene transfer system is a transposon gene transfer system.

42. The cell of embodiment 37, wherein the transposon gene transfer system is a Sleeping Beauty gene transfer system or a PiggyBac transposon gene transfer system.

43. The cell of any one of embodiments 37-42, wherein the cell includes an heterologous nucleic acid sequence of SEQ ID NO: 4.

44. A composition comprising one or more cells of any one of embodiments 37 to 43.

45. A nucleic acid molecule encoding for ALDH1 and one of: i) a heterologous nucleotide molecule encoding for at least one HIV co-receptor mutant, a mutation or plurality of mutations of at least one HIV co-receptor, at least one HIV fusion inhibitor, a molecule that reduces the expression of a HIV co-receptor, or any combination thereof.

46. The nucleic acid molecule of embodiment 45, wherein the heterologous nucleotide sequence encodes a molecule that: i. reduces expression of the CCR5;
ii. reduces expression of the CXCR4; encodes for the expression of a C-peptide fusion inhibitor; or any combination thereof.

47. The nucleic acid molecule of embodiments 45 and 46, wherein the nucleic acid molecule encodes for the expression shCCR5, shCXCR4, and/or a C-peptide fusion inhibitor.

48. The nucleic acid molecule of embodiment 45, wherein the molecule comprises a sequence of: 1, 3, 6, 7, 8, 9, 12, 13, 14, 16, 18, or any combination thereof.

49. The nucleic acid molecule of embodiment 45, wherein the molecule comprises a nucleic acid molecule that encodes for a sequence of SEQ ID NO: 10, 11, 6, 7, 13, 15, 17, 19, or any combination thereof.

50. A vector comprising the nucleic acid molecules of any one of embodiments 45-49.

51. The vector of embodiment 50, wherein the vector is a vector that can be used to produce a lentivirus.

52. The vector of embodiment 50, wherein the vector is a lentiviral vector.

53. The vector of embodiment 50, wherein the vector comprises a sequence of SEQ ID NO: 1, 3, 6, 7, 8, 9, 12, 13, 14, 16, 18, or any combination thereof.

54. The vector of embodiment 50, wherein the vector comprises a nucleic acid molecule that encodes for a sequence of SEQ ID NO: 10, 11, 6, 7, 13, 15, 17, 19, or any combination thereof.

55. A method of treating HIV in a subject, the method comprising administering to the subject a population of cells heterologously expressing ALDH1 and one of: i) a heterologous nucleotide molecule encoding for at least one HIV co-receptor mutant, a mutation or plurality of mutations of at least one HIV co-receptor, at least one HIV fusion inhibitor, a molecule that reduces the expression of a HIV co-receptor, or any combination thereof; and at least one non-myeloablative dose of a chemotherapeutic agent.

56. The method of embodiment 55, wherein the cells express shCCR5, shCXCR4, and/or a C-peptide fusion inhibitor.

57. The method of embodiment 55, wherein the cell comprises a nucleic acid molecule comprising a sequence of 1, 3, 6, 7, 8, 9, 12, 13, 14, 16, 18, or any combination thereof.

58. The method of embodiment 55, wherein the cell comprises a nucleic acid molecule that encodes for a sequence of SEQ ID NO: 10, 11, 6, 7, 13, 15, 17, 19, or any combination thereof.

59. A method of expressing a molecule of interest in a subject, the method comprising administering to the subject a cell that heterologously expresses ALDH1 and the molecule of interest; and administering a non-myeloablative dose of cyclophosphamide.

60. The method of embodiment 59, wherein the cell is CD34+ and/or CD4+, or as otherwise as provided herein.

61. The method of embodiment 59, wherein the molecule of interest is one that reduces expression of the CCR5; reduces expression of the CXCR4; encodes for the expression of a C-peptide fusion inhibitor; or any combination thereof.

62. The method of embodiment 61, wherein the molecule of interest that reduces expression of the CCR5 is shCCR5.

63. The method of embodiment 62, wherein the molecule comprises a nucleic acid molecule comprising or encoding for SEQ ID NO: 6 and/or SEQ ID NO: 7.

64. The method of embodiment 61, wherein the C-peptide fusion inhibitor comprises a sequence of SEQ ID NO: 11, 15, 19, or any combination thereof.

The following examples are illustrative, but not limiting, of the compounds, compositions and methods described herein. Other suitable modifications and adaptations known to those skilled in the art are within the scope of the following embodiments.

EXAMPLES

Example 1

Engraftment Efficiency in Autologous Bone Marrow Transplant in Mice

Methods

Isolation of Bone Marrow. Bone marrow was flushed from femurs and tibia of 8- to 16-week-old syngeneic donor mice with Iscove's modified Dulbecco's medium (IMDM) containing 0.5 mM EDTA, 2% fetal bovine serum (FBS) and antibiotics. Cells were washed with buffer (phosphate-buffered saline [PBS] containing 5 mM EDTA and bovine serum albumin.

Transduction of Bone Marrow. Mouse bone marrow cells were transduced with a lentivirus vector expressing only EGPF (i.e., pLV-Puro-EF1A-EGFP ("Control Vector")) or a lentivirus vector expressing EGFP and human ALDH1A (i.e., pLV-Puro-EF1A-EGFP-hALDH1A, FIG. 4, SEQ ID NO: 2 ("Test Vector")) at MOI 10. 48 hours after transduction. Transduction efficiency was determined by FACS. Cells were then transplanted into irradiated mice as described below.

Transplantation. The syngeneic recipient mice (Balb/c) were pretreated on days −5 and −4 with 0.5 mg/kg fludarabine, day −2 with cyclophosphamide, and day −1 with busulfan. On the day of transplantation (day 0) mice were anesthetized and transplanted with $4 \times 10^6$ bone marrow cells per mouse in 100 μl IMDM by tail-vein injection. Hematopoietic recovery of transplants was monitored by FACS analysis of GFP.

Cyclophosphamide Treatment. Seven days after transplantation, mice received daily intraperitoneal (i.p.) injections of CTX at different doses: 0 mg/kg ("0 mg/kg post-transplantation CTX"), 16 mg/kg ("16 mg/kg post-transplantation CTX"), or 30 mg/kg ("30 mg/kg post-transplantation CTX"). During this study, treatment included 5 weeks of CTX, 1 week no CTX, followed by 1 week CTX treatment for a total of 6 weeks of CTX treatment.

Peripheral Blood GFP Analysis. Fifty microliters of peripheral blood from each mouse was collected retro-orbitally or from the tail vein and mixed with 1 ml PBS containing 0.5 mM EDTA. The cells were subjected to red blood cell lysis, washed in PBS and then further diluted in 400 ul PBS. The percentages of live $GFP^+$ granulocytes were analyzed using a flow cytometer.

Terminal Analysis of Bone Marrow. After 6 weeks CTX treatment, animals were sacrificed and the percentages of $GFP^+$ cells in bone marrow were assessed by flow cytometry. Granulocytes/neutrophils were identified using traditional forward vs. side scatter dispersion in which cells were plotted by size and internal complexity (granularity), respectively, in accordance with the refraction of light. For each no post transplantation CTX treatment group, n=3, for all other groups, n=6. After 6 weeks a white blood cell count in the blood was determined for each mouse. Results showed the presence of an outlier in each of the groups that were treated with CTX and those data were discarded for statistical analysis. Thus, for each no post transplantation CTX treatment group, n=3, for all other groups, n=5.

Results and Discussion

When observing the repopulation of the bone marrow after transplant, the peripheral blood can give an indication of the success of the transplant, but it is necessary to understand the cellular complexity of the immune cells before doing so because the bone marrow gives rise to various immune cells that have different life spans. For example, the life span of lymphocytes can be as long as 180 days, whereas the lifespan of neutrophils is just 5-7 days. Additionally, monocytes may live in the periphery just a few days, but they can also become tissue-resident, expanding their life-span to several months. Thus, if one were to analyze the lymphocyte population for reconstitution of donor bone marrow, one would not have an accurate reflection until all of the donor's pre-transplant lymphocytes have died off, 6 months after the procedure. To provide a more "real-time" reading of bone-marrow engraftment of recipient cells, the granulocyte population provides the best indication. As all of the donor's pre-transplant neutrophils die within 7 days, in the second week post-transplant, these cells are the most direct reflection of the bone marrow environment and the success of recipient transplant, which can also be measured by identifying the percentage of the transduced neutrophils, which reflects the engraftment rate.

Following the methods described above, blood was collected on days 23, 35, and 42 of the study (days 16, 28, and 35 of CTX administration, respectively) by retro-orbital bleed and the percentage of $GFP^+$ granulocytes in the peripheral blood of each mouse was assessed by flow cytometry.

Results showed that all groups of mice contained live $GFP^+$ granulocytes (FIG. 1). Additionally, on day 42 of the study, mice that were administered bone marrow cells transduced with the Test Vector (i.e., cells expressing $EGFP^+$ ALDH1A1) and treated with 16 mg/kg/day CTX showed a similar percentage of live $GFP^+$ granulocytes compared to mice administered bone marrow cells transduced with the Test Vector and treated with 30 mg/kg/day CTX (FIG. 1, compare "Test Vector, 16 mg/kg post-transplantation CTX" with "Test Vector, 30 mg/kg post-transplantation CTX").

Figure 2A:
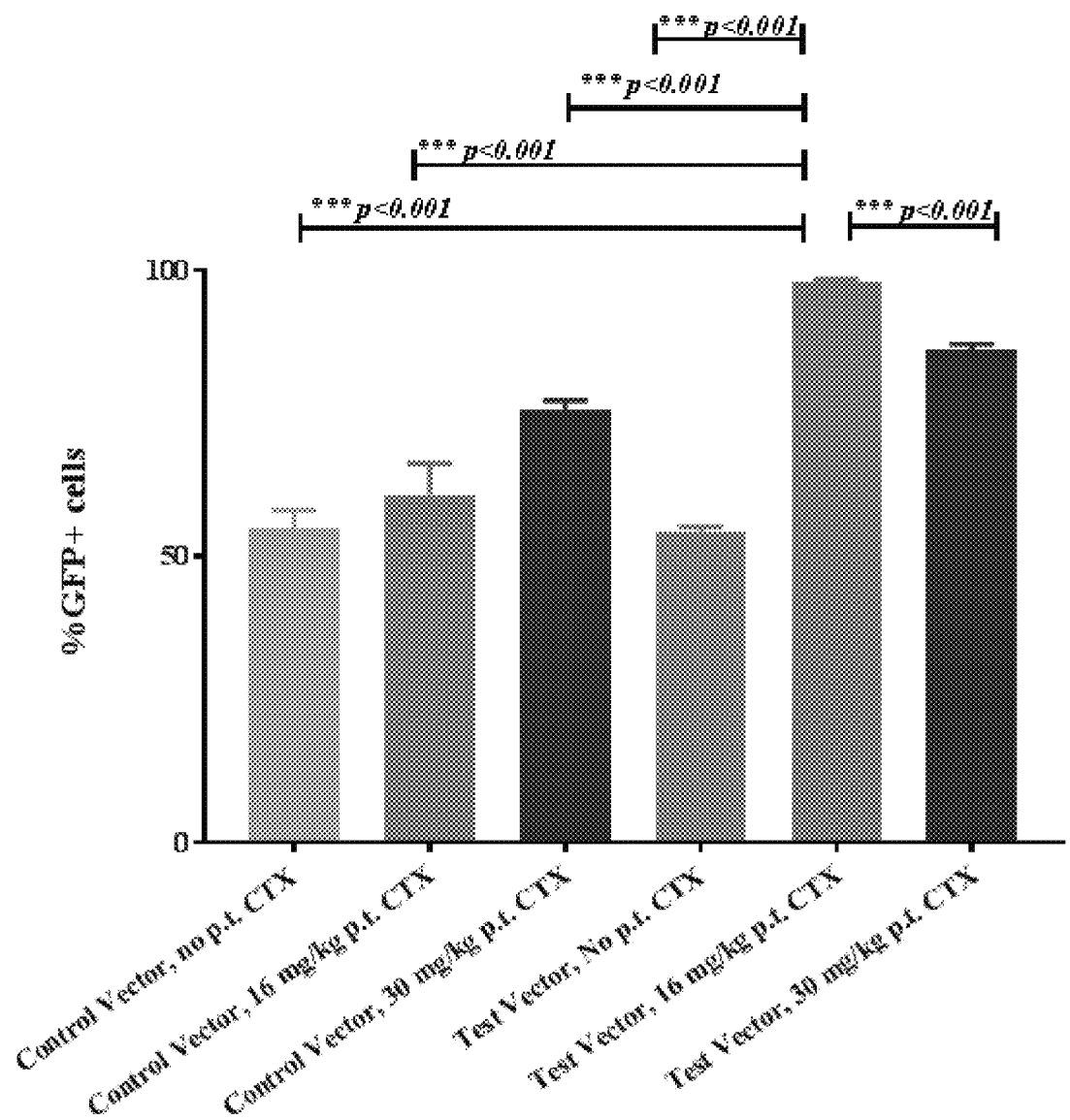
FIGS. 2A-2B depict the percentages of GFP$^+$ cells in bone marrow as assessed by flow cytometry for mice that were administered bone marrow cells transduced with Control Vector or bone marrow cells transduced with Test Vector and placed on a daily regime of CTX at the indicated concentrations. For each no post transplantation CTX treatment group, n=3, for all other groups, n=6.
Figure 2B:
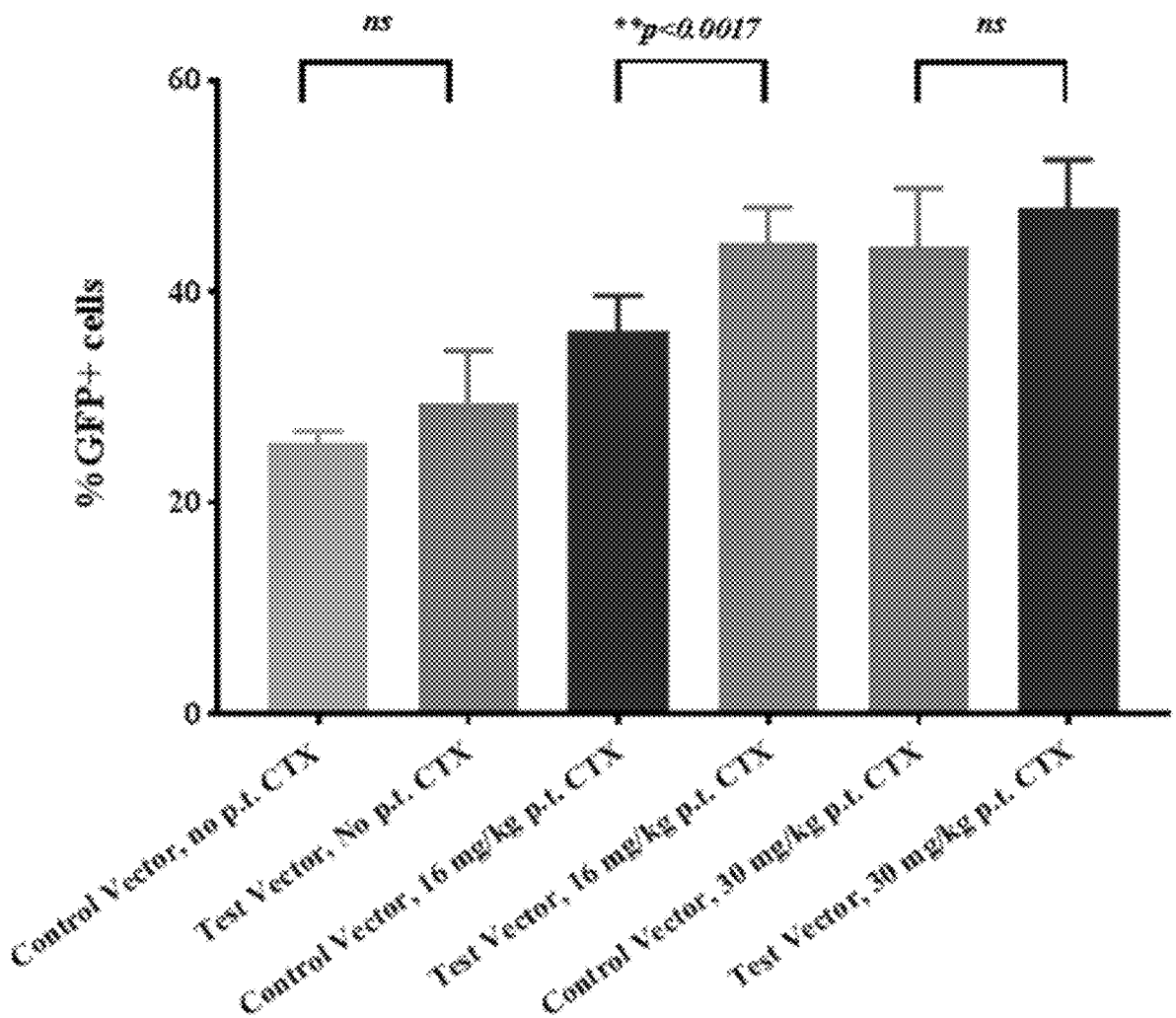

After 6 weeks, results demonstrated the presence of total $GFP^-$ cells (live and dead cells) (FIG. 2A). Engraftment was shown by the percentage of the live $GFP^+$ granulocytes/ neutrophil population (FIG. 2B). Surprisingly, both mice that were administered bone marrow cells transduced with the Test Vector (i.e., expressing EGFP +ALDH1A1) and treated with the non-myeloablative 16 mg/kg/day CTX and mice administered bone marrow cells transduced with the Test Vector and treated with the myeloablative 30 mg/kg/day CTX demonstrated a similar engraftment of greater than 40% (FIG. 2B, compare "Test Vector, 16 mg/kg p.t. post-transplantation CTX" with "Test Vector, 30 mg/kg p.t. post-transplantation CTX"). Moreover, mice that were administered bone marrow cells transduced with the Test Vector and treated with the 16 mg/kg/day CTX had a significantly higher percentage of engraftment compared with mice that were administered bone marrow cells transduced with the Control Vector and treated with the same dose of CTX (i.e., 16 mg/kg/day CTX) (FIG. 2B, compare "Test Vector, 16 mg/kg p.t. post-transplantation CTX" with "Control Vector, 16 mg/kg p.t. post-transplantation CTX").

Figure 3:
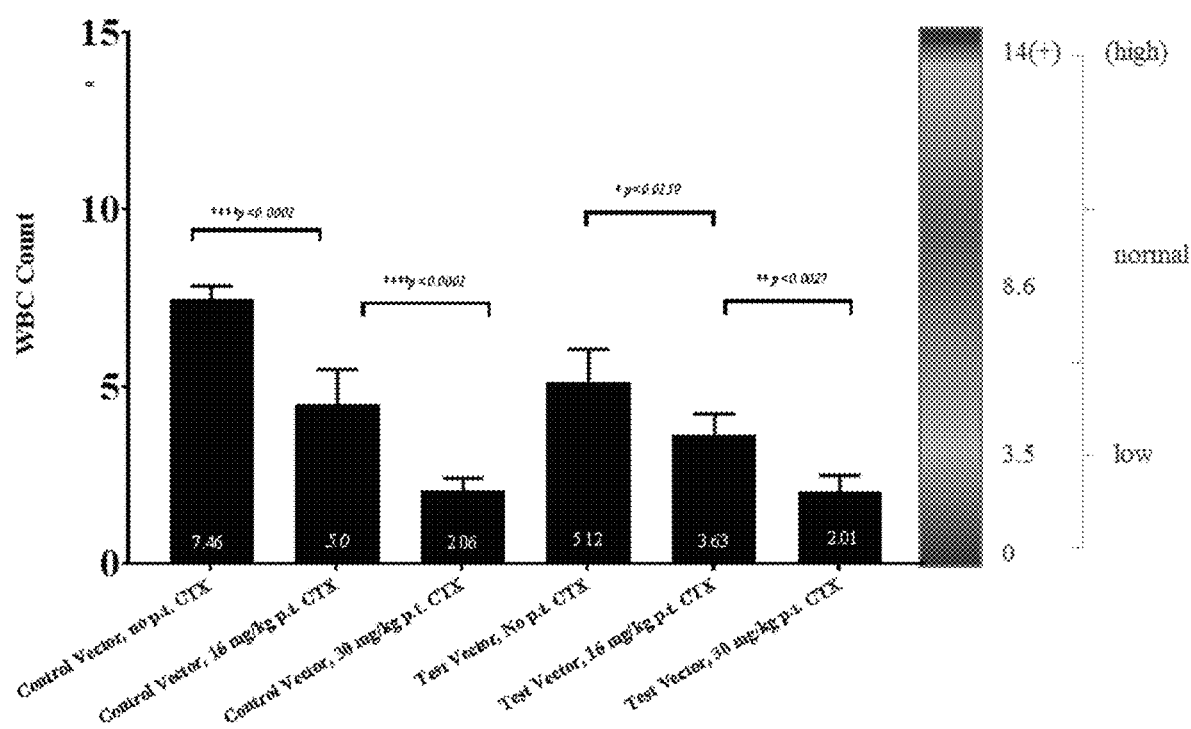
FIG. 3 depicts white blood cell (WBC) counts for mice administered bone marrow cells transduced with Control Vector or bone marrow cells transduced with Test Vector and placed on a daily regimen of CTX at the indicated concentrations. For each, no post transplantation CTX treatment group, n=3, for all other groups, n=5.
Figure 4:
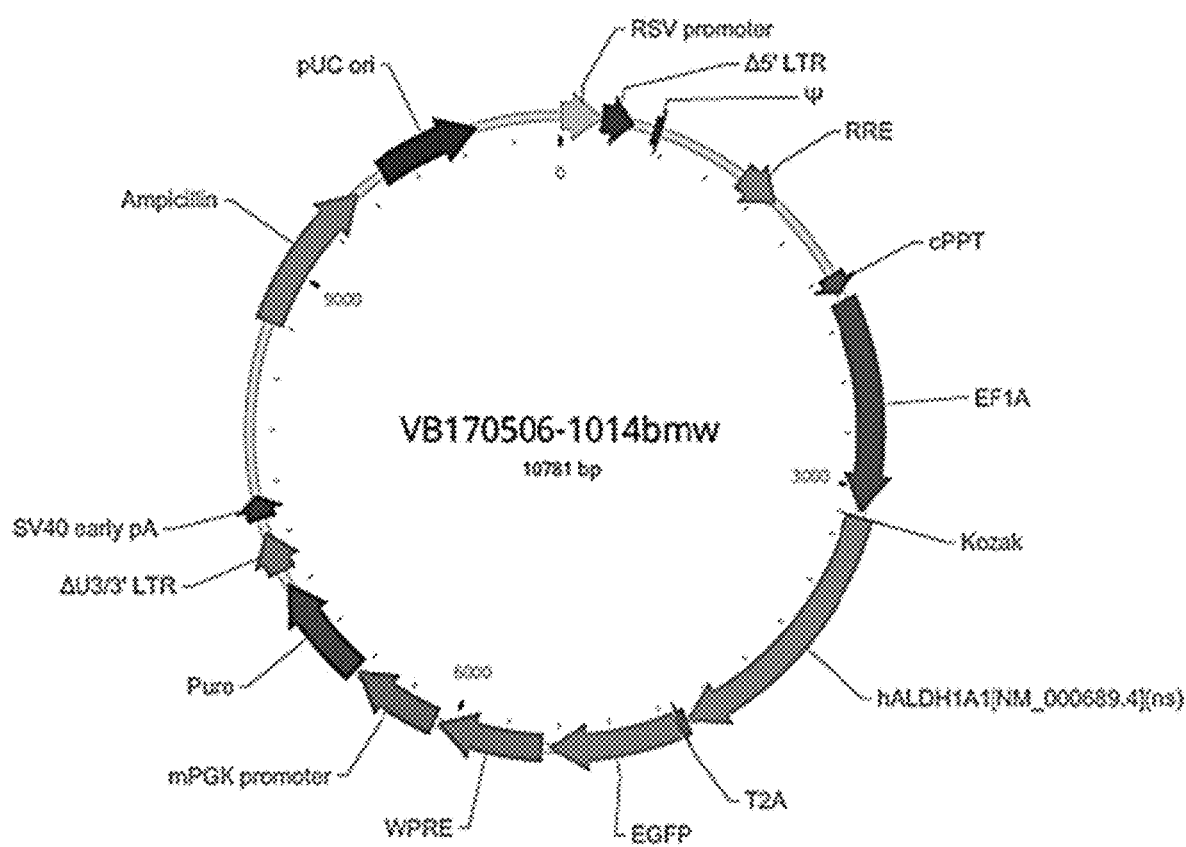
FIG. 4 depicts a non-limiting schematic of a lentiviral vector according to one embodiment of the present disclosure.
Figure 5:
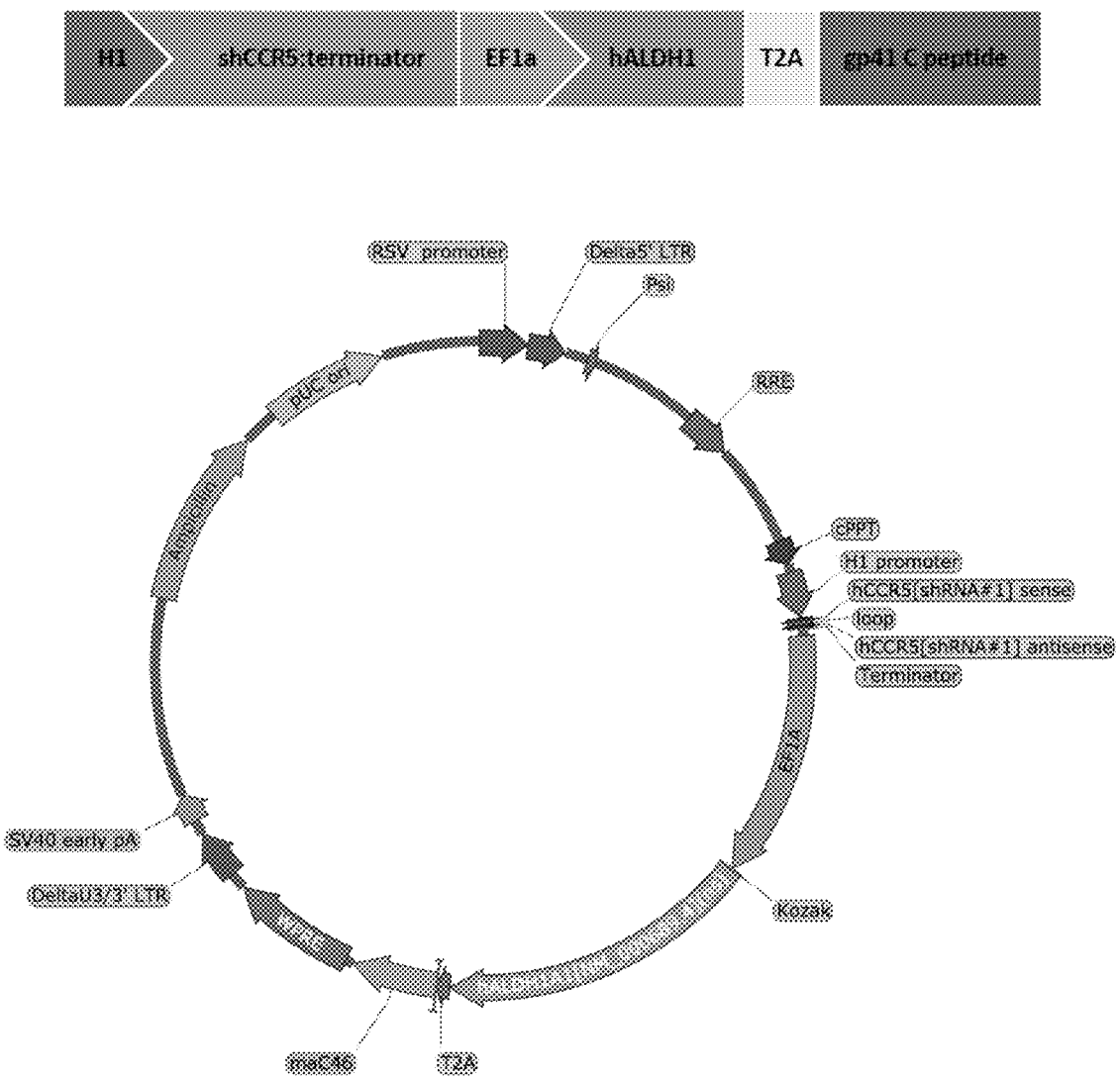
FIG. 5 depicts a non-limiting schematic of a lentiviral vector according to one embodiment of the present disclosure.
Figure 6:
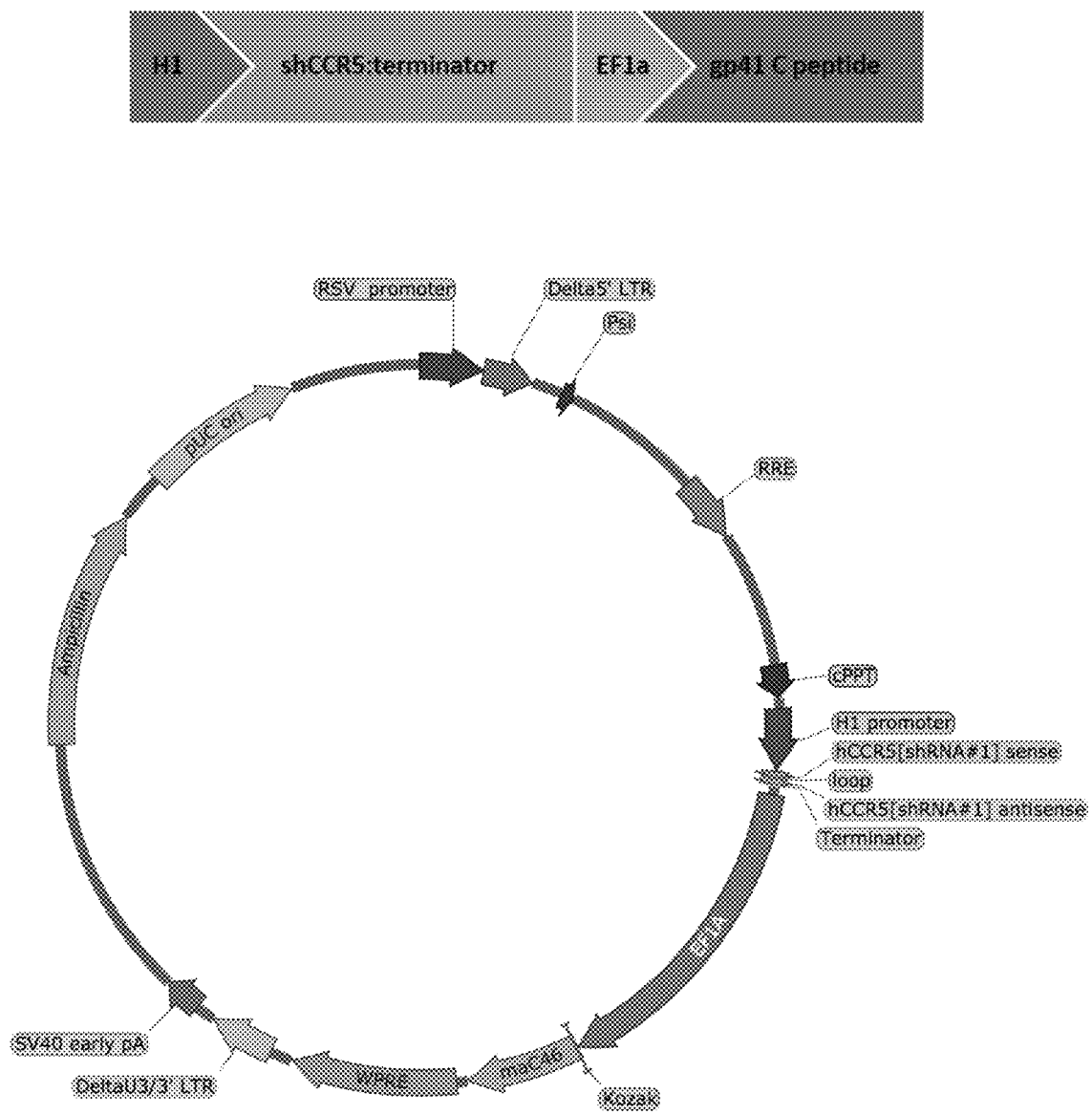
FIG. 6 depicts a non-limiting schematic of a lentiviral vector according to one embodiment of the present disclosure.

White blood cells (WBC) help to fight infections by attacking foreign agents that invade the body. WBC counts can be helpful for detecting hidden infections and/or susceptibility to infections. WBC counts in the peripheral blood were determined for each study group after 6 weeks of CTX treatment. As shown in FIG. 3, mice that were administered bone marrow cells transduced with either the Control Vector or the Test Vector with no CTX treatment had WBC counts within the normal range. For each CTX treated group there was one outlier, which was removed for statistical analysis. The ranges for high, normal, and low WBCs are according to known ranges in the art as provided for male mice in Charles River Research Models (BALB/C Mouse Hematology, North American Colonies, January 2008-December 2012), http://www.criver.com/files/pdfs/rms/balbc/rm_rm_r_balb-c_mouse_clinical_pathology_data.aspx. Notably, mice that were administered bone marrow cells transduced with the Test Vector and treated with the 16 mg/kg/day CTX had a significantly higher number of WBC compared with mice that were administered bone marrow cells transduced with the Test Vector and treated with 30 mg/kg/day CTX (FIG. 3, compare "Test Vector, 16 mg/kg p.t. post-transplantation CTX" with "Test Vector, 30 mg/kg p.t. post-transplantation CTX").

Example 2

In Vivo Humanized Mouse Studies #1

Purification of Stem Cells. Human PBMCs will be collected from healthy donors treated with 5 mcg/kg/day of granulocyte colony stimulating factor (G-CSF) (Amgen, Thousand Oaks, CA) for 5 days followed by leukapheresis on days 5 and 6. Patients will receive a regimen of 10 μg/kg filgrastim or G-CSF to mobilize the $CD34^+$ stem cells from the bone marrow into peripheral for isolation. Once the $CD34^+$ cell count in peripheral blood exceeds 10.0 to $20.0 \times 10^6$/kg body weight, apheresis will be performed. $CD34^+$ will be purified using positive selection enrichment followed by magnetic bead isolation. Samples will be washed in PBS containing 2% FBS, centrifuged and resuspended in PBS. CD34+ cells will then tested for purity by FACS analysis by CD34 staining, and the viability is assessed by trypan blue stain. Cells will then immediately be transplanted into mice. Proper written and informed consent will be obtained from donors in compliance with the Declaration of Helsinki protocols prior to collection.

Transplantation of Human HSC into NOG Mice. For adult mice, 10-12 week-old NOG mice. For newborn mice, mice at 1-2 days after birth will be used. Mice will be irradiated with 2-2.5 Gy for adult mice and with 1 Gy for newborns under SPF conditions one day before cell transfer. Mice weighing less than 18 g will sometimes die at this dose of irradiation. For adult mice, 0.25 mL ($1-0.5 \times 10^4$) of the cell suspension will be injected into the mice via the tail vein with a 1 mL syringe with a 27 G needle or a microinjector syringe with a 29 G needle under slight anesthesia with isoflurane.

Transduction of Stem Cells. $CD34^-$ cells from the same donor will be cultured in X-Vivo 10 media (Lonza) supplemented with 100 ng/ml of stem cell factor (SCF), thrombopoietin (TPO), and Fms-like tyrosine kinase 3 ligand (Flt-3L) (CellGenix, Freiberg, Germany) and optionally supplemented with IL-2, IL-3, IL-6, or any combination thereof, in fibronectin-coated vessels for 16 hours at 37° C. and 5% $CO_2$ at $1 \times 10^6$ cells/ml. The prestimulation media will then be removed and fresh culture media will be added, which additionally contains $1.35 \times 10^8$ to/ml vector ("Control Vector"=pLV-Puro-EF1A-EGFP or "Test Vector"=SEQ ID NO: 4, FIG. 5) and 4 mg/ml protamine sulfate (Sigma, Saint Louis, MO) representing a multiplicity of infection (MOI) of between MOI of 2 and MOI of 50. This transduction mix will be returned to the incubator for between 12 and 48 hours. Transduced cells will be lifted with trypsin (Lonza, Walkersville, MD), washed, resuspended in PBS and immediately transplanted into mice (as described above, without irradiation).

Figure 8:
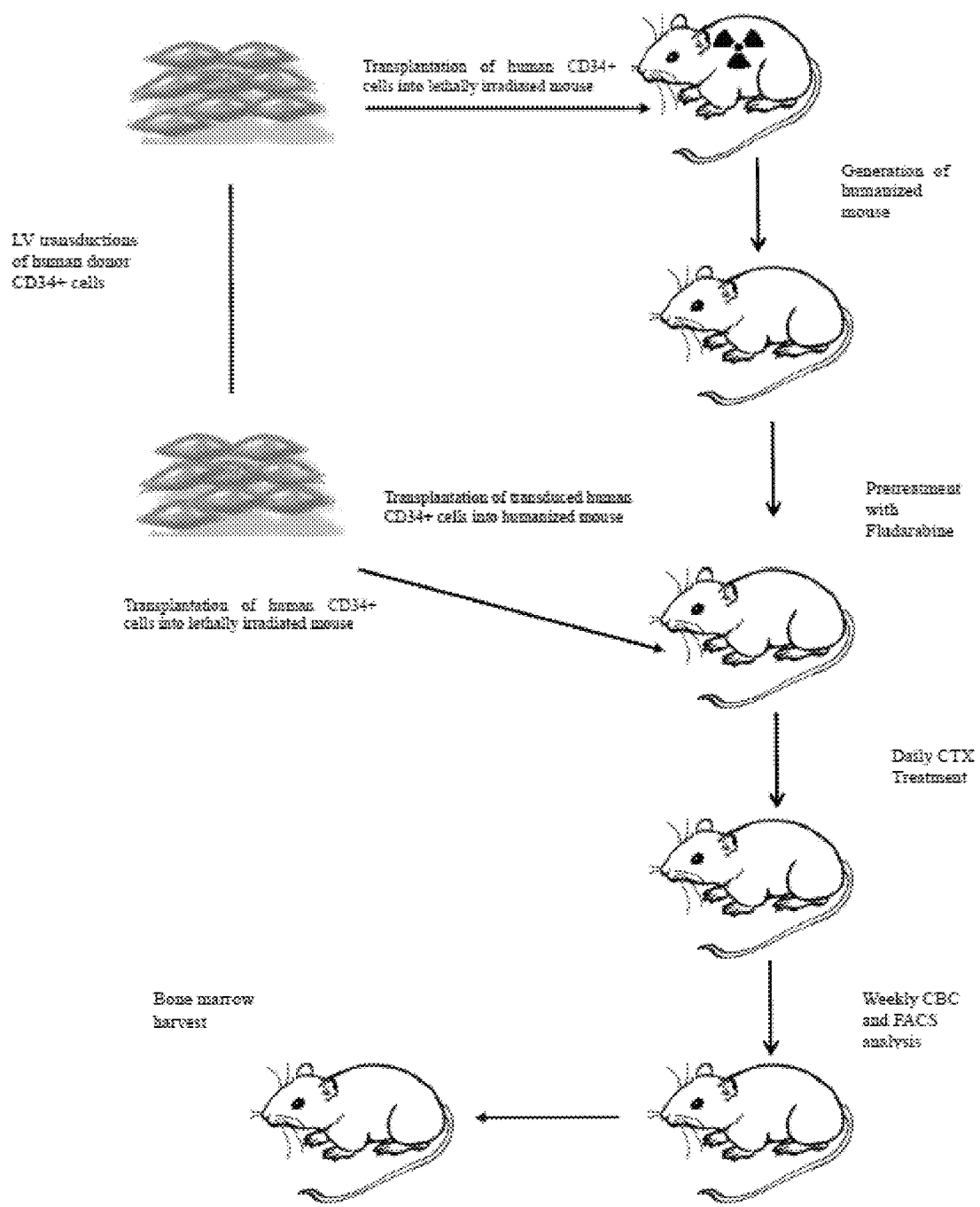
FIG. 8 depicts a non-limiting schematic of a study design for a lentiviral vector expression and efficacy of shRNA knockdown study.

Peripheral blood GFP analysis and terminal analysis of spleen, blood and bone marrow will be performed as described above. A schematic representation of the study is shown in FIG. 8, but this representation is merely for illustrative purposes only and other study designs can be used.

Example 3

In Vivo Humanized Mouse Studies #2

Purification of Stem Cells. Human PBMCs will be collected from healthy donors treated with 5 mcg/kg/day of granulocyte colony stimulating factor (G-CSF) (Amgen, Thousand Oaks, CA) for 5 days followed by leukapheresis on days 5 and 6. $CD34^+$ will be purified by positive selection using immune-magnetic beads. Samples will be washed in PBS containing 0.5% HSA, centrifuged and resuspended in PBS. $CD34^+$ cells will then be tested for purity by flow cytometry analysis by CD34 staining, and the viability dye. Cells will then immediately be transplanted into mice. Proper written and informed consent will be obtained from donors in compliance with the Declaration of Helsinki protocols prior to collection.

Transplantation of Human HSC into NOG Mice. For adult mice, 10-12 week-old NOG mice will be used. For newborn mice, mice at 1-2 days after birth will be used. Mice will be irradiated with 2-2.5 Gy for adult mice and with 1 Gy for newborns under SPF conditions one day before cell transfer. Mice weighing less than 18 g will sometimes die at this dose of irradiation. For adult mice, 0.25 mL ($1-0.5 \times 10^4$) of the cell suspension will be injected into the mice via the tail vein with a 1 mL syringe with a 27 G.

Transduction of Stem Cells. $CD34^-$ cells from the same donor will be cultured in X-Vivo 10 media (Lonza) supplemented with 100 ng/ml of stem cell factor (SCF), thrombopoietin (TPO), and Fms-like tyrosine kinase 3 ligand (Flt-3L) (CellGenix, Freiberg, Germany) and optionally supplemented with IL-3 and IL-6 in fibronectin-coated vessels for 16 hours at 37° C. and 5% $CO_2$ at $1 \times 10^6$ cells/ml. The prestimulation media will then be removed and fresh culture media will be added, which additionally contains $1.35 \times 10^8$ ul/ml vector ("Control Vector"=pLV-Puro-EF1A-EGFP or a "Test Vectors" and representing a multiplicity of infection (MOI) of between MOI of 2 and MOI of 50 Suitable "Test Vectors" include any one or combination of:

| Test Vector |
| --- |
| H1 > shCCR5-EF1a > ALDH1:2A:C-peptide |
| H1 > shCCR5-EF1a > ALDH1:2A:maC46 |
| H1 > shCCR5-EF1a > ALDH1 |
| EF1a > ALDH1:2A:C-peptide |

This transduction mix will be returned to the incubator for between 12 and 48 hours. Transduced cells will be harvested, washed, resuspended in PBS and immediately transplanted into mice (as described above, without irradiation).

Peripheral blood GFP analysis and terminal analysis of spleen, blood and bone marrow will be performed as described above. A schematic representation of the study is shown in FIG. 8, but this representation is merely for illustrative purposes only and other study designs can be used.

Example 4

Lentiviral Proof of Concept Study

Lentiviral Vector Expression. Human CD34+ cells will be transduced with lentiviral (LV) vectors containing four expression cassettes. The expression levels of ALDH and C-peptide, the knockdown of shRNA-mediated CCR5, and optionally knockdown of shRNA-mediated CXCR4 will be assessed in transduced cells. The cellular C-peptide expression will then be correlated to knockdown of CCR5.

Briefly, CSF mobilized, cryopreserved human CD34+ cells will be thawed in 37° C. until the contents of vial are completely in liquid phase. Cells will be transferred to sterile 15 mL conical tube (Corning, Tewksbury, MA). Dropwise, and with gentle agitation, pre-warmed media X-Vivo 10 Serum Free media (Lonza, Basel, Switzerland) will be added to 15 mL. Cells will then be centrifuged at 200-300×g for 5 min. After aspirating the supernatant, the pellet will be resuspended in 10 mL media and a small aliquot will be retained for counting and viability determination. Cells will then be centrifuged, supernatant aspirated, and resuspended to a density of $1.0\times2.0\times10^6$ cells/m and transfer to a T75 cm$^3$ tissue culture flask (Corning, Tewksbury, MA).

Cells will be pre-stimulated by adding 100 ng/mL of each of stem cell factor (SCF), thrombopoietin (TPO), and flt3/flk2 ligand (Flt3L) (R&D Systems, Minneapolis, MN) to culture media and then cultured in a 5% $CO_2$ incubator at 37° C. for 24 h. Afterwards, the cells will be removed from the incubator and centrifuged. Cells will be resuspended at a density of $1.0\times10^6$ cells/mL in X-Vivo 10 media supplemented with 100 ng/mL of both SCF and Flt3L, 10 ng/mL TPO, and 60 ng/mL of IL-3. $1.0\ 10^6$ cells will then be seeded per well of a 12-well non-tissue culture treated, Rectronectin (5 µg/cm$^2$) coated plate (TaKaRa Bio, Shiga, Japan).

Lentiviral particles will be thawed (CCR5.Cpeptide.LV or CCR5.C peptide.ALDH.LV) at 37 C and gently mixed upon thaw. Each of the particles will be added to culture at MOI of about to 2 to 50, such as 9, and mix by gently swirling the plate. Cells will then be returned to 5% $CO_2$ incubator at 37° C. and cultured for 24 to 48 h. Afterwards, samples will be retained for cell count, viability and transduction efficiency by flow cytometry and qRTPCR assessment.

The remaining cells will be centrifuged, supernatant gently aspirated, and 1 mL/well of fresh X Vivo 10 media added to each well. The plate will be returned to incubator. Cells can be expanded for up to three days post-transduction.

Flow cytometry staining and analysis will immediately proceed. If LV constructs contain fluorescent marker, acquisition on MacsQuant FACS Analyzer will occur. If no fluorescent marker is contained in vector, staining procedure for target protein or HIV-1 LTR transcriptional activation) will occur.

Cells can be used for further characterization. If no further characterization is necessary, immediately following transduction (or post-transduction expansion), cells will be cryopreserved at a density of $5\times10^6$ cells/mL in a solution of 50% IMEM (Thermo Fisher Scientific, Carlsbad, CA), 45% Human Serum Albumin (HAS) (Sigma-Aldrich, St. Louis, MO), and 5% 0.2 µm-filtered DMSO in a control-rate freezer. Cells can then either be immediately transferred to liquid nitrogen or shipped on dry ice.

Chemoprotection. Human CD34+ cells transduced with LV vectors which exhibit ALDH expression (e.g., SEQ ID NO: 2 or SEQ ID NO: 5) are treated with various doses of cyclophosphamide to demonstrate resistance to chemotherapeutic agent. The experiment can also be performed by treating mixed cultures of transduced and non-transduced cells with various doses of maphosphamide. The survival of both transduced and non-transduced cells will be measured after treatment at each dose of cyclophosphamide.

Briefly, lyophilized maphosphamide is resuspended to a working stock solution of 1 mg/mL in sterile water. Transduced cells are then washed once in regular media (RPMI+ 10% FBS) and transduced cells (both test vector (e.g., SEQ ID NO: 4) and control vector (e.g., SEQ ID NO: 5)) are resuspended to a density of $0.5\times10^6$ cells/mL in MethoCult 3330 medium (StemCell Technologies, Vancouver, BC, Canada). The final solution may consist of 0.8% methylcellulose in α-medium, supplemented with FBS, erythropoietin (1 U/ml), IL-3 (200 U/ml), IL-6 (200 U/ml), SCF (100 ng/ml), IL-10 (200 ng/ml) and granulocyte colony-stimulating factor (Stem Cell Technologies) at 100 ng/ml.

To each set of dishes (control and test) maphosphamide will be added to the following final concentrations: 0.15, 2.5, 5, 10, 15, 20 µM. Plates will then be incubated at 37°C, 5% $CO_2$ for 14 days. After 14 days, colonies will be scored in each plate using an inverted light microscope. Mann-Whitney U tests will then be performed to determine any significant statistical difference in the number of colonies formed by test vector and control vector expressing cells.

Example 5

Fusion Inhibition Studies

T cells isolated from spleens and thymus of humanized mice will be co-cultured with HIV strains as described above. The C44 expression level will be evaluated using an anti-Gp41 antibody that recognizes the C peptide detected by flow cytometry. The C-peptide expression level (percentage of positive and median fluorescence intensity) will then be correlated to the extent of HIV fusion blockade.

Materials and Reagents. 293T cells (ATCC); pAdVantage (Promega Corporation); pCMV4-BlaM-Vpr (Addgene); pNL4-3 proviral DNA (NIH AIDS Reagent Program) or TN6-GFP encoding primary Env; DMEM (Mediatech, Cellgro®); RPMI 1640 (Mediatech, Cellgro®); 1× phosphate-buffered saline (PBS); Fetal bovine serum (FBS); 100 U/ml of penicillin and 100 U/ml of streptomycin (Thermo Fisher Scientific, Gibco®); 2M CaCl2; Alliance HIV-I p24 ELISA kit (PerkinElmer) or FlaQ assay reagents (Hayden et al., 2003); Peripheral blood lymphocytes (PBLs); CCF2-AM substrate and loading solutions (Thermo Fisher Scientific); $CO_2$-independent media (Thermo Fisher Scientific, Gibco®); Probenecid (Sigma-Aldrich); Mouse antihuman CD3 conjugated to APC-Cy7 and mouse antihuman CD4 conjugated to PE-Cy7 (BD Biosciences); BD CompBeads (BD Biosciences); 16% Paraformaldehyde (Electron Microscopy Sciences); HBSS (see Recipes); Dulbecco's modified Eagle medium (DMEM) culture media (see Recipes); Roswell Park Memorial Institute (RPMI) culture media (see Recipes); CCF2 loading solution (see Recipes); Stock solution of probenecid (250 mM) prepared in 250 mM NaOH (see Recipes); Development media (see Recipes).

Vector. pLV[Exp]-H1>hCCR5 [shRNA] EF1A>hALDH1A1[NM_000689.4](ns):T2A:{C peptide} (e.g., SEQ ID NO: 4)

Recipes. HBSS (280 mM NaCl; 10 mM KCl; 1.5 mM $Na_2HPO_4$; 12 mM dextrose; 50 mM N-(2-hydroxyethylpiperazine)-N'-(2-ethanesulfonic acid) (HEPES) (pH 7.05); store at −20° C.).

Flow cytometrystaining buffer (lx phosphate-buffered saline without Ca++ and Mg++ (PBS); 0.5% HSA; store at 4° C.).

Dulbecco's modified Eagle medium (DMEM) culture media (DMEM; 10% heat inactivated fetal bovine serum; 100 U/ml of penicillin; 100 µg/ml of streptomycin).

RPMI culture media (RPMI 1640; 10% heat inactivated fetal bovine serum; 100 U/ml of penicillin; 100 µg/ml of streptomycin).

CCF2 loading solution: Resuspend CCF2-AM in dimethylsulfoxide (solution A of the CCF2 kit) to generate a stock solution (1 mM CCF2-AM). Divide into aliquots and store in the dark at −80° C. Mix by vortex-mixing 1 µl of 1 mM CCF2-AM with 9 µl of a solution containing 100 mg/ml of Pluronic-F127 and 0.1% acetic acid (solution B of the CCF2 kit). Add 1 ml of CO2-independent media and vortex again. Stock solution of probenecid (250 mM) prepared in 250 mM NaOH. Divided into aliquots and store at −20° C.

Development media (2.5 mM probenecid; 10% fetal bovine serum in $CO_2$-independent media).

Equipment. T175 cm2 culture flasks; 96-well V-bottom plate (Corning Incorporated); 5-, 10-, 25-ml pipettes; 50-ml Falcon tube; 0.22 µm poresize Steriflip (EMD Millipore); 2 ml Nalgene tubes (Thermo Fisher Scientific); Clear ultracentrifuge tubes (BD); 37° C., 5% $CO_2$ incubator; Ultracentrifugation equipment with SW28 rotor; Flow cytometer. The fusion assay alone requires a flow cytometer equipped with a violet laser excitation (405 nm) and two measurement parameters. The photomultiplicator tube (PMT) with a 450/50 nm band pass filter, commonly used for the detection of Pacific Blue, is used for the detection of the cleaved CCF2 substrate. The other PMT with a 515/20 nm band pass filter, commonly used for Amcyan detection, is used for the detection of the uncleaved CCF2 substrate. Additional PMTs are necessary for the measurement of the fluorochromes associated with the CD3 and CD4 antibodies. APC-Cy7 is excited by 633 nm red laser and detected with a PMT with a 755 long pass filters. PE-Cy7 is excited by a 531 nm yellow-green laser and detected with the PMT with a 755 long pass filter.

Software. FlowJoX software (Tree Star) or other FACS analysis software.

Fusion Inhibition Assay. $1.5 \times 10^7$ 293T cells will be plated in a T175-cm² tissue culture flask with 20 ml of DMEM culture media and cultured overnight at 37° C. in a 5% $CO_2$ humidified incubator. 1.75 ml of $H_2O$ containing 60 µg of TN6-GFP proviral DNA, 20 µg of pCMV-BlaM-Vpr, and 10 µg of pAdVantage vectors will be prepared. 2 ml of 2xHBSS will then be slowly added and mixed gently by pipetting up and down. 250 µl of 2 M $CaCl_2$ will be added dropwise. DNA will be precipitated by incubating for 10 min at room temperature. The 293T cell culture media will be replaced with 40 ml of fresh DMEM culture media pre-warmed to 37° C. Next, 4 ml of DNA precipitate will be added and incubated for 16 h at 37° C. The media will then be replaced with 40 ml of fresh DMEM culture media pre-warmed to 37° C. and incubated for 24 h at 37° C.

The supernatant of the transfected 293T cells will be harvested into a 50-ml Falcon tube and centrifuged at room temperature for 10 min to remove the cellular debris. The clarified supernatant will then be filtered through Steriflip. 36 ml of virion-containing supernatant will be transferred to Ultra-Clear centrifuge tubes. The tubes will be placed in the bucket of the SW28 rotor, balanced with DMEM culture media, if necessary, and ultracentrifuged (72,000×g, 90 min) at 4° C. without using brakes. The supernatant will be removed and the viral pellet resuspended in 1 ml of DMEM, divided into 100-µl aliquots, and stored at −80° C.

The $p24^{Gag}$ content of the viral preparation will be quantified by Enzyme-Linked Immunosorbent Assay or FlaQ Assay (Maiti et al., 2014).

The PBLs will be washed with RPMI culture media, counted PBLs, and suspended in RPMI culture media at $2 \times 10^7$ cells/ml. The cell suspension will be divided in aliquots of 100 µl ($2 \times 10^6$ cells) per condition to be tested in a V-bottom 96-well plate. Two additional aliquots of cells will be distributed into two wells to serve as compensation controls. One well will be loaded with CCF2 substrate while the other will remain unloaded. These two control wells will not be stained with anti-CD3-APC-Cy7 and anti-CD4-PE-Cy7 antibodies.

A quantity of HIV-1 virions containing BlaM-Vpr equivalent to 400 ng of $p24^{Gag}$ will be added to all wells except the "non-infected control" and the two compensation controls and incubated for 2 h at 37° C.

Cells will then be collected by centrifugation for 5 min at room temperature and washed once with 200 µl of $CO_2$-independent media and centrifuge for 5 min at room temperature. The pellet will be resuspended in 100 µl of CCF2-AM loading solution and incubated for 1 h at room temperature in the dark being sure to keep one well unstained by resuspending with $CO_2$-independent media only. Cells will be collected by centrifugation at 365×g for 5 min at room temperature. The collected cells will next be washed with 200 µl of development media, centrifuged for 5 min at room temperature, and the pellet resuspended in 200 µl of development media and incubated the cells at room temperature for 16 h in the dark.

To two empty wells, each of the BD compensation beads vials (negative control and anti-mouse IgK) will be added dropwise. The cells and beads will then be collected by centrifugation for 5 min at 4° C. Cells and beads will then be washed once by addition of 200 µl of FACS staining buffer, collected by centrifugation for 5 min at 4° C., and the pellet resuspended in 100 µl of immunostaining solution (in Flow cytometry staining buffer) containing a 1/100 dilution of anti-CD3-APC-Cy7 and a 1/50 dilution of anti-CD4-PE-Cy7. The two compensation controls nor the beads will be stained. The CompBeads will be stained with the flow cytometry staining buffer containing either a 1/100 dilution of anti-CD3-APC-Cy7 or a 1/50 dilution of anti-CD4-PE-Cy7. Samples will be incubated for 30 min at 4° C.

After a 30-minute incubation at 4° C., the cells and beads will be collected by centrifugation for 5 min at 4° C. The cells and beads will then be washed with 200 µl of flow cytometry staining buffer. Flow cytometry staining buffer supplemented with 1.2% paraformaldehyde will be used to fix the cells for 24 h at 4° C.

A flow cytometer—MACSQuant instrument will be used to acquire the samples. The set of samples include: unloaded unstained cells, the CCF2 loaded unstained cells, the CD3-APC-Cy7 stained beads, the CD4-PE-Cy7 stained beads, the non-infected control loaded with CCF2 and immunostained, and the infected samples loaded with CCF2 and immunostained. Data to be analyzed using FlowJo.

Example 6

HIV Challenge: Lentivirus Vector Transduced Human CD4+ T Cells

GFP reporter CD4+ T cells transduced with LV containing CCR5shRNA/c-peptide/ALDH or T cells transduced with LV containing empty control vector will be cultured with R5, X4, or both laboratory HIV strains. HIV infectivity will be analyzed by reporter marker (if using a T cell reporter line) or by p24 ELISA.

Example 6

HIV Challenge: Lentivirus Vector Transduced Human CD4+ T Cells

GFP reporter CD4+ T cells transduced with LV containing CCR5shRNA/c-peptide/ALDH or T cells transduced with LV containing empty control vector will be cultured with R5, X4, or both laboratory HIV strains. HIV infectivity will be analyzed by reporter marker (if using a T cell reporter line) or by p24 ELISA.

Example 7

Dose Range and Lentiviral Vector Efficacy Study

Sca1+/c-kit− stem and progenitor cells transduced with lentivirus containing CCR5shRNA/C-peptide/ALDH expressing vector or control empty vector will be implanted into pre-conditioned C57BL/6 syngeneic mice.

Briefly, after seven days, all mice will begin a daily regimen of cyclophosphamide (CTX) treatment. Both groups of mice will be treated with various dosages of CTX (6 mice/per group/per dose): 0, 10, 13, 16, 19, and 40 mg/kg. One week following the commencement of CTX treatment, mice will be bled on a weekly basis. A complete blood count (CBC) panel will be run to monitor any cytotoxic effects of the chemotherapy (engraftment efficacy: ALDH conference of CTX resistance), while flow cytometry analysis will measure lineage specific marker expression as well as C-peptide and CCR5 expression in these cells (expression efficiency: efficacy of shRNAs to knockdown target genes). The study will continue for at least 10 weeks of CTX treatment or until full bone marrow engraftment is reached. A schematic of the study is provided in FIG. 7 and a more detailed protocol is provided below.

Materials and Reagents. Easy Sep™ Mouse Hematopoietic Progenitor Cell Isolation Kit (StemCell Technologies); Falcon 15 mL Conical tube (Corning); 5 mL (12×75 mm) polystyrene round-bottom tube (Corning); StemSpan serum-free medium (StemCell Technologies); Mouse Hematopoietic Stem Cell Expansion Kit Cytokine Panel (R&D); RetroNectin Recombinant Human Fibronectin Fragment (Clontec); RPMI-1640 (Thermo Fisher Scientific); Petri-dish (Thermo Fisher Scientific); HBSS (Thermo Fisher Scientific); 27 G×½ needle (BD); Centrifuge (Thermo Fisher Scientific); Sorvall ST 40R Countess II automated cell counter (Thermo Fisher Scientific); Trypan blue (Thermo Fisher Scientific); Lineage Cocktail (mCD3, mGr-1, mCD11b, mB220, mTer119) (include isotype controls) (Biolegend); Ly-6A/E (Sca-1) (Thermo Fisher Scientific); CD117 (c-kit) (Thermo Fisher Scientific); Viability Dye eFluor 506 (Thermo Fisher Scientific); Anti-Mouse CD16/32 FC Block (Biolegend); Cell Staining Buffer (Biolegend); Balb/c Female Mice (Charles River).

Vector. pLV[Exp]-H1>hCCR5[shRNA]-EF1A>hALDH1A1[NM_000689.4](ns):T2A:{C peptide} (e.g., SEQ ID NO: 4)

Progenitor cell isolation from bone marrow (# of progenitor cells needed). From table below, calculate number of (donor) mice needed to provide # cells needed from transduction

| | Number of mice for transplantation | Total number of cells (200,000/mouse) | Total number of cells (500,000/mouse) |
|---|---|---|---|
| V1 treatment vector | 36 | 7,200,000 | 18,000,000 |
| V2 treatment vector | 36 | 7,200,000 | 18,000,000 |
| #cells needed from transplantation | 72 | 14,400,000 | |
| #cells needed from isolation | | | 36,000,000 |

Mouse bone marrow isolation. BALB/c mise (female, 20 to 25 g, 8-10 weeks old) will be euthanized by $CO_2$ asphyxiation. Subsequent experimental steps will be conducted in a laminar air flow Biosafety Cabinet (BSC). Bone marrow cells will be collected from the femur. Briefly, the contents of marrow will be flushed with 2 ml of HBSS using a 1-ml insulin syringe with a 27G×½ needle. The contents will be collected into a sterile 50-ml centrifuge tube. The BM cell suspension collected above will then be diluted with RPMI-1640 to a final volume of 7.5 ml. Any clusters within the bone marrow suspension will be disintegrated by vigorous pipetting. The cells will then be centrifuged, washed, and centrifuged again. The cell pellet from each femur will be gently resuspended in 7.5 ml of RPMI-1640 to prepare a homogeneous suspension. An aliquot of cell-suspension will be removed for total cell count and viability usingNC-200 automated cell counter.

Progenitor cell isolation. The isolated cells will be transferred to a fresh tube, spun down, and resuspended in EasySep Buffer (PBS+2% FBS+1 mM EDTA) within a volume range 0.5-2 mL to achieve a concentration of $1 \times 10^8$ cells/mL. Rat serum will then be added to the sample at 50 µL/mL and the sample will be transferred to 5 mL (12×75 mm) polystyrene round-bottom tube. EasySep Mouse Hematopoietic Progenitor Cell Isolation cocktail will then be added to sample at 50 µL/mL of sample. The sample will be mixed and incubated in 4° C. for 15 minutes. Rapid spheres will be vortexed for 30 seconds then added to the sample at 75 µL/mL. The sample will be mixed and incubated in 4° C. for 10 minutes and then brought up to a total volume of 2.5 mL using EasySep Buffer. Progenitor cells are isolated using magnetic sorting.

Evaluation of isolated progenitor cells by flow cytometer. Cells will be transferred to a new 96-well plate, spun down and re-suspended in 504, of FACS Buffer (PBS+2% FBS+1 mM EDTA). 3 µL of FC Block (Anti-CD16/32) will be added to each sample and incubated at 4° C. for 15 minutes. The following panel and amounts will be used:

| Marker | Fluorophore | Clone | Volume per Sample |
|---|---|---|---|
| Lineage Cocktail (mCD3, mGr-1, mCD11b, mB220, mTer119) | FITC | 145-2C11, RB6-8C5, M1/70, RA3-6B2, Ter-119 | 20 µL |

-continued

| Marker | Fluorophore | Clone | Volume per Sample |
|---|---|---|---|
| Ly-6A/E (Sca-1) | PE | D7 | 2 μL |
| CD117 (c-kit) | APC | 2B8 | 2 μL |
| Viability Dye | eF506 | N/A | 0.1 μL |

Controls will include: Fluorescence Minus One (FMOs) controls for CD117, Ly6A/E and Lineage cocktail isotype controls.

Each well will be brought up to a total volume of 1004, and incubated in the dark at 4° C. for 30 minutes. Cells will then be washed with 2004, of Flow cytometer Buffer and resuspended in a volume. Flow cytometers to be acquired on MAC SQuantCytometer. Purity will be calculated by summing % of Sca1-/c-kit+, Sca1+/c-kit Sca1+/c-kit + and multiplying by the percent of live lineage cocktail negative events.

Lentivirus transduction and progenitor expansion. On Day 0, 12- or 24-well plates will be coated with 0.3 ml RetroNectin (100 ng/ml) and incubated for at least 2 hrs at room temperature. The coating media will then be aspirated from the plate, the plate blocked with 2% BSA in 1×PBS at room temperature for at least 30 minutes, and then washed 3 times with 1×PBS. The plate is then ready for use. Care to be taken to not let the plate dry.

Fresh isolated bone marrow progenitor cells will be seeded at between approximately 0.20.4×10$^6$ cells/ml in bone marrow progenitor cell culture media. The lentivirus will be added to the cell (MOI=3) for 24 hours.

On Day 1, the cells will be spun down and get rid of lentivirus containing media and fresh bone marrow progenitor cell culture media will be added.

On Day 2, after lentiviral transduction, puromycin (1 μg/ml) will be added to the bone marrow progenitor cell culture media to select lentivirus infected cells. Cells will be treated for 4 days.

On Day 4, fresh media with puromycin will be added.

On Day 6, cells will be spun down fed fresh media without puromycin.

On Day 7, cells will be collected for cell counting and run GFP flow to determine the transduction efficiency. Fresh bone marrow progenitor cell culture media will be fed to remaining cells The bone marrow progenitor cells will be cultured for another 3 days until Day 10 with media change at Day 9.

On Day 10, the cells will be harvested for counting and Flow cytometry analysis performed to determine the transduction efficiency.

| Sample # | Lentiviral MOI | Puromycin (1 μg/ml) selection |
|---|---|---|
| 1 | V null-empty control vector | Yes |
| 2 | V2 treatment vector-Lenti-ALDH1/Cpeptide/CCR5 MOI = 3 (SEQ ID NO: 4) | Yes |

Bone Marrow Progenitor Cells Transplantation and Treatment—Precondition. Before the transplantation, mice will receive two doses of a Fludarabine (5 mg/Kg for 2 days). At day 0 (two days after treatment with Fludarabine), 36 mice will be transplanted with control vector transduced stem and progenitor cells via IV, 36 mice will be transplanted with test vector transduced stem and progenitor. After transplantation, the animals will be checked daily for morbidity and mortality. At the time of routine monitoring, the animals will be checked for any effects of treatments on normal behavior such as mobility, eye/hair matting and any other abnormal effect, also visual estimation of food and water consumption, body weight gain/loss (body weights will be measured twice weekly) will be checked. Death and observed clinical signs will be recorded in the comment section of data sheet for each animal in detail.

CTX Treatment. 7 days after bone marrow transplantation, CTX (cyclophosphamide) treatment will start by I.P. administration at the following doses: 0, 10, 13, 16, 19, and 40 mg/kg daily for 12 weeks without interruption unless body weight loss>15%. The experimental groups and treatment detail are shown in the table below.

| Groups | Treatment | Vector | Dosing Schedule | Route | N = 10/group |
|---|---|---|---|---|---|
| 1 | No treatment (sham) | Control | QD × 86 | I.P. | 6 |
|   |   | Test | QD × 86 | I.P. | 6 |
| 2 | CTX (10 mg/Kg) | Control | QD × 86 | I.P. | 6 |
|   |   | Test | QD × 86 | I.P. | 6 |
| 3 | CTX (13 mg/Kg) | Control | QD × 86 | I.P. | 6 |
|   |   | Test | QD × 86 | I.P. | 6 |
| 4 | CTX (16 mg/Kg) | Control | QD × 86 | I.P. | 6 |
|   |   | Test | QD × 86 | I.P. | 6 |
| 5 | CTX (19 mg/Kg) | Control | QD × 86 | I.P. | 6 |
|   |   | Test | QD × 86 | I.P. | 6 |
| 6 | CTX (40 mg/Kg) | Control | QD × 86 | I.P. | 6 |
|   |   | Test | QD × 86 | I.P. | 6 |

Sample Collection. Seven days after the first CTX dosage, blood will be collected by tail vein puncture. 100 μL of blood will be collected for an immunophenotyping panel corresponding to LV vector expression and efficacy of shRNA knockdown (see table below). Samples will be analyzed by FACS. An additional 20 μL of blood will be collected to run a full CBC analysis. Collections will be taken from each animal every seven days until termination of study. Bone marrow will be collected at termination of study to assess full engraftment.

| Antibody | Cell Population | Purpose |
|---|---|---|
| Anti-C44 | Expression cassette | Determine expression of LV Vector |
| Anti-CCR5 | Expression cassette | Determine efficacy of shRNA knockdown (though unexpected as shRNA target is human) |
| Anti-CD3 | T cells | Determine lineage expression of LV vector |
| Anti-CD19 | B cells | Determine lineage expression of LV vector |
| CD11c | Dendritic cells | Determine lineage expression of LV vector |
| CD49b | T, NK cells | Determine lineage expression of LV vector |
| CD11b | Neutrophils, eosinophils, monocytes | See above, and to provide closer "real time" analysis of bone marrow engraftment |
| Viability Dye |   | Exclusion of dead cells in analysis |

Termination. Animals that exhibit a continuing deteriorating condition will be humanely euthanized when unacceptable toxicity and/or huge body weight loss (>20%) is noted, or before reaching a comatose state. Animals showing obvious signs of severe distress and/or pain will be humanely euthanized by $CO_2$ followed by cervical dislocation. Termination of study will occur when full engraftment (over 90%) is seen in one animal group.

Example 8

Human Studies

Stem Cell Mobilization and Collection. Three days before collection, patients will begin a 3 to 5-day regimen of G-CSF, to mobilize the $CD34^+$ stem cells. Once the $CD34^+$ cell count in peripheral blood exceeds 10.0 to $20.0 \times 10^6$/kg body weight, apheresis will be performed. This material is transported to GMP facility at 2-8° C. controlled shipping for isolation and transduction of $CD34^+$ stem cells. A target of 3.0 to $4.0 \times 10^6$ $CD34^+$ cells/kg will be collected for a reinfusion of 2 to $3 \times 10^6$ cells/kg. On Day 2 after collection (or day −5 before transplant), the patients will be treated with 15 mg/m² Fludarabine for 5 days (until day −1 before the transplant). Alternatively, on day −1 before the transplant patients will be treated with 4 mg/kg Busulfan. Then the patients will be treated day −2 before the transplant with a single dose of 1000 mg/m² cyclophosphamide.

Cryopreservation of Stem Cells. Patient derived cells (containing hematopoietic stem cells) will, optionally, be centrifuged to develop the cell rich pellet. A solution of heparinized Plasmalyte solution and 10% DMSO (Dimethylsulfoxide) will be added to the plasma supernatant in which the pelleted cells are resuspended. Cells will be initially stored at −4° C., then the sample will be frozen down to the target temperature of −156° C. (when stored in the vapor phase) to −196° C. (when stored in the liquid phase). Cells will be, optionally, shipped in accordance with standard procedure.

Lentiviral Transduction of $CD34^+$ Cells. Upon arrival at GMP facility, $CD34^+$ cells will be isolated by magnetic bead separation. Lentiviral vector-mediated human $CD34^+$ cell transduction includes a 24 h prestimulation of cells in media with the addition of the cytokines Stem Cell Factor (SCF), Fms-related tyrosine kinase 3 ligand (FLT3L), thrombopoietin (TPO), IL-6, IL-2, IL-3, fibronectin, or any combination thereof followed by a 24 h vector exposure (e.g., SEQ ID NO: 2 or SEQ ID NO: 4), both in the presence of the cytokines of SCF, FLT3L and TPO (each 100 ng ml$^{-1}$) in serum-free X-Vivo 10 media. Cells will then be cryopreserved and shipped to clinical site.

Re-infusion of Modified $CD34^+$ Cells. After modified $CD34^+$ cells have been thawed. The current standard washing protocol which follows the New York Blood Center protocol will be used. It includes a two-step dilution of the thawed stem cell unit with 2.5% human serum albumin and 5% dextran 40 followed by centrifugation at 10° C. for 10 min. The supernatant will then be removed and HSA and dextran solution will be again added twice to a final DMSO concentration of less than 1.7%. The washed solution will be infused into the patient as soon as possible. A certain time after the infusion of the cells, such as between 7-45 days, the patient will start taking low dose (50-200 mg or a non-myeloblative dose as described herein) daily oral cyclophosphamide to facilitate the engraftment increase of the gene modified bone marrow cells. It is contemplated that the patient can be $HIV^+$ at the time the modified $CD34^+$ cells are infused, in which case the cells are functioning to treat and/or cure HIV, or the patient can be HIV at the time the modified $CD34^+$ cells are infused, in which case the cells are functioning to prevent a future HIV infection. A schematic for treating an $HIV^+$ patient is provided in FIG. 9 and FIG. 10, but it is to be understood that the patient could also be $HIV^-$.

The above detailed descriptions of embodiments of the technology are not intended to be exhaustive or to limit the technology to the precise form disclosed above. Although specific embodiments of, and examples for, the technology are described above for illustrative purposes, various equivalent modifications are possible within the scope of the technology, as those skilled in the relevant art will recognize. The various embodiments described herein may also be combined to provide further embodiments.

From the foregoing, it will be appreciated that specific embodiments of the technology have been described herein for purposes of illustration, but well-known structures and functions have not been shown or described in detail to avoid unnecessarily obscuring the description of the embodiments of the technology. Where the context permits, singular or plural terms may also include the plural or singular term, respectively.

It will also be appreciated that specific embodiments have been described herein for purposes of illustration, but that various modifications may be made without deviating from the technology. Further, while advantages associated with certain embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

What is claimed is:

1. A method for performing an autologous or allogeneic bone marrow transplant in a human patient infected with HIV, the method comprising:

(i) administering at least one dose of a chemotherapeutic agent to precondition the human patient;

(ii) intravenously administering to the preconditioned human patient of step (i), an effective amount of a population of cyclophosphamide-resistant bone marrow progenitor or stem cells expressing heterologous aldehyde dehydrogenase 1 (ALDH1), wherein the population of cyclophosphamide-resistant bone marrow progenitor or stem cells expressing heterologous ALDH1 is autologous or allogeneic to the human patient; and (iii) orally administering a non-myeloablative dose of cyclophosphamide starting 7 days after administration of the bone marrow progenitor or stem cells of step (ii), every day for five weeks, followed by one week with no cyclophosphamide treatment followed by every day for 1 week of the non-myeloablative dose of cyclophosphamide treatment, wherein the non-myeloablative dose of cyclophosphamide is from 0.16 mg/kg/day to 1.9 mg/kg/day.

2. The method of claim 1, wherein the population of cyclophosphamide-resistant bone marrow progenitor or stem cells expressing ALDH1 are bone marrow stem cells.

3. The method of claim 1, wherein the patient is not immunocompromised as a result of the administration of the at least one non-myeloablative dose of the cyclophosphamide.

4. The method of claim 1, wherein the patient does not experience clinically relevant anemia, neutropenia, thrombocytopenia, pancytopenia, low platelet, low white blood cells, or any combination thereof after administration of the at least one non-myeloablative dose of the cyclophosphamide.

5. The method of claim 1, wherein the population of cyclophosphamide-resistant bone marrow progenitor or stem cells expressing ALDH1 are autologous to the human patient.

6. The method of claim 1, wherein the population of cyclophosphamide-resistant bone marrow progenitor or stem cells expressing heterologous aldehyde dehydrogenase 1 (ALDH1) is produced by introducing a lentiviral vector encoding ALDH1 into unmodified bone marrow progenitor or stem cells, to produce the population of cyclophosphamide-resistant bone marrow progenitor or stem cells expressing ALDH1.

7. The method of claim 1, wherein the population of cyclophosphamide-resistant bone marrow progenitor or stem cells expressing ALDH1 is sensitive to another non-cyclophosphamide chemotherapeutics.

8. The method of claim 1, wherein the population of cyclophosphamide-resistant bone marrow progenitor or stem cells expressing ALDH1 are allogeneic to the human patient.

* * * * *